United States Patent
Mitsuoka et al.

(10) Patent No.: US 8,927,721 B2
(45) Date of Patent: Jan. 6, 2015

(54) NAPHTHYRIDINE DERIVATIVE

(75) Inventors: Yasunori Mitsuoka, Toyonaka (JP); Yuuji Kooriyama, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 13/881,250

(22) PCT Filed: Oct. 27, 2011

(86) PCT No.: PCT/JP2011/074763
§ 371 (c)(1),
(2), (4) Date: Apr. 24, 2013

(87) PCT Pub. No.: WO2012/057248
PCT Pub. Date: Mar. 5, 2012

(65) Prior Publication Data
US 2013/0217705 A1      Aug. 22, 2013

(30) Foreign Application Priority Data
Oct. 29, 2010   (JP) .................................. 2010-244121

(51) Int. Cl.
*C07D 471/04*   (2006.01)
*A61K 31/4375*  (2006.01)
*A61K 31/444*   (2006.01)
*A61K 31/497*   (2006.01)

(52) U.S. Cl.
CPC .................................. *C07D 471/04* (2013.01)
USPC ....... 546/122; 514/300; 514/255.05; 544/405

(58) Field of Classification Search
USPC .......................................... 514/300; 546/122
See application file for complete search history.

(56) References Cited

U.S. PATENT DOCUMENTS

| | | | |
|---|---|---|---|
| 2,899,426 A | 8/1959 | Bloom | |
| 3,115,494 A | 12/1963 | Joseph et al. | |
| 3,227,713 A | 1/1966 | Behner | |
| 3,235,551 A | 2/1966 | Werner | |
| 3,577,428 A | 5/1971 | Suh et al. | |
| 3,636,116 A | 1/1972 | Trepanier | |
| 3,719,674 A | 3/1973 | Trepanier | |
| 3,775,409 A | 11/1973 | Harsanyi et al. | |
| 4,049,807 A | 9/1977 | Paulus et al. | |
| 4,311,840 A | 1/1982 | Condon | |
| 4,895,841 A | 1/1990 | Sugimoto et al. | |
| 4,906,626 A | 3/1990 | Amrein et al. | |
| 5,100,901 A | 3/1992 | Sugimoto et al. | |
| 5,236,942 A | 8/1993 | Miller | |
| 5,328,915 A | 7/1994 | Long et al. | |
| 5,880,147 A | 3/1999 | Yoshida et al. | |
| 5,952,374 A | 9/1999 | Clarkson, Jr. et al. | |
| 6,096,753 A | 8/2000 | Spohr et al. | |
| 6,590,123 B2 | 7/2003 | Bekesi et al. | |
| 6,713,276 B2 | 3/2004 | Cordell et al. | |
| 7,183,070 B2 | 2/2007 | Cordell et al. | |
| 7,309,706 B2 | 12/2007 | Rupp et al. | |
| 7,326,792 B2 | 2/2008 | Shum et al. | |
| 7,414,050 B2 | 8/2008 | Illig et al. | |
| 7,763,609 B2 | 7/2010 | Zhu et al. | |
| 7,902,238 B2 | 3/2011 | Galley et al. | |
| 8,173,642 B2 | 5/2012 | Kobayashi et al. | |
| 2002/0019427 A1 | 2/2002 | Carry et al. | |
| 2005/0165080 A1 | 7/2005 | Rupp et al. | |
| 2006/0173006 A1 | 8/2006 | Sun et al. | |
| 2006/0183790 A1 | 8/2006 | Cole et al. | |
| 2006/0183792 A1 | 8/2006 | Fobare et al. | |
| 2006/0183943 A1 | 8/2006 | Hu et al. | |
| 2007/0004730 A1 | 1/2007 | Zhou et al. | |

(Continued)

FOREIGN PATENT DOCUMENTS

| | | |
|---|---|---|
| CA | 2163724 | 5/1996 |
| CA | 2165386 | 6/1996 |

(Continued)

OTHER PUBLICATIONS

"Side Reactions in Organic Synthesis: A Guide to Successful Synthesis Design" 2005 Wiley-VCH Verlag GmbH & Co. KGaA, Wienheim, chapter 1.*

(Continued)

*Primary Examiner* — John Mabry
*Assistant Examiner* — Daniel Carcanague
(74) *Attorney, Agent, or Firm* — Hamre, Schumann, Mueller & Larson, P.C.

(57) ABSTRACT

The present invention provides, for example, the following compound:

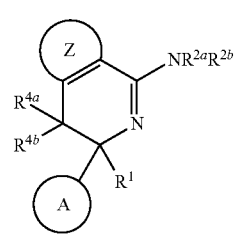

(I)

wherein ring Z is pyridine or a carbocycle, each of which is substituted or unsubstituted, ring A is a carbocycle or a heterocycle, each of which is substituted or unsubstituted, $R^1$ is substituted or unsubstituted alkyl or the like, $R^{2a}$, $R^{2b}$, $R^{4a}$ and $R^{4b}$ are each independently hydrogen or substituted or unsubstituted alkyl or the like, its pharmaceutically acceptable salt or a solvate thereof having an effect of inhibiting amyloid β production, especially a BACE1 inhibitory activity, and useful as a medicament for treating diseases induced by production, secretion or deposition of amyloid β proteins.

16 Claims, No Drawings

(56) References Cited

U.S. PATENT DOCUMENTS

| | | |
|---|---|---|
| 2007/0004786 A1 | 1/2007 | Malamas et al. |
| 2007/0027199 A1 | 2/2007 | Malamas et al. |
| 2007/0224656 A1 | 9/2007 | Cordell et al. |
| 2008/0200445 A1 | 8/2008 | Zhu et al. |
| 2009/0023729 A1 | 1/2009 | Nakamuta et al. |
| 2009/0082560 A1 | 3/2009 | Kobayashi et al. |
| 2010/0075957 A1 | 3/2010 | Tamura et al. |
| 2010/0093999 A1 | 4/2010 | Motoki et al. |
| 2010/0125087 A1* | 5/2010 | Holenz et al. ............... 514/300 |
| 2010/0160290 A1 | 6/2010 | Kobayashi et al. |
| 2010/0234365 A1 | 9/2010 | Liu et al. |
| 2010/0261727 A1 | 10/2010 | Chi et al. |
| 2011/0009395 A1 | 1/2011 | Audia et al. |
| 2011/0046122 A1 | 2/2011 | Andreini et al. |
| 2011/0065695 A1 | 3/2011 | Beauchamp et al. |
| 2011/0190279 A1 | 8/2011 | Hori et al. |
| 2011/0237576 A1 | 9/2011 | Yonezawa et al. |
| 2012/0015961 A1 | 1/2012 | Tamura et al. |
| 2012/0016116 A1 | 1/2012 | Kobayashi et al. |
| 2012/0022249 A1 | 1/2012 | Kobayashi et al. |
| 2012/0172355 A1 | 7/2012 | Tamura et al. |
| 2012/0202828 A1 | 8/2012 | Pineiro et al. |
| 2012/0238548 A1 | 9/2012 | Gabellieri et al. |
| 2012/0238557 A1 | 9/2012 | Masui et al. |
| 2012/0245154 A1 | 9/2012 | Anan et al. |
| 2012/0245155 A1 | 9/2012 | Yoshida et al. |
| 2012/0245157 A1 | 9/2012 | Masui et al. |
| 2012/0253035 A1 | 10/2012 | Narquizian et al. |
| 2012/0258961 A1 | 10/2012 | Suzuki et al. |
| 2012/0258962 A1 | 10/2012 | Hilpert et al. |
| 2012/0295900 A1 | 11/2012 | Hilpert et al. |
| 2013/0158260 A1 | 6/2013 | Kobayashi et al. |
| 2013/0210839 A1 | 8/2013 | Masui et al. |
| 2013/0303755 A1 | 11/2013 | Kobayashi et al. |

FOREIGN PATENT DOCUMENTS

| | | |
|---|---|---|
| DE | 140144 | 2/1980 |
| EP | 0 798 292 | 10/1995 |
| EP | 0 713 704 | 5/1996 |
| EP | 0 718 294 | 6/1996 |
| EP | 0717040 | 6/1996 |
| EP | 1043312 | 10/2000 |
| EP | 1 283 039 | 2/2003 |
| EP | 1 577 294 | 9/2005 |
| EP | 1942105 | 7/2008 |
| EP | 2147914 | 1/2010 |
| EP | 2151435 | 2/2010 |
| EP | 2233474 | 9/2010 |
| EP | 2305672 | 4/2011 |
| EP | 2332943 | 6/2011 |
| EP | 2 360 155 | 8/2011 |
| EP | 2415756 | 2/2012 |
| GB | 1001093 | 8/1965 |
| JP | 62-120374 | 6/1987 |
| JP | 8-231521 | 9/1996 |
| JP | 9-067355 | 3/1997 |
| JP | 10-505862 | 6/1998 |
| JP | 11-349572 | 12/1999 |
| JP | 2005-509651 | 4/2004 |
| JP | 2004-149429 | 5/2004 |
| JP | 2005-517634 | 6/2005 |
| JP | 2005-526005 | 9/2005 |
| JP | 2005-531520 | 10/2005 |
| JP | 2006-519758 | 8/2006 |
| JP | 2009-051828 | 3/2009 |
| JP | 2009-520685 | 5/2009 |
| WO | WO 94/12165 | 6/1994 |
| WO | WO 95/09619 | 4/1995 |
| WO | WO 96/09286 | 3/1996 |
| WO | WO 96/14842 | 5/1996 |
| WO | WO 96/18608 | 6/1996 |
| WO | WO 97/07098 | 2/1997 |
| WO | 97/14686 | 4/1997 |
| WO | 97/38977 | 10/1997 |
| WO | 99/18960 | 4/1999 |
| WO | 00/00200 | 1/2000 |
| WO | WO 01/19788 | 3/2001 |
| WO | WO 01/78709 | 10/2001 |
| WO | WO 01/87293 | 11/2001 |
| WO | 02/062766 | 8/2002 |
| WO | 02/088101 | 11/2002 |
| WO | WO 02/096897 | 12/2002 |
| WO | 03/040096 | 5/2003 |
| WO | WO 03/039446 | 5/2003 |
| WO | WO 03/040115 | 5/2003 |
| WO | WO 03/040142 | 5/2003 |
| WO | WO 03/082191 | 10/2003 |
| WO | 2004/009549 | 1/2004 |
| WO | WO 2004/014843 | 2/2004 |
| WO | 2004/031154 | 4/2004 |
| WO | 2004/039404 | 5/2004 |
| WO | WO 2004/043916 | 5/2004 |
| WO | WO 2004/096795 | 11/2004 |
| WO | WO 2005/014555 | 2/2005 |
| WO | WO 2005/032493 | 4/2005 |
| WO | 2005/058311 | 6/2005 |
| WO | WO 2005/097767 | 10/2005 |
| WO | WO 2005/111031 | 11/2005 |
| WO | 2005/121100 | 12/2005 |
| WO | 2006/009655 | 1/2006 |
| WO | 2006/023750 | 3/2006 |
| WO | 2006/029850 | 3/2006 |
| WO | WO 2006/041404 | 4/2006 |
| WO | WO 2006/041405 | 4/2006 |
| WO | 2005/065277 | 6/2006 |
| WO | WO 2006/065204 | 6/2006 |
| WO | 2006/076284 | 7/2006 |
| WO | 2006/099379 | 9/2006 |
| WO | WO 2006/138192 | 12/2006 |
| WO | WO 2006/138217 | 12/2006 |
| WO | WO 2006/138265 | 12/2006 |
| WO | WO 2006/138304 | 12/2006 |
| WO | 2007/002220 | 1/2007 |
| WO | WO 2007/005366 | 1/2007 |
| WO | WO 2007/005404 | 1/2007 |
| WO | WO 2007/016012 | 2/2007 |
| WO | WO 2007/038271 | 4/2007 |
| WO | 2007/049532 | 5/2007 |
| WO | 2007/058583 | 5/2007 |
| WO | WO 2007/058580 | 5/2007 |
| WO | WO 2007/058582 | 5/2007 |
| WO | WO 2007/058601 | 5/2007 |
| WO | WO 2007/058602 | 5/2007 |
| WO | WO 2007/073284 | 6/2007 |
| WO | WO 2007/078813 | 7/2007 |
| WO | 2007/092846 | 8/2007 |
| WO | 2007/092854 | 8/2007 |
| WO | WO 2007/114771 | 10/2007 |
| WO | WO 2007/120096 | 10/2007 |
| WO | WO 2007/146225 | 12/2007 |
| WO | WO 2008/011560 | 1/2008 |
| WO | 2008/022024 | 2/2008 |
| WO | 2008/073365 | 6/2008 |
| WO | WO 2008/073370 | 6/2008 |
| WO | 2008/103351 | 8/2008 |
| WO | 2008/133273 | 11/2008 |
| WO | 2008/133274 | 11/2008 |
| WO | WO 2009/010454 | 1/2009 |
| WO | 2009/064418 | 5/2009 |
| WO | 2009/091016 | 7/2009 |
| WO | 2009/097278 | 8/2009 |
| WO | 2009/097401 | 8/2009 |
| WO | 2009/097578 | 8/2009 |
| WO | 2009/103626 | 8/2009 |
| WO | 2009/131974 | 10/2009 |
| WO | 2009/131975 | 10/2009 |
| WO | 2009/134617 | 11/2009 |
| WO | 2009/151098 | 12/2009 |
| WO | 2010/019392 | 2/2010 |
| WO | 2010/019393 | 2/2010 |
| WO | WO 2010/013302 | 2/2010 |
| WO | WO 2010/013794 | 2/2010 |

(56) References Cited

FOREIGN PATENT DOCUMENTS

| | | |
|---|---|---|
| WO | 2010/038686 | 4/2010 |
| WO | 2010/047372 | 4/2010 |
| WO | 2010/056194 | 5/2010 |
| WO | 2010/056195 | 5/2010 |
| WO | 2010/056196 | 5/2010 |
| WO | 2010/113848 | 10/2010 |
| WO | 2010/129864 | 11/2010 |
| WO | WO 2010/128058 | 11/2010 |
| WO | 2011/009897 | 1/2011 |
| WO | 2011/009898 | 1/2011 |
| WO | 2011/009943 | 1/2011 |
| WO | WO 2011/005738 | 1/2011 |
| WO | WO 2011/009943 | 1/2011 |
| WO | WO 2011/020806 | 2/2011 |
| WO | 2011/029803 | 3/2011 |
| WO | WO 2011/044181 | 4/2011 |
| WO | WO 2011/044184 | 4/2011 |
| WO | WO 2011/044185 | 4/2011 |
| WO | WO 2011/044187 | 4/2011 |
| WO | 2011/058763 | 5/2011 |
| WO | 2011/060207 | 5/2011 |
| WO | 2011/069934 | 6/2011 |
| WO | 2011/070029 | 6/2011 |
| WO | 2011/070781 | 6/2011 |
| WO | 2011/071057 | 6/2011 |
| WO | 2011/071109 | 6/2011 |
| WO | 2011/071135 | 6/2011 |
| WO | 2011/077726 | 6/2011 |
| WO | WO 2011/080176 | 7/2011 |
| WO | 2011/138293 | 11/2011 |
| WO | 2011/154431 | 12/2011 |
| WO | WO 2011/154374 | 12/2011 |
| WO | 2012/006953 | 1/2012 |
| WO | WO 2012/000933 | 1/2012 |
| WO | 2012/019966 | 2/2012 |
| WO | 2012/038438 | 3/2012 |
| WO | 2012/057247 | 5/2012 |
| WO | 2012/057248 | 5/2012 |
| WO | 2012/085038 | 6/2012 |
| WO | 2012/093148 | 7/2012 |
| WO | 2012/095469 | 7/2012 |
| WO | 2012/095521 | 7/2012 |
| WO | 2012/098064 | 7/2012 |
| WO | 2012/098213 | 7/2012 |
| WO | 2012/098461 | 7/2012 |
| WO | 2012/104263 | 8/2012 |
| WO | 2012/107371 | 8/2012 |
| WO | 2012/110440 | 8/2012 |
| WO | 2012/110441 | 8/2012 |
| WO | 2012/110459 | 8/2012 |
| WO | 2012/117027 | 9/2012 |
| WO | 2012/119883 | 9/2012 |
| WO | 2012/120023 | 9/2012 |
| WO | 2012/126791 | 9/2012 |
| WO | 2012/136603 | 10/2012 |
| WO | 2012/139993 | 10/2012 |
| WO | 2012/147762 | 11/2012 |
| WO | 2012/147763 | 11/2012 |
| WO | 2012/156284 | 11/2012 |
| WO | 2012/162330 | 11/2012 |
| WO | 2012/162334 | 11/2012 |
| WO | 2012/163790 | 12/2012 |
| WO | 2012/168164 | 12/2012 |
| WO | 2012/168175 | 12/2012 |

OTHER PUBLICATIONS

Wermuth; Practice of Medicinal Chemistry, Third Ed., 2008, Elsevier, Chapter 15.*

Beaton et al., "3,4-dihydro-1-isoquinolinamines: a novel class of nitric oxide synthase inhibitors with a range of isoform selectivity and potency," Bioorganic & Medicinal Chemistry Letters, 2001, vol. 11, pp. 1023-1026.

Beaton et al., "The synthesis of 1-aminodihydroisoquinolines by an imine addition cyclisation reaction," 1998, Tetrahedron Letters, vol. 39, pp. 1227-1230.

Tian et al., "Radiosynthesis of 8-Fluoro-3-(4-[$^{18}$F]Fluorophenyl)-3,4-Dihydro-1-Isoquinolinamine ([$^{18}$F]FFDI), a potential PET radiotracer for the inducible nitric oxide synthase," 2008, Current Radiopharmaceuticals, vol. 1, pp. 49-53.

Edwards, et al., "Application of Fragment-Based Lead Generation to the Discovery of Novel, Cyclic Amidine β-Secretase Inhibitors with Nanomolar Potency, Cellular Activity, and High Ligand Efficiency", Journal of Medicinal Chemistry, vol. 50, No. 24, 2007, pp. 5912-5925.

Kuo, et al., "A Synthesis of Estrone via Novel Intermediates. Mechanism of the Coupling Reaction of a Vinyl Carbinol with a β Diketone", The Journal of Organic Chemistry, vol. 33, No. 8, Aug. 1968, pp. 3126-3132.

Cohen, et al., "Synthesis of 2-Amino-5,6-dihydro-4,$H$-1,3-thiazines and Related Compounds by Acid Catalyzed Cyclizationof Allylic Isothiuronium Salts", Journal of Heterocyclic Chemistry, vol. 14, 1977, pp. 717-723.

Hünig, et al., "Azofarbstoffe Durch Oxydative Kupplung, XVIII. Synthese von-3-substituierten Thiazolon-(2)-hydrazonen und Thiazolon-(2)-benzolsulfonylhydrazonen", European Journal of Organic Chemistry, vol. 647, No. 1, May 1961, pp. 66-76.

Schaumann, et al., "Cycloadditionsreaktionen von Heterokumulenen, XXIII. Stickstoffhaltige Fünfring-Heterocyclen aus Carbodiimiden oder Keteniminen mit 3-Dimethylamino-2$H$-azirinen", Liebigs Ann. Chem., 1981, pp. 290-305.

Cambie, et al., "$vic$-Iodothiocyanates and Iodoisothiocyanates. Part 2. New Syntheses of Thiazolidin-2-ones and 2-Amino-2-thiazolines", Journal of the Chemical Society, Perkin Transactions I, No. 3, 1979, pp. 765-770.

Fernández, et al., "Syntheses of β-iodourea derivatives of carbohydrates and glycosylamino-oxazolines", Carbohydrate Research, vol. 216, 1991, pp. 21-32.

Fernández, et al., "Syntheses and Spectral Properties of β-Iodoureas and 2-Amino-4,4-diphenyl-2-oxazolines", Journal of Heterocyclic Chemistry, vol. 28, 1991, pp. 777-780.

Liebscher, et al., "2-Arylimino-3-Thiazolines—Formation of Unusual Tautomers of 2-Arylamino-Thiazolines—a Revision", Tetrahedron Letters, vol. 26, No. 35, 1985, pp. 4179-4180.

Koriyama et al., "Reversal of diastereofacial selectivity in the nucleophilic addition reaction to chiral $N$-sulfinimine and application to the synthesis of indrizidine 223AB," Tetrahedron, vol. 58, 2002, pp. 9621-9628.

Fujisawa et al., "Switchover of diastereofacial selectivity in the condensation reaction of optically active $N$-sulfinimine with ester enolate," Tetrahedron Letters, vol. 37, No. 22, 1996, pp. 3881-3884.

Vilaivan et al., "Recent Advances in Catalytic Asymmetric Addition to Imines and Related C=N Systems," Current Organic Chemistry, vol. 9, 2005, pp. 1315-1392.

Hua et al., "$N$-Alkylidenesulfinamides," Sulfur Reports, vol. 21, 1999, pp. 211-239.

Savoca et al., "1,5-Diazabicyclo[4.3.0]non-5-ene[1]," Encyclopedia of Reagents for Organic Synthesis, 2006, 10 pages total.

Creeke et al., "Synthesis and elaboration of heterocycles via iodocyclisation of unsaturated thioureas," Tetrahedron Letters, 1989, vol. 30, No. 33, pp. 4435-4438.

Mellor et al., A general route to spirocycles by radical additions to exocyclic unsaturated sulphides and related compounds, Tetrahedron Letters, 1991, vol. 32, No. 48, pp. 7111-7114.

Murai et al., "Iodo-cyclization of $N$-homoallyl thioamides leading to 2,4-diaryl-5,6-dihydro-4$H$-1,3-thiazines," Chemistry Letters, 2004, vol. 33, No. 5, pp. 508-509.

Singh et al., "Synthesis of heterocyclic compounds via enamines. Part 8.[†] Acid-catalysed transformations in a 4,4,6-trimethy1-1,4-dihydropyrimidine-2(3$H$)-thione derivatives and related compounds," J. Chem. Soc., Perkin Trans. 1, 1980, pp. 1013-1018.

Kondrat'eva et al., "Noncyclic dimer of 4-methyl-2-dimethlaminooxazole," Izvestiya Akademii Nauk SSSR, Seriya Khimicheskaya, No. 7, Jul. 1977, pp. 1680-1682 (with English translation).

(56) References Cited

OTHER PUBLICATIONS

Database Registry [Online], Chemical Abstracts Service, Columbus, Ohio, US; May 29, 2007, "2H-Indol-2-ome,4-(-2-amino-5,6-dihydro-4-methyl-4H-1,3-thiazin-4-yl)-1,3-dihydro-", XP002646872, Database accession No. 935998-84-8.
Schubert et al., "Neue synthesen von 2-Amino-5,6-dihydro-4H-1,3-thiazinen," Archiv der Pharmazie, 1968, vol. 301, No. 10, pp. 750-762.
Huang et al., "Pharmacophore model construction of (β-secretase inhibitors," 2008, Acta Chimica Sinica, vol. 66, No. 16, pp. 1889-1897 (English language abstract provided).
Clark, et al., "Antitumor Imidazotetrazines. 32.[1] Synthesis of Novel Imidazotetrazinones and Related Bicyclic Heterocycles to Probe the Mode of Action of the Antitumor Drug Temozolomide", J. Med. Chem., vol. 38, 1995, pp. 1493-1504.
Congreve, et al., "Application of Fragment Screening by X-ray Crystallography to the Discovery of Aminopyridines as Inhibitors of β-Secretase", J. Med. Chem., vol. 50, 2007, pp. 1124-1132.
Huang, et al., "Progress in the Development of Nonpeptidomimetic BACE 1 Inhibitors for Alzheimer's Disease", Current Medicinal Chemistry, vol. 16, 2009, pp. 1806-1820.
Goodyer et al., "Synthesis of N-benzyl- and N-phenyl-2-amino-4,5-dihydrothiazoles and thioureas and evaluation as modulators of the isoforms of nitric oxide synthase," Bioorganic & Medicinal Chemistry, 2003, vol. 11, pp. 4189-4206.
Siddiqui et al., "Some extensions of Von Bruan (BrCN) reaction on organic bases," Proc. Pakistan Acad. Sci., 1988, vol. 25, No. 3, pp. 231-240.
Ozawa et al., Pharmacological actions of 2-Aminoethylisothiuronium (AET) derivatives. I[1], Yakugaku Zasshi, 1968, vol. 88, No. 2, pp. 156-162 (English language abstract provided).
Curtis et al., The byozynsethis of Phenols, Part VIII. The synthesis of (2-carboxy-3,5-dihydroxyphynyl)propan-2-one(C-acetyl-o-orsellinic acid). Journal of the Chemical Society, 1964, pp. 5382-5385.
Burton et al., "Addition reactions of quinones. Part I. The reaction of cysteine and thiourea and its derivatives with some quinones," Journal of the Chemical Society, 1952, pp. 2193-2196.
Matsui, "Yomo bochuzai no kenkyu (the 6th report) Kagaku kozo to yhomo shokugai boshi koka tono kankei (III)," Journal of Synthetic Organic Chemistry, Japan, 1950, vol. 8, No. 10, pp. Ho61-Ho65 (and International Search Report issued in PCT/JP2010/055528, which corresponds to co-pending U.S. Appl. No. 13/260,103.
Desai et al., "The condensation of thiocarbamides with monochloroacetic acide and the conversion of arylformamidinethiolacetic acids into pseudothiohydantoin derivatives," Recuil des Travaux Chimiques des Pays-Bas et de la Belgique, 1935, pp. 118-121.
Cole et al., "Acylguanidines as small-molecule beta-secretase inhibitors," J. Med. Chem., 2006, pp. 6158-6161.
Bol'but et al., Heterocyclizations of Functionalized Heterocumulenes with C,N- and C,O-Dinucleophiles: III. Cyclization of N-(1-Aryl-1-chloro-2,2,2-trifluoroethyl)-N'-arylcarbodiimides with 3-Substituted I-Phenylpyrazol-5-ones, Russian Journal of Organic Chemistry, 2003, vol. 29, No. 2, pp. 1789-1791.
Trepanier et al., "Synthesis and screening for antidepressant activity of some aminoindanooxazolines, aminoindanooxazines, and aminoacenaphthoxazolines," Journal of Medicinal Chemistry, 1970, vol. 13, No. 4, pp. 729-733.
Sayed et al., "α-Enones in heterocyclic synthesis of indazole, thiazine, chromene and quinolone derivatives with their antimicrobial activities," Journal of Chemical Research, 2009, vol. 12, pp. 726-728.
Database Caplus [Online] Chemical Abstracts Service, Columbus, Ohio, US; Xu, Yungen et al: "Preparation of benzimidazolyl and benzothiazolyl isothiourea derivatives as nitric oxide synthase inhibitors", XP002679913, retrieved from STN Database accession No. 2005:46620 *abstract* Accessed Jul. 13, 2012.

Bol'but et al., "Synthesis of 4-imino-2-trifluoromethyl-3,4-dihydro-2h-Benzo-[1,3]Thiazines" Chemistry of Heterocyclic Compounds, 2001, vol. 37, No. 4, pp. 522-523.
Vovk et al,, "Intramolecular thermal cyclization of N-(1-Aryl-1-aryloxy-2,2,2-trifluoroethyl)-N'-arylcarbodiimides" Russian Journal of Organic Chemistry, 2000, vol. 36, No. 12, pp. 1739-1742.
Vovk et al., "Regioselective cyclization of I-chloroalkylcarbodiimides with 1,1- and 1,2-bifunctional nucleophilic reagents" Russian Journal of Organic Chemistry, 1997, vol. 33, No. 1, pp. 96-102.
Potts et al., "N-Acyl-β-enamino Ketones: Versatile Heterocyclic Synthons" J. Org. Chem., 1983, 48, pp. 623-625.
Rivkin et al., "Piperazinyl pyrimidine derivatives as potent γ-secretase modulators" Bioorganic & Medicinal Chemistry Letters, 2010, 20, pp. 1269-1271.
Rivkin et al., "Purine derivatives as potent γ-secretase modulators" Bioorganic & Medicinal Chemistry Letters, 2010, 20, pp. 2279-2282.
Vippagunta et al. "Crystalline Solids". Advanced Drug Delivery Reviews, vol. 48, 2001, pp. 3-26.
Gavezzotti. "Are Crystal Structures Predictable". Accounts of Chemical Research, vol. 27, 1994, pp. 309-314.
STN a the Web, RN 79005-45-1, 1964.
Zhu et al., Two novel Diastereoselective Three-Component Reactions of Alkenes or 3,4-Dihydro-(2H)-pyran with Urea/Thiourea-Aldehyde Mixtures: [4 + 2] Cycloaddition vs Biginelli-Type Reaction, Organic Letters, 2006, vol. 8, No. 12, pp. 2599-2602.
Calabrese et al. "NO Synthase and NO-Dependent Signal Pathways in Brain Aging and Neurodegenerative Disorders: The Role of Oxidant/Antioxidant Balance". Neurochemical Balance, vol. 25, No. 9/10, pp. 1315-1341 (2000).
Kavya et al. "Nitric oxide synthase regulation and diversity: Implications in Parkinson's Disease". Nitric Oxide: Biology and Chemistry, vol. 15, No. 4, pp. 280-294 (2006).
Chiou et al. "Review: Effects of Nitric Oxide on Eye Diseases and Their Treatment". Journal of Ocular Pharmacology and Therapeutics, vol. 17, No. 2, pp. 189-198 (2001).
Ishii et al. "Subacute NO generation induced by Alzheimer's β-amyloid in the living brain: reversal by inhibition of the inducible NO synthase". The Federation of American Societies for Experimental Biology Journal, vol. 14, pp. 1485-1489 (2000).
Pak et al. "Morphine via nitric oxide modulates β-amyloid metabolism: a novel protective mechanism for Alzheimer's disease". Medical Science Monitor, vol. 11, No. 10, pp. BR357-BR366 (2005).
Kiselyov et al., "Design and chemical synthesis of [1,2,4]triazol[1,5-c]pyrimidin-5-yl amines, a novel class of VEGFR-2 kinase inhibitors," 2009, Tetrahedron Letters, vol. 50, pp. 3809-3812.
Mulcahy et al., "A stereoselective synthesis of (+)-Gonyautoxin 3," Journal of the American Chemical Society, 2008, vol. 130, pp. 12630-12631.
"Diphenyl Cyanocarbonimidate," e-EROS Encyclopedia of Reagents for Organic Synthesis, 2001, 2 pages total.
Shafik et al., "Synthesis of novel 2-[2-(substituted amino)phenethyl]-1H-benzimidazoles; 3,4-dihydro and 1,2,3,4-tetrahydropyrimido[1,6-α]-benzimidazoles as potential antiulcer agents," 2004, Pharmazie, vol. 59, No. 12, pp. 899-905.
Pohl et al., "Synthesis of partially saturated condensed triazoles by reaction of ω-Aminoalkyl-1,2,4-triazoles with electrophiles," Journal fuer Praktische Chemie Chemiker-Zeitung, 1992, vol. 334, pp. 630-636.
Buschauer et al., "Isohistamine und Homologe als Bausteine von $H_2$-Antagonisten,"Arzneimittel-Forschung, 1985, vol. 35, pp. 1025-1029 (English language abstract provided).
Buschauer et al., "7,8-Dihydroimidazo[1,2-c]pyrimidin-5(6H)-one, -5(6H)-thione and -5(6H)-ylidencyanamide," Chemische Berichte, 1984, vol. 117, pp. 2597-2614.
Borchers et al., "$H_2$-Antihystaminika, 19. Mitt.[1]) Syntheses und $H_2$-antihistaminische Wirkung $N^\alpha$-substituierter Histamine," Archiv der Pharmazie (Weinheim, Germany), 1984, vol. 317, pp. 455-459.
Cheong et al., "Pharmacophore elucidation for a new series of 2-arylpyrazolo-triazolo-pyrimidines as potent human $A_3$ adenosine receptor antagonists," Bioorganic & Medicinal Chemistry Letters, 2011, vol. 21, pp. 2898-2905.

(56) References Cited

OTHER PUBLICATIONS

Xu et al., "Copper-catalyzed cascade synthesis of benzimidazoquinazoline derivatives under mild condition," Chemical Communications, 2011, vol. 47, pp. 5596-5598.

Kishore et al., "QSAR of adenosine receptor antagonists: exploring physicochemical requirements for binding of pyrazolo[4,3-e]-1,2,4-triazolo[1,5-c]pyrimidine derivatives with human adenosine $A_3$ receptor subtype," Bioorganic & Medicinal Chemistry Letters, 2011, vol. 21, No. 2, pp. 818-823.

Dolzhenko et al., "8-methyl-2-[4-(trifluoromethyl)phenyl]-8H-pyrazolo[4,3-e][1,2,4]triazolo[1,5-c]-pyrimidin-5-amine methanol disolvate," Acta Crystallographica, Section E: Structure Reports Online, E66(7), 12 pages total, 2010.

Weinhardt et al. "Synthesis and antidepressant profiles of phenyl-substituted 2-amino- and 2-((alkoxycarbonyl)amino)11,4,5,6-tetrahydropyrimidines," Journal of Medicinal Chemistry, vol. 28, No. 6, 1985, pp. 694-698.

Meschino et al,, "2-Amino-5,6-dihydro-1,3-oxazines. The reduction of carboxylic esters with sodium borohydride," J. Org. Chem., vol. 28, 1963, pp. 3129-3134.

Poos et al., "2-amino-5-aryl-2-oxazolines. Potent new anorectic agent," J. Med. Chem., vol. 6, 1963, pp. 266-272.

Sandin et al., "A fast and parallel route to cyclic isothioureas and guanidines with use of microwave-assisted chemistry," J. Org. Chem., vol. 69, 2004, pp. 1571-1580.

Weinhardt et al., "Synthesis and central nervous system propreties of 2-[(Alkoxycarbonyl)amino]-4(5)-phenyl-2-imidazolines," Journal of Medicinal Chemistry, vol. 27, No. 5, 1984, pp. 616-627.

Woodgate et al., "A new synthesis of 2-amino-2-thiazolines," Heterocycles, vol. 7, No. 1, 1977, pp. 109-112.

Co-pending U.S. Appl. No. 13/941,082, entitled Aminodihydrothiazine Derivatives, filed Jul. 12, 2013.

Co-pending U.S. Appl. No. 13/887,745, entitled Aminodihydrothiazine Derivatives Substituted With a Cyclic Group, filed May 6, 2013.

Co-pending U.S. Appl. No. 13/952,073, entitled Sulfur-Containing Heterocyclic Derivative Having Beta Secretase Inhibitory Activity, filed Jul. 26, 2013.

Co-pending U.S. Appl. No. 14/112,400, entitled Pyridine Derivatives and a Pharmaceutical Composition for Inhibiting BACE1 Containing Them, filed Oct. 17, 2013.

Co-pending U.S. Appl. No. 14/113,327, entitled Oxazine Derivatives and a Pharmaceutical Composition for Inhibiting BACE1 Containing Them, filed Oct. 22, 2013.

Co-pending U.S. Appl. No. 14/070,202, entitled A Pharmaceutical Composition for Treating Alzheimer's Disease, filed Nov. 1, 2013.

Emilio Testa et al.: "Auf das Zentralnervensystem wirkende Substanzen, XXXVI. Weitere Untersuchungen über die 2-substituierten Azetidine"; Justus Liebigs Annalen Der Chemie, vol. 673, No. 1., May 4, 1964, pp. 60-70 XP055091964.

Portnyagin et al.: Russian Journal of Organic Chemistry, Consultants Bureau, US, vol. 10, Jan. 1, 1974, pp. 95-98, XP009174887.

Database Caplus [Online]; Chemical Abstracts Service, Columbus, OH, US; 2006, Bathich, Yaser: "Synthesis of Branched Amino Polyoly and Aminohydroxy Acids: Stereoselective Additiom of C-Nucleophiles ti Isoxazolines and Isoxazolinium Salts and Assignment of Configurations", XP002717806.

Database Registry [Online]; Chemical Abstracts Service, Columbus, OH, US; 3-Pyridinepropanol, .beta., .gamma.-diamino-6-fluoro-.gamma.-(4-fluorophenyl)-, (.beta.-R,.gamma.S)-, Apr. 29, 2004, XP002717807.

Church J et al.: "Anticonvulsant actions of phencyclidine receptor ligands: Correlation with N-Methylaspartate Antagonism in vivo"; General Phamacology, Pergamon Press, Oxford, GB, vol. 21, No. 2, Jan. 1, 1990, pp. 165-170, XP023834032.

Bathich, "Synthesis of branched amino polyols and amino hydroxy acids: stereoselective addition of C-Nucleophiles to isoxazoline and isoxazolinium salts and assignment of configurations," 2006, pp. 148.

\* cited by examiner

NAPHTHYRIDINE DERIVATIVE

TECHNICAL FIELD

The present invention relates to a compound having an effect of inhibiting amyloid β production and is useful as a medicament for treating diseases induced by production, secretion and/or deposition of amyloid β proteins.

BACKGROUND ART

In the brains of patients with Alzheimer's disease, peptides each consisting of approximately 40 amino acids, called amyloid β proteins, which widely accumulate outside neurons to form insoluble plaques (senile plaques) are observed. These senile plaques are considered to kill neurons and cause the onset of Alzheimer's disease, and therefore, agents promoting degradation of amyloid β proteins and amyloid β vaccines have been studied as therapeutic agents for Alzheimer's disease.

Secretases are enzymes which cleave a protein called amyloid precursor protein (APP) within a cell and generate an amyloid β protein. An enzyme which produces N-terminals of amyloid β proteins is called as BACE1 (beta-site APP-cleaving enzyme 1, BACE1). It is considered that production of amyloid β proteins may be suppressed by inhibiting this enzyme, and thus a substance with such an effect can serve as a therapeutic agent for Alzheimer's disease.

Patent Documents 1 and 8 to 19 disclose BACE 1 inhibitors but each of them has a structure different from those of the compounds of the present invention.

Patent Documents 2 to 7 and Non-Patent Documents 1 to 3 disclose compounds having a structure similar to those of the compounds of the present invention have NOS inhibitory activity, HSP90 inhibitory activity or melanocortin 4 receptor binding activity.

PRIOR ART

Patent Document

[Patent Document 1] WO2007/058583
[Patent Document 2] WO2004/039404
[Patent Document 3] WO1997/038977
[Patent Document 4] WO1999/018960
[Patent Document 5] WO2009/097578
[Patent Document 6] WO2005/121100
[Patent Document 7] WO2002/062766
[Patent Document 8] WO2007/049532
[Patent Document 9] WO2008/133274
[Patent Document 10] WO2008/133273
[Patent Document 11] WO2009/151098
[Patent Document 12] WO2010/047372
[Patent Document 13] WO2010/113848
[Patent Document 14] WO2011/071057
[Patent Document 15] WO2011/058763
[Patent Document 16] WO2011/070781
[Patent Document 17] WO2011/077726
[Patent Document 18] WO2011/071135
[Patent Document 19] WO2011/071109

Non-Patent Document

[Non-patent Document 1] Bioorganic & Medicinal Chemistry Letters) Vol. 11, No. 8, p. 1023-1026 (2001)
[Non-patent Document 2] Tetrahedron Letters, Vol. 39, No. 10, p. 1227-1230 (1998)
[Non-patent Document 3] Current Radiopharmaceuticals, Vol. 1, No. 2, p. 49-53 (2008)

DISCLOSURE OF INVENTION

Problems to be Solved by the Invention

The object of the present invention to provide novel compounds which have an effect of inhibiting amyloid β production. Especially, the present invention provides novel compounds which have a BACE1 inhibitory activity and a pharmaceutical composition comprising them.

Means for Solving the Problem

This invention relates to:
(1) A compound of the formula (I):

[Chemical Formula 1]

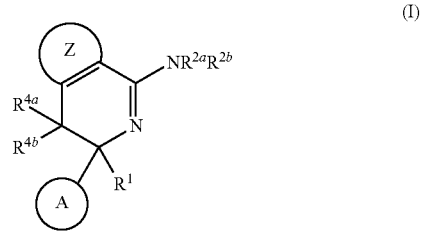

(I)

wherein ring Z is substituted or unsubstituted pyridine or a substituted or unsubstituted carbocycle, ring A is a substituted or unsubstituted carbocycle or a substituted or unsubstituted heterocycle, provided that when ring Z is a substituted or unsubstituted carbocycle, then ring A is

[Chemical Formula 2]

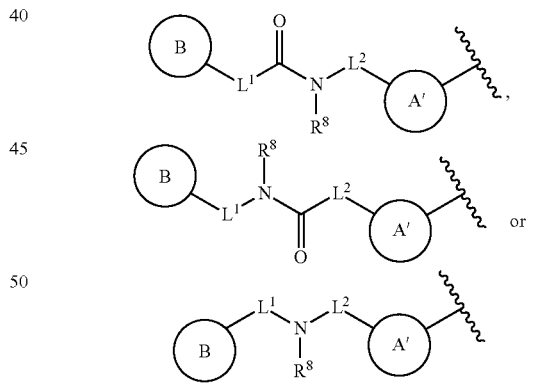

wherein ring A' and ring B are each independently a substituted or unsubstituted carbocycle or a substituted or unsubstituted heterocycle, $L^1$ and $L^2$ are each independently a bond, substituted or unsubstituted alkylene, substituted or unsubstituted alkenylene or substituted or unsubstituted alkynylene, and $R^8$ is hydrogen, substituted or unsubstituted alkyl, substituted or unsubstituted alkenyl, substituted or unsubstituted alkynyl or substituted or unsubstituted acyl, $R^1$ is substituted or unsubstituted alkyl, substituted or unsubstituted alkenyl, substituted or unsubstituted alkynyl, substituted or unsubstituted acyl, cyano, carboxy, substituted or unsubstituted alkoxycarbonyl, substituted or unsubstituted alkenyloxycarbonyl, substituted or unsubstituted alkynyloxycarbonyl, substituted or unsubstituted carbamoyl, substituted or unsubstituted thiocarbamoyl, substituted or unsubstituted carbocyclyl or substituted or unsubstituted heterocyclyl, $R^{2a}$ and $R^{2b}$ are each independently hydrogen, substituted or unsubstituted alkyl, substituted or unsubstituted acyl, substituted or unsubstituted alkoxycarbonyl or substituted or unsubstituted carbamoyl, $R^{4a}$ and $R^{4b}$ are each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted carbocyclyl, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted carbocyclylsulfinyl, substituted or unsubstituted carbocyclylsulfonyl, substituted or unsubstituted heterocyclyl, substituted or unsubstituted heterocyclyloxy, substituted or unsubstituted heterocyclylthio, substituted or unsubstituted heterocyclylalkyl, substituted or unsubstituted heterocyclylalkoxy, substituted or unsubstituted heterocyclyloxycarbonyl, substituted or unsubstituted heterocyclylsulfinyl or substituted or unsubstituted heterocyclylsulfonyl, and $R^{4a}$ and $R^{4b}$ together with the carbon atom to which they are attached may form a substituted or unsubstituted carbocycle or a substituted or unsubstituted heterocycle, its pharmaceutically acceptable salt or a solvate thereof.

(2) The compound according to the above (1) wherein ring Z is substituted or unsubstituted pyridine, its pharmaceutically acceptable salt or a solvate thereof.

(3) The compound according to the above (1) or (2) wherein ring A is

[Chemical Formula 3]

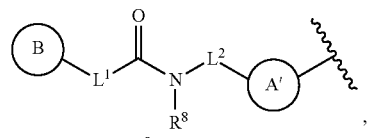

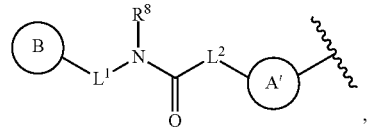

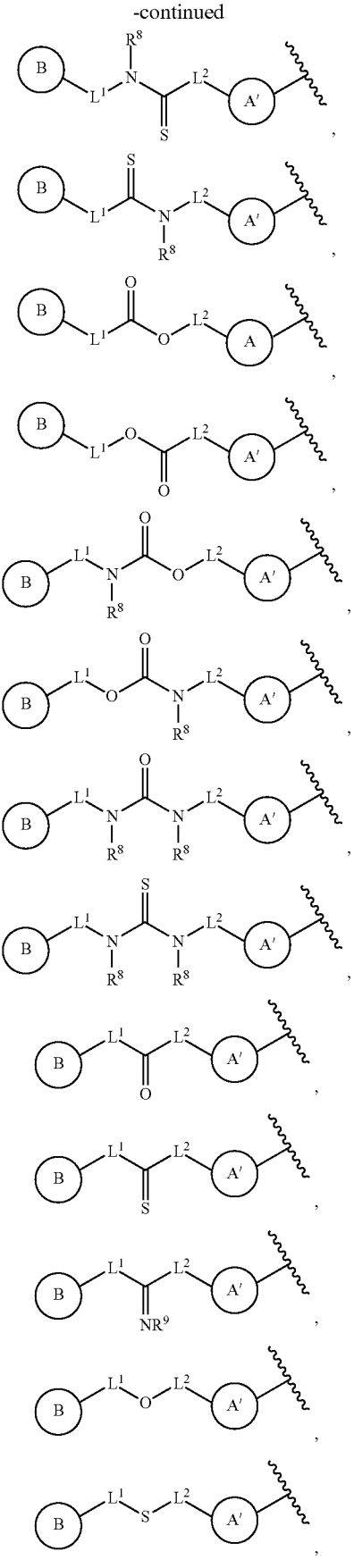

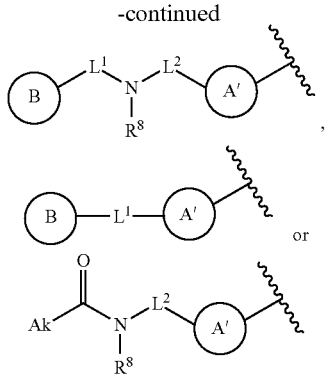

wherein ring A' and ring B are each independently a substituted or unsubstituted carbocycle or a substituted or unsubstituted heterocycle, $L^1$ and $L^2$ are each independently a bond, substituted or unsubstituted alkylene, substituted or unsubstituted alkenylene or substituted or unsubstituted alkynylene, $R^8$ is hydrogen, substituted or unsubstituted alkyl, substituted or unsubstituted alkenyl, substituted or unsubstituted alkynyl or substituted or unsubstituted acyl, $R^9$ is hydrogen, hydroxy, substituted or unsubstituted alkyl, substituted or unsubstituted alkenyl, substituted or unsubstituted alkynyl or substituted or unsubstituted acyl, and Ak is substituted or unsubstituted alkyl, substituted or unsubstituted alkenyl or substituted or unsubstituted alkynyl, its pharmaceutically acceptable salt or a solvate thereof.

(4) The compound according to the above (3) wherein ring A is

[Chemical Formula 4]

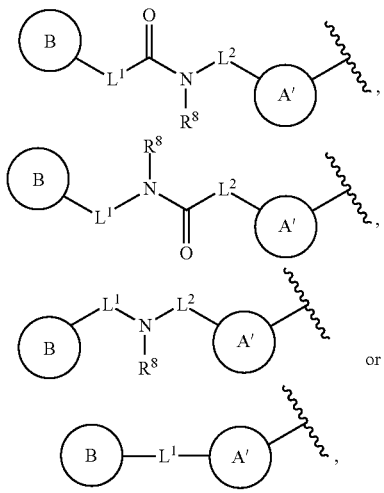

its pharmaceutically acceptable salt or a solvate thereof.

(5) The compound according to the above (3) or (4) wherein each of $L^1$ and $L^2$ is a bond, its pharmaceutically acceptable salt or a solvate thereof.

(6) The compound according to the above (3) or (4) wherein ring A' is substituted or unsubstituted benzene or substituted or unsubstituted pyridine, and ring B is substituted or unsubstituted pyridine, substituted or unsubstituted pyrimidine or substituted or unsubstituted pyrazine, its pharmaceutically acceptable salt or a solvate thereof.

(7) The compound according to any one of the above (1) to (6) wherein $R^1$ is unsubstituted alkyl having a carbon number of 1 to 3, its pharmaceutically acceptable salt or a solvate thereof.

(8) The compound according to the any one of the above (1) to (7) wherein $R^{2a}$ and $R^{2b}$ are both hydrogen, its pharmaceutically acceptable salt or a solvate thereof.

(9) A pharmaceutical composition comprising the compound according to any one of the above (1) to (8), its pharmaceutically acceptable salt or a solvate thereof.

(10) A pharmaceutical composition having BACE1 inhibitory activity comprising the compound according to any one of the above (1) to (8), its pharmaceutically acceptable salt or a solvate thereof.

(11) A method for treating or preventing diseases related to BACE1 comprising administering the compound according to any one of the above (1) to (8) or its pharmaceutically acceptable salt thereof.

(12) Use of the compound according to any one of the above (1) to (8) or its pharmaceutically acceptable salt thereof for manufacturing a medicament for treating or preventing diseases related to BACE1.

(13) A compound according to any one of the above (1) to (8) or its pharmaceutically acceptable salt thereof for use in treating or preventing diseases related to BACE1.

(14) A method for inhibiting BACE1 activity comprising administering the compound according to any one of the above (1) to (8), its pharmaceutically acceptable salt or a solvate thereof.

(15) A compound according to any one of the above (1) to (8), its pharmaceutically acceptable salt or a solvate thereof for use in a method for inhibiting BACE1 activity.

(16) The pharmaceutical composition according to the above (9) or (10) which is a medicament for treating diseases induced by production, secretion or deposition of amyloid β proteins.

(17) A method for treating diseases induced by production, secretion or deposition of amyloid β proteins comprising administering the compound according to any one of the above (1) to (8), its pharmaceutically acceptable salt or a solvate thereof.

(18) A compound according to any one of the above (1) to (8), its pharmaceutically acceptable salt or a solvate thereof for use in a method for treating diseases induced by production, secretion or deposition of amyloid β proteins.

(19) The pharmaceutical composition according to the above (9) or (10) which is a medicament for treating Alzheimer's disease.

(20) A method for treating Alzheimer's disease comprising administering the compound according to any one of the above (1) to (8), its pharmaceutically acceptable salt or a solvate thereof.

(21) The compound according to any one of the above (1) to (8), its pharmaceutically acceptable salt or a solvate thereof for use in treating Alzheimer's disease.

(22) A method, a system, an apparatus, a kit or the like for manufacturing the compound according to any one of the above (1) to (8).

(23) A method, a system, an apparatus, a kit or the like for preparing the pharmaceutical composition comprising the compound according to any one of the above (1) to (8), its pharmaceutically acceptable salt or a solvate thereof.

(24) A method, a system, an apparatus, a kit or the like using the compound according to any one of the above (1) to (8), its pharmaceutically acceptable salt, or a solvate thereof.

Effect of the Invention

The compound of the present invention has BACE1 inhibitory activity and is useful as a medicament for treating and/or preventing disease induced by production, secretion or deposition of amyloid β protein such as Alzheimer's disease.

MODE FOR CARRYING OUT THE INVENTION

Each meaning of terms used herein is described below. In the present specification, unless otherwise noted, each term is used in the same meaning when used alone or in in combination with other words.

In the present specification, the term "halogen" includes fluorine, chlorine, bromine, and iodine.

The halogen portions in "halogenoalkoxy", "halogenoalkyl" and "halogenoalkoxycarbonyl" are the same as the above "halogen".

In the present specification, the term "alkyl" includes linear or branched alkyl having a carbon number of 1 to 15, for example, a carbon number of 1 to 10, for example, a carbon number of 1 to 6, and for example, a carbon number of 1 to 3. Examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, and n-decyl.

The alkyl portions in "alkoxy", "halogenoalkyl", "halogenoalkoxy", "hydroxyalkoxy", "alkoxycarbonyl", "halogenoalkoxycarbonyl", "alkylamino", "aminoalkyl", "alkoxyalkoxy", "alkoxyalkenyloxy", "alkylcarbamoyl", "hydroxyalkylcarbamoyl", "alkoxyimino", "alkylthio", "alkylsulfonyl", "alkylsulfonylamino", "alkylsulfonylalkylamino", "alkylsulfonylimino", "alkylsulfinylamino", "alkylsulfinylalkylamino", "alkylsulfinylimino", "alkylsulfamoyl", "alkylsulfinyl", "carbocyclylalkyl", "carbocyclylalkoxy", "carbocyclylalkoxycarbonyl", "carbocyclylalkylamino", "carbocyclylalkylcarbamoyl", "cycloalkylalkyl", "cycloalkylalkoxy", "cycloalkylalkylamino", "cycloalkylalkoxycarbonyl", "cycloalkylalkylcarbamoyl", "arylalkyl", "arylalkoxy", "arylalkylamino", "arylalkoxycarbonyl", "arylalkylcarbamoyl", "heterocyclylalkyl", "heterocyclylalkoxy", "heterocyclylalkylamino", "heterocyclylalkoxycarbonyl", and "heterocyclylalkylcarbamoyl" are the same as the above "alkyl".

"Substituted or unsubstituted alkyl" may be substituted with one or more substituents selected from a substituent group α.

As used herein, the substituent group α is a group consisting of halogen, hydroxy, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkylcarbamoyl, sulfamoyl, alkylsulfamoyl, alkylsulfinyl, alkylsulfonylamino, alkylsulfonylalkylamino, alkylsulfonylimino, alkylsulfinylamino, alkylsulfinylalkylamino, alkylsulfinylimino, cyano, nitro, carbocyclyl and heterocyclyl wherein each of the carbocycle and heterocycle may be substituted with one or more substituents selected from halogen, alkyl, hydroxy and alkoxy.

Examples of the substituent of "substituted or unsubstituted alkoxy", "substituted or unsubstituted alkoxycarbonyl", "substituted or unsubstituted alkylthio", "substituted or unsubstituted alkylsulfinyl" and "substituted or unsubstituted alkylsulfonyl" are one or more substituents selected from the substituent group α.

Examples of "halogenoalkyl" are trifluoromethyl, fluoromethyl and trichloromethyl.

The term "alkylidene" includes a divalent group of the above "alkyl" and examples include methylidene, ethylidene, propylidene, isopropylidene, butylidene, pentylidene and hexylidene.

The term "alkenyl" includes linear or branched alkenyl having a carbon number of 2 to 15, for example, a carbon number of 2 to 10, for example, a carbon number of 2 to 6, and for example, a carbon number of 2 to 4, having one or more double bonds at any position. Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl.

The term "alkynyl" includes linear or branched alkynyl having a carbon number of 2 to 10, for example, a carbon number of 2 to 8, for example, a carbon number 3 to 6, having one or more triple bonds at any position. Examples include ethynyl, propynyl, butynyl, pentynyl, hexynyl, heptynyl, octynyl, nonynyl and decynyl. These may have further a double bond at any position.

The alkenyl portions in "alkenyloxy", "alkenyloxycarbonyl", "alkoxyalkenyloxy", "alkenylthio", "alkenylsulfinyl", "alkenylsulfonyl" and "alkenylamino" are the same as the above "alkenyl."

The alkynyl portions in "alkynyloxy", "alkynyloxycarbonyl", "alkoxyalkynyloxy", "alkynylthio", "alkynylamino", "alkynylsulfinyl" and "alkynylsulfonyl" are the same as the above "alkynyl."

Examples of the substituent of "substituted or unsubstituted alkenyl", "substituted or unsubstituted alkenyloxy", "substituted or unsubstituted alkenylthio", "substituted or unsubstituted alkenyloxycarbonyl", "substituted or unsubstituted alkenylsulfinyl", "substituted or unsubstituted alkenylsulfonyl", "substituted or unsubstituted alkynyl", "substituted or unsubstituted alkynyloxy", "substituted or unsubstituted alkynyloxycarbonyl", "substituted or unsubstituted alkynylthio", "substituted or unsubstituted alkynylsulfinyl" and "substituted or unsubstituted alkynylsulfonyl" are one or more substituents selected form the substituent group α.

Examples of "substituted or unsubstituted alkenyl" and "substituted or unsubstituted alkynyl" as Ak are one or more substituents selected form halogen, hydroxy, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkylcarbamoyl, sulfamoyl, alkylsulfamoyl, alkylsulfinyl, alkylsulfonylamino, alkylsulfonylalkylamino, alkylsulfonylimino, alkylsulfinylamino, alkylsulfinylalkylamino, alkylsulfinylimino, cyano and nitro.

Specific examples are one or more substituents selected from halogen, hydroxy, alkoxy, halogenoalkoxy, hydroxyalkoxy, acyl, acyloxy, carboxy, alkoxycarbonyl, amino, acylamino, alkylamino, alkylthio, carbamoyl, alkylcarbamoyl, cyano and nitro. More specific example is alkoxy.

Examples of the substituents of "substituted or unsubstituted amino", "substituted or unsubstituted carbamoyl", "substituted or unsubstituted thiocarbamoyl" and "substituted or unsubstituted sulfamoyl" are 1 or 2 substituents selected from alkyl, acyl, hydroxy, alkoxy, alkoxycarbonyl, carbocyclyl and heterocyclyl.

The term "acyl" includes formyl, alkylcarbonyl, alkenylcarbonyl, alkynylcarbonyl, carbocyclylcarbonyl, and heterocyclylcarbonyl. Examples are formyl, acetyl, propionyl, butyryl, isobutyryl, valeryl, pivaloyl, hexanoyl, acryloyl, propioloyl, methacryloyl, crotonoyl, benzoyl, cyclohexanecarbonyl, pyridinecarbonyl, furancarbonyl, thiophenecarbonyl, benzothiazolecarbonyl, pyrazinecarbonyl, piperidinecarbonyl and thiomorpholino.

The acyl portions in "acyloxy" and "acylamino" are the same as the above "acyl".

Examples of the substituents of "substituted or unsubstituted acyl" and "substituted or unsubstituted acyloxy" are one or more substituents selected from the substituent group α. The ring portions of carbocyclylcarbonyl and heterocyclylcarbonyl may be substituted with one or more substituents selected from alkyl, the substituent group α, and alkyl substituted with one or more substituents selected from the substituent group α.

The term "carbocyclyl" includes cycloalkyl, cycloalkenyl, aryl and non-aromatic fused carbocyclyl.

The term "cycloalkyl" includes carbocyclyl having a carbon number of 3 to 10, for example, a carbon number of 3 to 8, and for example, a carbon number 4 to 8. Examples are cyclopropyl, cyclobutyl, cyclopentyl, cyclohexyl, cycloheptyl, cyclooctyl, cyclononyl and cyclodecyl.

The cycloalkyl portions in "cycloalkylalkyl", "cycloalkyloxy", "cycloalkylalkoxy", "cycloalkylthio", "cycloalkylamino", "cycloalkylalkylamino", "cycloalkylsulfamoyl", "cycloalkylsulfonyl", "cycloalkylcarbamoyl", "cycloalkylalkylcarbamoyl", "cycloalkylalkoxycarbonyl" and "cycloalkyloxycarbonyl" are the same as the above "cycloalkyl."

The term "cycloalkenyl" includes a group having one or more double bonds at any position in the ring of the above "cycloalkyl". Examples are cyclopropenyl, cyclobutenyl, cyclopentenyl, cyclohexenyl, cycloheptynyl, cyclooctynyl and cyclohexadienyl.

The term "aryl" includes phenyl, naphthyl, anthryl and phenanthryl. Specific example is phenyl.

The term "non-aromatic fused carbocyclyl" includes non-aromatic groups wherein two or more rings selected from the above "cycloalkyl", "cycloalkenyl" and "aryl" are fused. Examples are indanyl, indenyl, tetrahydronaphthyl and fluorenyl.

The term "carbocycle" as ring Z includes i) an aromatic carbocycle, cycloalkene wherein a ring bond fused with a dihydropyridine ring is a double bond, and a non-aromatic fused carbocycle wherein a ring bond fused with a dihydropyridine ring is a double bond.

Examples of the "aromatic carbocycle" are benzene, naphthalene, anthracene, and phenanthrene.

The term "cycloalkene" includes a ring having a carbon number of 3 to 10, for example, a carbon number of 3 to 8, and for example a carbon number of 4 to 8 and having one or more double bonds at any position in the carbocycle. Examples are cyclopropene, cyclobutene, cyclopentene, cyclohexene, cycloheptene, cyclooctene and cyclohexadiene.

The term "non-aromatic fused carbocycle" includes non-aromatic rings wherein two or more rings selected from the "cycloalkane", "cycloalkene" and "aromatic carbocycle" are fused and wherein a ring bond fused with a dihydropyridine ring is a double bond.

The term "cycloalkane" includes cyclopropane, cyclobutane, cyclopentane, cyclohexane, cycloheptane, cyclooctane, cyclononane and cyclodecane.

One embodiment of a carbocycle as ring Z is benzene.

The term "carbocycle" as other than ring Z includes the above cycloalkane, cycloalkene, an aromatic carbocycle and a non-aromatic carbocycle.

The carbocycle portions in "carbocyclyloxy", "carbocyclylalkyl", "carbocyclylalkoxy", "carbocyclylalkoxycarbonyl", "carbocyclylthio", "carbocyclylamino", "carbocyclylalkylamino", "carbocyclylcarbonyl", "carbocyclylsulfamoyl", "carbocyclylsulfinyl", "carbocyclylsulfonyl", "carbocyclylcarbamoyl", "carbocyclylalkylcarbamoyl" and "carbocyclyloxycarbonyl" are the same as the above "carbocyclyl".

The aryl portions in "arylalkyl", "aryloxy", "aryloxycarbonyl", "arylalkoxycarbonyl", "arylthio", "arylamino", "arylalkoxy", "arylalkylamino", "arylsulfonyl", "arylsulfamoyl", "arylcarbamoyl" and "arylalkylcarbamoyl" are the same as the above "aryl".

The term "heterocyclyl" includes a heterocyclic group comprising one or more rings and having one or more same or different hetero atoms arbitrarily selected from O, S, and N in the ring. Specific examples are 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, and thiadiazolyl;

non-aromatic heterocyclyl such as dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydropyrimidinyl, hexahydroazepinyl, tetrahydrodiazepinyl, tetrahydropyridazinyl, dioxolanyl, dioxazinyl, aziridinyl, dioxolinyl, oxepanyl, thiolanyl, thiinyl, and thiazinyl;

fused bicyclic heterocyclyl such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyridyl, imidazopyrazolyl, pyrazolopyridyl, pyrazolopyrazinyl, thiazolopyridyl, pyrazolopyrimidinyl, pyrazolotriazinyl, pyridazolopyridyl, triazolopyridyl, imidazothiazolyl, pyrazinopyridazinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxinyl, dihydrobenzoxezinyl, dihydrobenzodioxepinyl, and dihydrothienodioxinyl; fused tricyclic heterocyclyl such as carbazolyl, acridinyl, xanthenyl, phenothiazinyl, phenoxathiinyl, phenoxazinyl, dibenzofuryl, imidazoquinolyl, and tetrahydrocarbazolyl. Specific examples are 5- or 6-membered heteroaryl and non-aromatic heterocyclyl.

The heterocycle portions in "heterocycle", "heterocyclylalkyl", "heterocyclyloxy", "heterocyclylthio", "heterocyclylcarbonyl", "heterocyclyloxycarbonyl", "heterocyclylalkoxy", "heterocyclylamino", "heterocyclylsulfamoyl", "heterocyclylsulfinyl", "heterocyclylsulfonyl", "heterocyclylcarbamoyl", "heterocyclyloxycarbonyl", "heterocyclylalkylamino", "heterocyclylalkoxycarbonyl" and "heterocyclylalkylcarbamoyl" are the same as the above "heterocyclyl".

A bond of the above "heterocyclyl" may be situated on any ring.

The term "heteroaryl" includes aromatic cyclic groups among the above "heterocyclyl."

In the present specification, examples of "ring A" are groups of the following formulas:

[Chemical Formula 5]

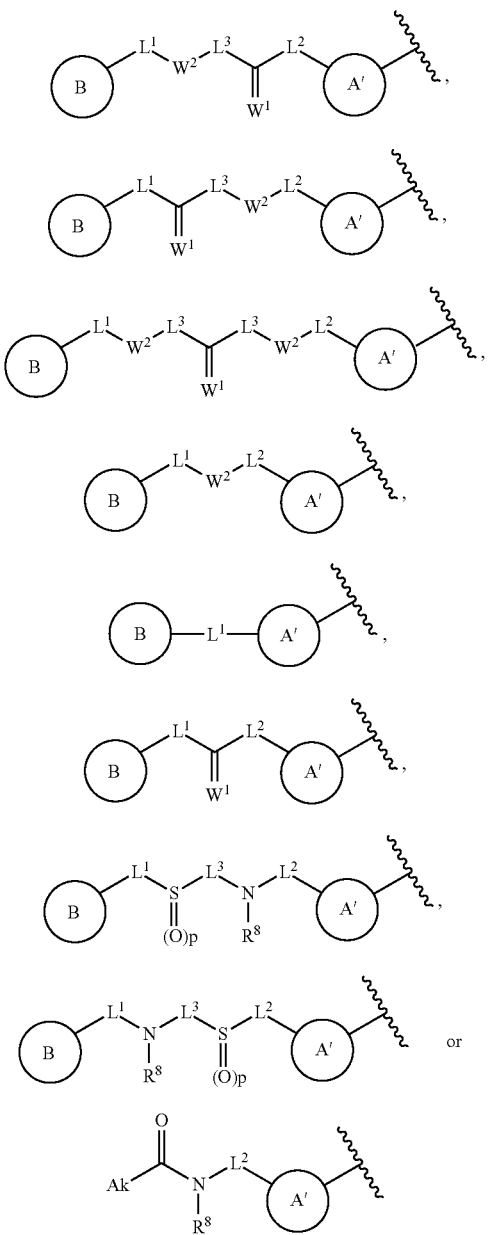

wherein ring A' and ring B are each independently a substituted or unsubstituted carbocycle or a substituted or unsubstituted heterocycle, $L^1$, $L^2$ and $L^3$ are each independently a bond, substituted or unsubstituted alkylene, substituted or unsubstituted alkenylene or substituted or unsubstituted alkynylene, $=W^1$ is $=O$, $=S$ or $=NR^9$, $W^2$ is O, S or NRB, $R^8$ is hydrogen, substituted or unsubstituted alkyl, substituted or unsubstituted alkenyl, substituted or unsubstituted alkynyl or substituted or unsubstituted acyl, $R^9$ is hydrogen, hydroxy, substituted or unsubstituted alkyl, substituted or unsubstituted alkenyl, substituted or unsubstituted alkynyl or substituted or unsubstituted acyl, Ak is substituted or unsubstituted alkyl, substituted or unsubstituted alkenyl or substituted or unsubstituted alkynyl, when ring A is (i), then the constituent carbon atom of $L^1$ and the constituent carbon atom of $L^2$, or the nitrogen atom of $W^2$ and the constituent carbon atom of $L^2$ may be connected with substituted or unsubstituted alkylene to form a ring, when ring A is (ii), then the constituent carbon atom of $L^1$ and the constituent carbon atom of $L^2$, or the constituent carbon atom of $L^1$ and the nitrogen atom of $W^2$ may be connected with substituted or unsubstituted alkylene to form a ring, when ring A is (iii), then two nitrogen atoms of $W^2$ may be connected with substituted or unsubstituted alkylene to form a ring, when ring A is (vi), then the constituent carbon atom of $L^1$ and the constituent carbon atom of $L^2$ may be connected by substituted or unsubstituted alkylene to form a ring, p is 1 or 2, and when multiple $L^3$, multiple $W^2$, multiple $R^9$ or multiple $R^{11}$ are present, each of them may be independently different.

Specific examples are as follows:

[Chemical Formula 6]

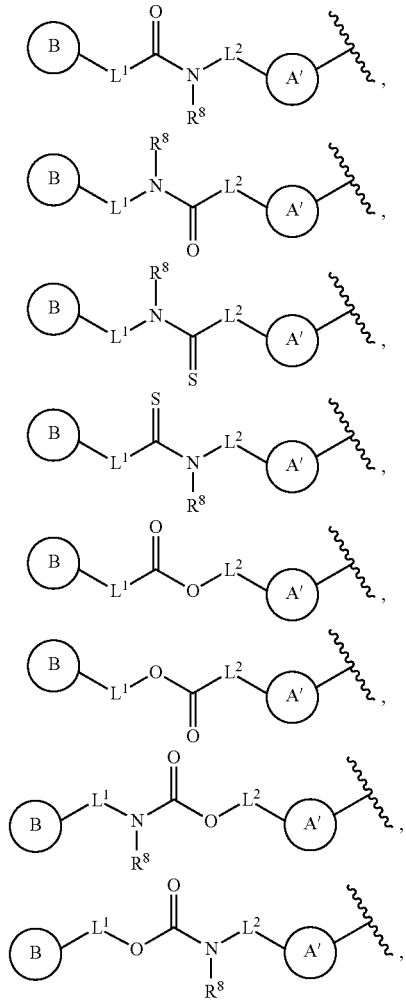

-continued

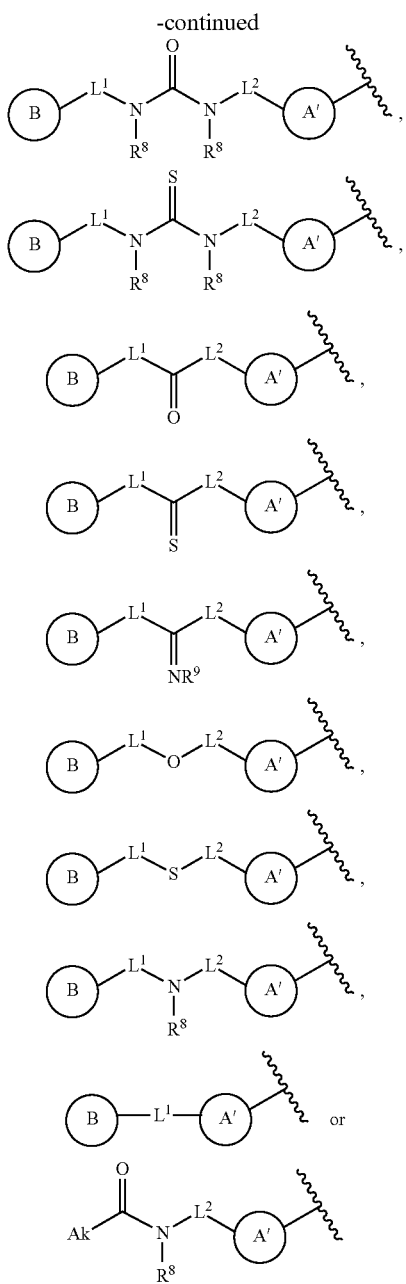

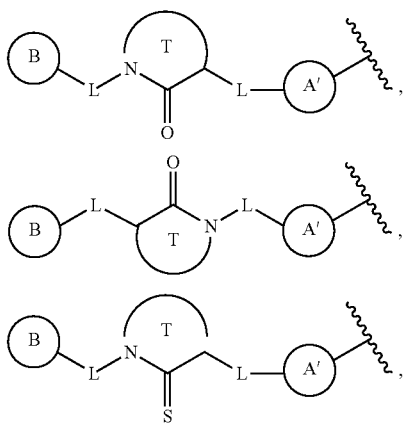

[Chemical Formula 7]

-continued

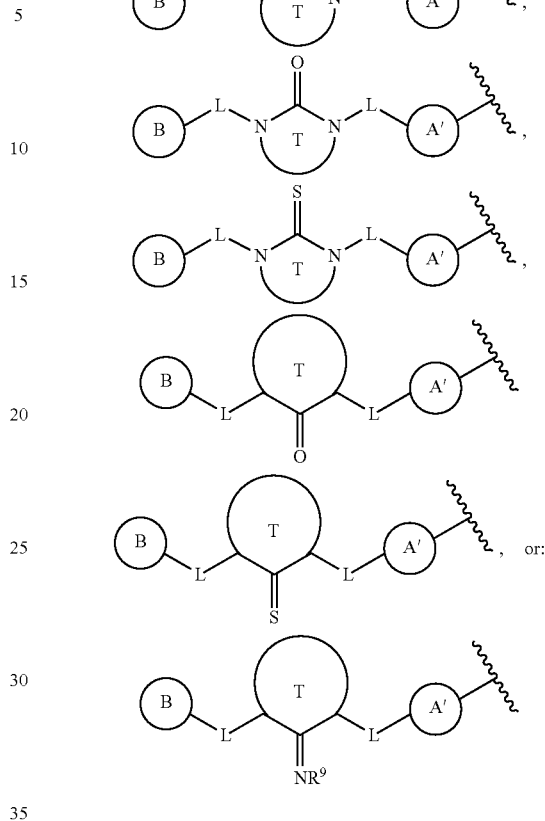

wherein L is each independently a bond, substituted or unsubstituted alkylene, substituted or unsubstituted alkenylene or substituted or unsubstituted alkynylene, ring T is a 5- or 6-membered ring optionally substituted with one or more substituents selected from the substituent group α and other symbols are the same as defined above.

More specific examples are as follows:

[Chemical Formula 8]

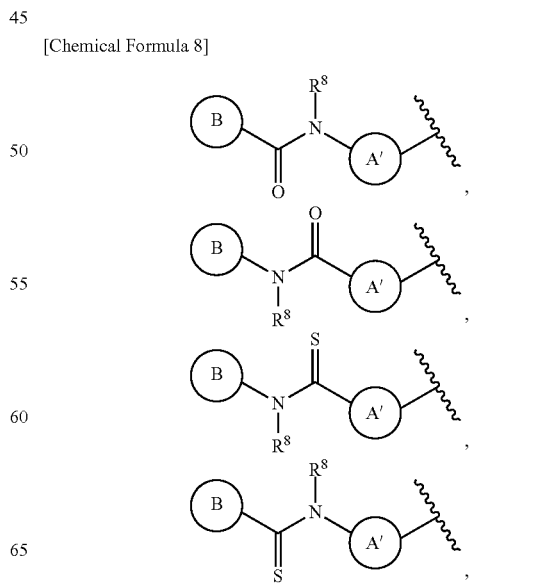

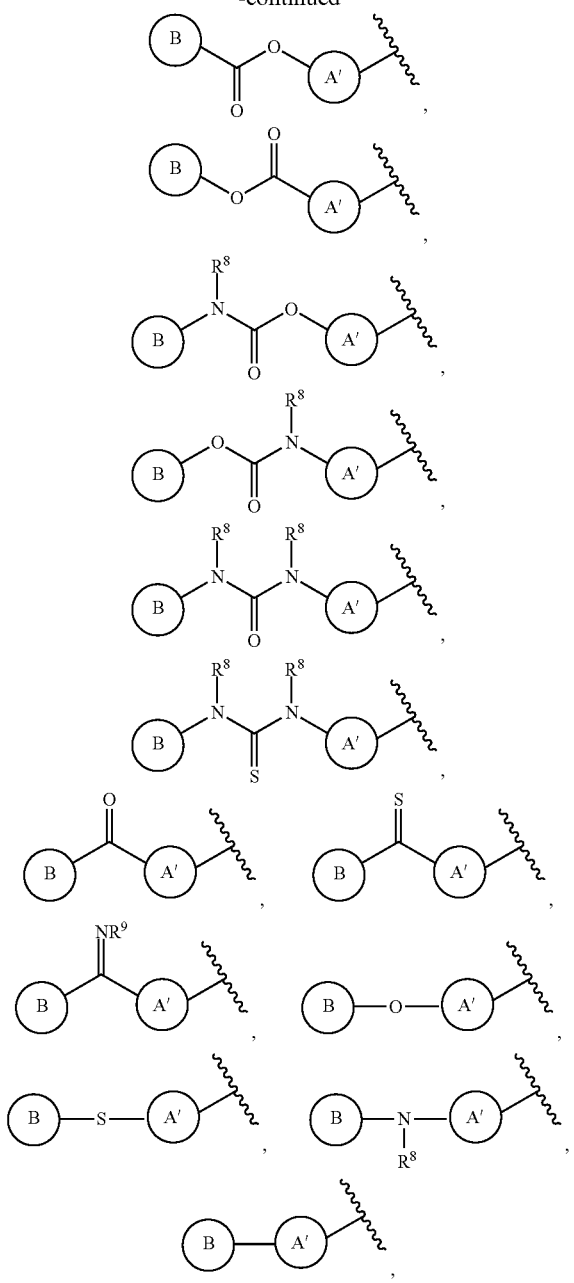
wherein each symbol is the same as defined above,
[Chemical Formula 9]
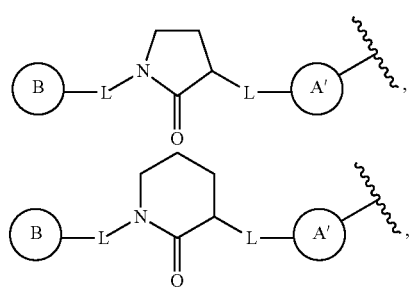
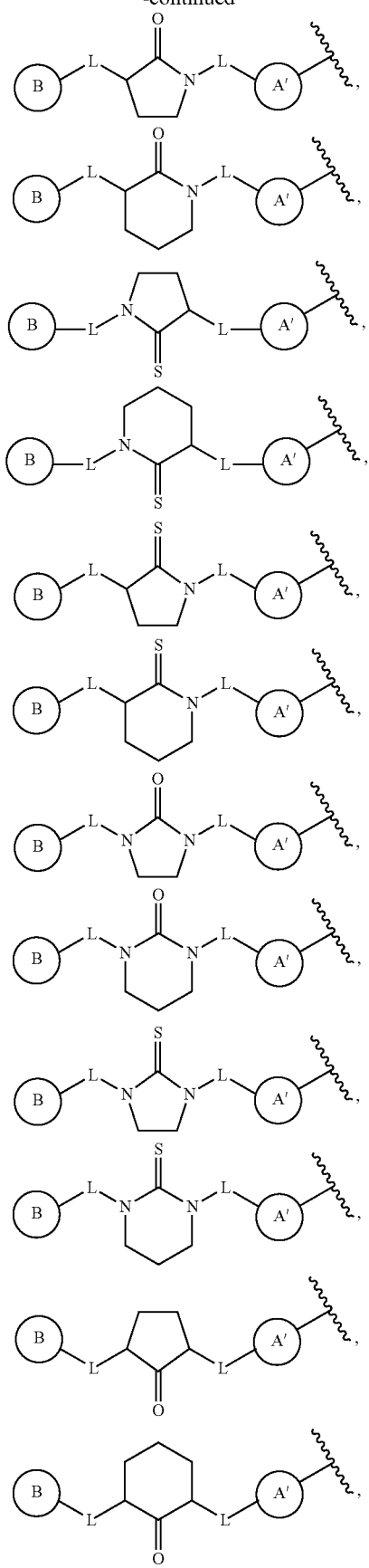

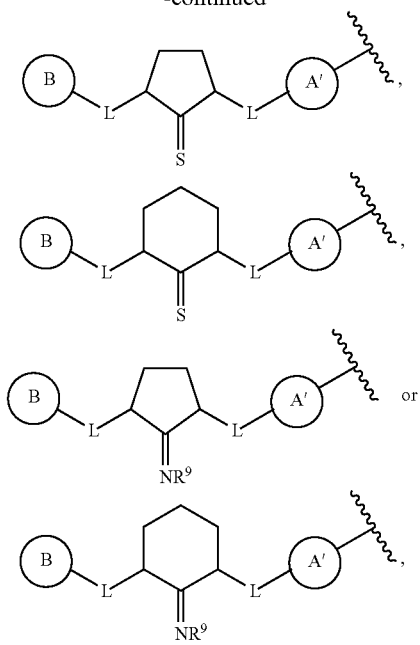

wherein each symbol is the same as defined above.

Other examples of the substituent of "substituted or unsubstituted carbocycle", "substituted or unsubstituted heterocycle", "substituted or unsubstituted benzene", "substituted or unsubstituted pyridine", "substituted or unsubstituted pyrimidine", and "substituted or unsubstituted pyrazine" as ring A and ring B include:

a group selected from the substituent group α such as halogen, hydroxy, alkoxy, acyl, acyloxy, carboxy, alkoxycarbonyl, carbamoyl, amino, cyano, alkylamino and/or alkylthio;
alkyl substituted with one or more substituents selected from the substituent group α, hydroxyimino and alkoxyimino, wherein the substituent is, for example, halogen, hydroxy, alkoxy and/or alkoxycarbonyl; or unsubstituted alkyl;
aminoalkyl substituted with one or more substituents selected from the substituent group α; wherein the substituent is, for example, acyl, alkyl and/or alkoxy; alkenyl substituted with one or more substituents selected from the substituent group α, wherein the substituent is, for example, alkoxycarbonyl, halogen, and/or halogenoalkoxycarbonyl; or unsubstituted alkenyl;
alkynyl substituted with one or more substituents selected from the substituent group α, wherein the substituent is, for example, alkoxycarbonyl; or unsubstituted alkynyl; alkoxy substituted with one or more substituents selected from the substituent group α, wherein the substituent is, for example, halogen, carbamoyl, alkylcarbamoyl and/or hydroxyalkylcarbamoyl;
alkoxyalkoxy substituted with one or more substituents selected from the substituent group α; alkenyloxy substituted with one or more substituents selected from the substituent group α, wherein the substituent is, for example, halogen, hydroxy, amino and/or alkylamino; or unsubstituted alkenyloxy;
alkoxyalkenyloxy substituted with one or more substituents selected from the substituent group α;
alkynyloxy substituted with one or more substituents selected from the substituent group α, wherein the substituent is, for example, halogen and/or hydroxy; or unsubstituted alkynyloxy;
alkoxyalkynyloxy substituted with one or more substituents selected from the substituent group α;
alkylthio substituted with one or more substituents selected from the substituent group α; or unsubstituted alkylthio;
alkenylthio substituted with one or more substituents selected from the substituent group α; or unsubstituted alkenylthio;
alkynylthio substituted with one or more substituents selected from the substituent group α; or unsubstituted alkynylthio;
alkylamino substituted with one or more substituents selected from the substituent group α;
alkenylamino substituted with one or more substituents selected from the substituent group α;
alkynylamino substituted with one or more substituents selected from the substituent group α;
aminooxy substituted with one or more substituents selected from the substituent group α and alkylidene; or unsubstituted aminooxy;
acyl substituted with one or more substituents selected from the substituent group α;
alkylsulfonyl substituted with one or more substituents selected from the substituent group α; or unsubstituted alkylsulfonyl;
alkylsulfinyl substituted with one or more substituents selected from the substituent group α; or unsubstituted alkylsulfinyl;
alkylsulfamoyl substituted with one or more substituents selected from the substituent group α;
carbocyclyl such as cycloalkyl and aryl, substituted with one or more substituents selected from the substituent group α, azide, alkyl and halogenoalkyl;
heterocyclyl substituted with one or more substituents selected from the substituent group α, azide, alkyl and halogenoalkyl;
carbocyclylalkyl such as cycloalkylalkyl and arylalkyl, substituted with one or more substituents selected from the substituent group α, azide, alkyl and halogenoalkyl; or unsubstituted carbocyclylalkyl,
heterocyclylalkyl substituted with one or more substituents selected from the substituent group α, azide, alkyl and halogenoalkyl; or unsubstituted heterocyclylalkyl;
carbocyclyloxy such as cycloalkyloxy and aryloxy, substituted with one or more substituents selected from the substituent group α, azide, alkyl and halogenoalkyl; or unsubstituted carbocyclyloxy such as cycloalkyloxy and aryloxy;
heterocyclyloxy substituted with one or more substituents selected from the substituent group α, azide, alkyl and halogenoalkyl; or unsubstituted heterocyclyloxy; carbocyclylalkoxy such as cycloalkylalkoxy and arylalkoxy, substituted with one or more substituents selected from the substituent group α, azide, alkyl and halogenoalkyl; or unsubstituted carbocyclylalkoxy such as cycloalkylalkoxy and arylalkoxy;
heterocyclylalkoxy substituted with one or more substituents selected from the substituent group α, azide, alkyl and halogenoalkyl; or unsubstituted heterocyclylalkoxy;
carbocyclylalkoxycarbonyl such as cycloalkylalkoxycarbonyl and arylalkoxycarbonyl, substituted with one or more substituents selected from the substituent group α, azide, alkyl and halogenoalkyl; or unsubstituted carbocyclylalkoxycarbonyl such as cycloalkylalkoxycarbonyl and arylalkoxycarbonyl;
heterocyclylalkoxycarbonyl substituted with one or more substituents selected from the substituent group α, azide, alkyl and halogenoalkyl; or unsubstituted heterocyclylalkoxycarbonyl;
carbocyclylthio such as cycloalkylthio and arylthio, substituted with one or more substituents selected from the substituent group α, azide, alkyl and halogenoalkyl; or unsubstituted carbocyclylthio such as cycloalkylthio and arylthio;
heterocyclylthio substituted with one or more substituents selected from the substituent group α, azide, alkyl and halogenoalkyl; or unsubstituted heterocyclylthio; carbocyclylamino such as cycloalkylamino and arylamino, substituted with one or more substituents selected from the substituent group α, azide, alkyl and halogenoalkyl; or unsubstituted carbocyclylamino such as cycloalkylamino and arylamino;
heterocyclylamino substituted with one or more substituents selected from the substituent group α, azide, alkyl and halogenoalkyl; or unsubstituted heterocyclylamino;
carbocyclylalkylamino such as cycloalkylalkylamino and arylalkylamino, substituted with one or more substituents selected from the substituent group α, azide, alkyl and halogenoalkyl; or unsubstituted carbocyclylalkylamino such as cycloalkylalkylamino and arylalkylamino;
heterocyclylalkylamino substituted with one or more substituents selected from the substituent group α, azide, alkyl and halogenoalkyl; or unsubstituted heterocyclylalkylamino;
carbocyclylsulfamoyl such as cycloalkylsulfamoyl and arylsulfamoyl, substituted with one or more substituents selected from the substituent group α, azide, alkyl and halogenoalkyl; or unsubstituted carbocyclylsulfamoyl;
heterocyclylsulfamoyl substituted with one or more substituents selected from the substituent group α, azide, alkyl and halogenoalkyl; or unsubstituted heterocyclylsulfamoyl;
carbocyclylsulfonyl such as cycloalkylsulfonyl and arylsulfonyl, substituted with one or more substituents selected from the substituent group α, azide, alkyl and halogenoalkyl; or unsubstituted carbocyclylsulfonyl such as cycloalkylsulfonyl and arylsulfonyl;
heterocyclylsulfonyl substituted with one or more substituents selected from the substituent group α, azide, alkyl and halogenoalkyl; or unsubstituted heterocyclylsulfonyl;
carbocyclylcarbamoyl such as cycloalkylcarbamoyl and arylcarbamoyl, substituted with one or more substituents selected from the substituent group α, azide, alkyl and halogenoalkyl; or unsubstituted carbocyclylcarbamoyl such as cycloalkylcarbamoyl and arylcarbamoyl;
heterocyclylcarbamoyl substituted with one or more substituents selected from the substituent group α, azide, alkyl and halogenoalkyl; or unsubstituted heterocyclylcarbamoyl;
carbocyclylalkylcarbamoyl such as cycloalkylalkylcarbamoyl and arylalkylcarbamoyl, substituted with one or more substituents selected from the substituent group α, azide, alkyl and halogenoalkyl; or unsubstituted carbocyclylalkylcarbamoyl such as cycloalkylalkylcarbamoyl and arylalkylcarbamoyl;
heterocyclylalkylcarbamoyl substituted with one or more substituents selected from the substituent group α, azide, alkyl and halogenoalkyl; or unsubstituted heterocyclylalkylcarbamoyl;
carbocyclyloxycarbonyl such as cycloalkyloxycarbonyl and aryloxycarbonyl, substituted with one or more substituents selected from the substituent group α, azide, alkyl and halogenoalkyl; or unsubstituted carbocyclyloxycarbonyl such as cycloalkyloxycarbonyl and aryloxycarbonyl;
heterocyclyloxycarbonyl substituted with one or more substituents selected from the substituent group α, azide, alkyl and halogenoalkyl; or unsubstituted heterocyclyloxycarbonyl;
alkylenedioxy substituted with halogen; or unsubstituted alkylenedioxy; oxo; and
azido.

The aforementioned ring of ring A and ring B each may be substituted with one or more substituents selected from the above substituents.

Examples of the substituent of "a substituted or unsubstituted carbocycle", "substituted or unsubstituted benzene", "a substituted or unsubstituted heterocycle", "substituted or unsubstituted pyridine", "substituted or unsubstituted pyrimidine" and "substituted or unsubstituted pyrazine" as ring A' and ring B include one or more selected from halogen, cyano, hydroxy, nitro, carboxy, alkyl substituted with one or more substituents selected from the substituent group α, unsubstituted alkyl, alkoxy substituted with one or more substituents selected from the substituent group α, unsubstituted alkoxy, amino substituted with one or more substituents selected from the substituent group α, unsubstituted amino, carbamoyl substituted with one or more substituents selected from the substituent group α, unsubstituted carbamoyl, alkoxycarbonyl substituted with one or more substituents selected from the substituent group α, and unsubstituted alkoxycarbonyl.

Examples of the substituent of "a substituted or unsubstituted carbocycle", "substituted or unsubstituted benzene", "a substituted or unsubstituted heterocycle" and "substituted or unsubstituted pyridine" as ring A' include one or more substituents selected from halogen, hydroxy, alkyl, alkenyl, alkynyl, alkoxy, alkenyloxy, alkynyloxy, acyl, carboxy, alkoxycarbonyl, amino and cyano.

Specific example is halogen.

Examples of the substituent of "a substituted or unsubstituted carbocycle", "substituted or unsubstituted benzene", "a substituted or unsubstituted heterocycle", "substituted or unsubstituted pyridine", "substituted or unsubstituted pyrimidine" and "substituted or unsubstituted pyrazine" as ring B are one or more substituents selected from halogen, alkyl, alkenyl, alkynyl, alkoxy, alkenyloxy, alkynyloxy and cyano.

Examples of the substituent of "substituted or unsubstituted pyridine" and "a substituted or unsubstituted carbocycle" as ring Z are one or more substituents selected from halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted carbocyclyl, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted carbocyclylsulfinyl, substituted or unsubstituted carbocyclylsulfonyl, substituted or unsubstituted heterocyclyl, substituted or unsubstituted heterocyclyloxy, substituted or unsubstituted heterocyclylthio, substituted or unsubstituted heterocyclylalkyl, substituted or unsubstituted heterocyclylalkoxy, substituted or unsubstituted heterocyclyloxycarbonyl, substituted or unsubstituted heterocyclylsulfinyl and substituted or unsubstituted heterocyclylsulfonyl.

Examples of the substituent of "substituted or unsubstituted carbocyclyl", "substituted or unsubstituted heterocyclyl", "substituted or unsubstituted carbocyclylalkyl", "substituted or unsubstituted carbocyclylalkoxy", "substituted or unsubstituted carbocyclyloxy", "substituted or unsubstituted carbocyclylthio", "substituted or unsubstituted carbocyclyloxycarbonyl", "substituted or unsubstituted carbocyclylsulfinyl", "substituted or unsubstituted carbocyclylsulfonyl", "substituted or unsubstituted heterocyclyloxy", "substituted or unsubstituted heterocyclylthio", "substituted or unsubstituted heterocyclyloxycarbonyl", "substituted or unsubstituted heterocyclylsulfinyl", "substituted or unsubstituted heterocyclylsulfonyl", "a substituted or unsubstituted carbocycle" and "a substituted or unsubstituted heterocycle" as other than the above ring A, ring A', ring B and ring Z are one or more substituents selected from alkyl substituted with one or more substituents selected from the substituent group α, unsubstituted alkyl and the substituent group α.

The term "alkylene" includes a linear or branched divalent carbon chain having a carbon number of 1 to 10, for example, a carbon number of 1 to 6, or a carbon number of 1 to 3. Examples include methylene, dimethylene, trimethylene, tetramethylene, and methyltrimethylene.

The alkylene portion in "alkylenedioxy" is the same as the above "alkylene."

The term "alkenylene" includes a linear or branched divalent carbon chain having a carbon number of 2 to 10, for example, a carbon number of 2 to 6, or a carbon number of 2 to 4, having a double bond at any position. Examples include vinylene, propenylene, butenylene, butadienylene, methylpropenylene, pentenylene and hexenylene.

The term "alkynylene" includes a linear or branched divalent carbon chain having a carbon number of 2 to 10, for example, a carbon number of 2 to 6, or a carbon number of 2 to 4, having a triple bond at any position and, further, optionally having a double bond. Examples include ethynylene, propynylene, butynylene, pentynylene and hexynylene.

Examples of the substituents of "substituted or unsubstituted alkylene", "substituted or unsubstituted alkenylene" and "substituted or unsubstituted alkynylene" include one or more substituents selected from the substituent group α, and specific examples are halogen and hydroxy.

The phrase "$R^{4a}$ and $R^{4b}$ together with the carbon atom to which they are attached may form a substituted or unsubstituted carbocycle or a substituted or unsubstituted heterocycle" includes

[Chemical Formula 10]

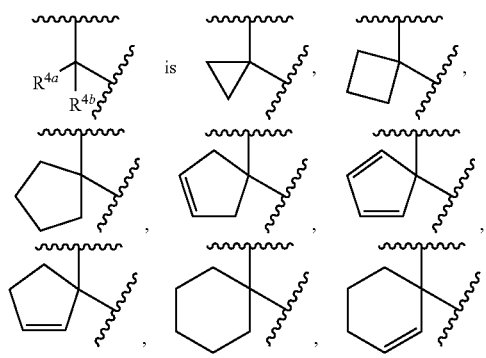

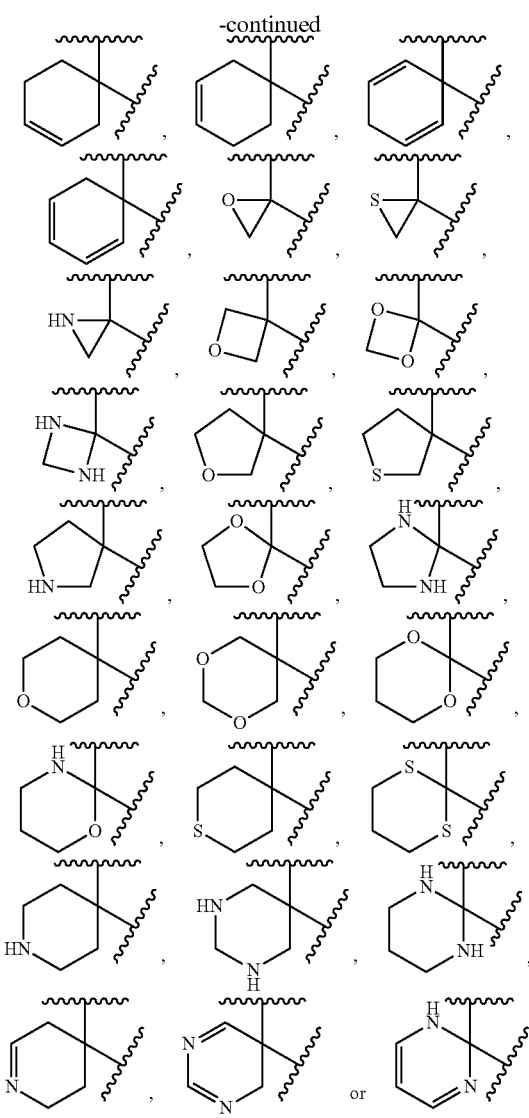

These are optionally substituted with one or more substituents selected from unsubstituted alkyl, the substituent group α and alkyl substituted with one or more selected from the substituent group α at any position.

The compound of the formula (I) is not limited to a specific isomer, and includes all possible isomers such as keto-enol isomers, imine-enamine isomers, diastereoisomers, optical isomers and rotation isomers, racemate and the mixture thereof. For example, the compound of the formula (I) wherein $R^{2a}$ is hydrogen includes the following tautomers.

[Chemical Formula 11]

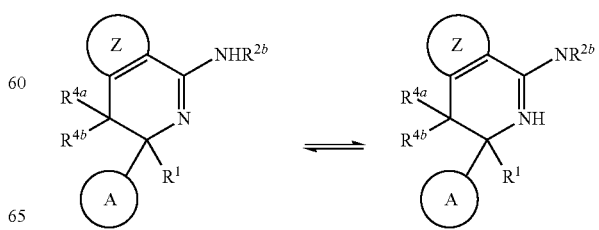

The compound of the formula (I) has an asymmetric carbon atom and includes the following optical isomers.

[Chemical Formula 12]

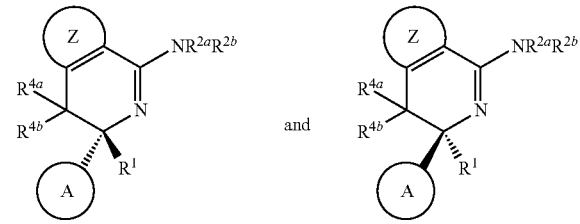

Preferable isomer is as follows.

[Chemical Formula 13]

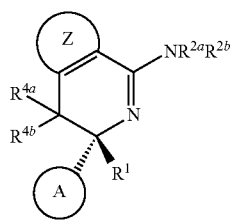

The optical isomer of the compound of the formula (I) can be obtained by known methods such as chiral chromatography or diastereomer salt formation using an optical active acid or base.

The compounds of the formulas (Ia) to (Ie) mentioned below also include similar tautomers.

One or more hydrogens, carbons and/or other atoms of the compound of the formula (I) can be replaced by isotopes of the hydrogens, carbons and/or other atoms. Examples of isotopes include ones of hydrogen, carbon, nitrogen, oxygen, phosphorous, sulfur, fluorine, iodine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{123}$I and $^{36}$Cl, respectively. The compound of the formula (I) also includes the compound replaced by such isotopes. The compound replaced by such isotopes is useful also as a medicament, and includes all the radiolabeled compounds of the compound of the formula (I). The invention includes "radiolabelling method" for manufacturing the "radiolabeled compound" and the method is useful as a tool of metabolic pharmacokinetic research, the research in binding assay and/or diagnosis.

Radiolabeled compounds of the compound of the formula (I) can be prepared by methods known in the art. For example, tritiated compounds of the formula (I) can be prepared by introducing tritium into the particular compound of the formula (I) such as by catalytic dehalogenation with tritium. This method may include reacting a suitably halogen-substituted precursor of the compound of the formula (I) with tritium gas in the presence of a suitable catalyst such as Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). $^{14}$C-labeled compounds can be prepared by employing starting materials having a $^{14}$C carbon.

As pharmaceutically acceptable salt of the compound of the formula (I), examples include salts with alkaline metals (e.g. lithium, sodium and potassium), alkaline earth metals (e.g. calcium and barium), magnesium, transition metal (e.g. zinc and iron), ammonia, organic bases (e.g. trimethylamine, triethylamine, dicyclohexylamine, ethanolamine, diethanolamine, triethanolamine, meglumine, diethanolamine, ethylenediamine, pyridine, picoline, quinoline), and amino acids, and salts with inorganic acids (e.g. hydrochloric acid, sulfuric acid, nitric acid, carbonic acid, hydrobromic acid, phosphoric acid and hydroiodic acid) and organic acids (e.g. formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid and ethanesulfonic acid). Specific examples are salts with hydrochloric acid, sulfuric acid, phosphoric acid, tartaric acid, or methanesulfonic acid. These salts may be formed by usual methods.

The compound of the formula (I) or its pharmaceutically acceptable salt may form solvate such as hydrate, and/or crystalline polymorphism, and the present invention also includes such various kinds of solvate and crystalline polymorphism. The "solvate" includes a compound of the formula (I) which coordinate arbitrary number of solvent molecules such as water molecules. The compound of the formula (I) or its pharmaceutically acceptable salt can adhere water or form hydrate by absorbing water molecules after leaving in the atmosphere. Moreover, the compound of the formula (I) or its pharmaceutically acceptable salt can form the crystalline polymorphism by recrystallization.

The compound of the formula (I) of the present invention or its pharmaceutically acceptable salt may form prodrug, and the present invention also includes such various kinds of prodrug. Prodrug is a derivative of the compound of the present invention having a group which can be chemically or metabolically decomposed and the one which becomes a pharmaceutically active compound of the present invention by solvolysis or physiological conditions in vivo. Prodrug includes a compound which converts into the compound of the formula (I) by enzymatical oxidation, reduction, hydrolysis or the like under physiological conditions in a living body, and a compound which converts into the compound of the formula (I) by hydrolyzing by stomach acid or the like. The method of selecting suitable prodrug derivatives and the method of manufacturing them are disclosed in Design of Prodrugs, Elsevier, and Amsterdam 1985. Prodrug itself may possess the activity.

When the compound of the formula (I) or its pharmaceutically acceptable salt has a hydroxy group, examples of the prodrug includes acyloxy derivatives and sulfonyloxy derivatives which can be prepared by reacting a compound having a hydroxy group with a suitable acid halide, suitable acid anhydride, suitable sulfonyl chloride, suitable sulfonylanhydride or mixed anhydride, or by reacting with a condensation agent. For example, $CH_3COO-$, $C_2H_5COO-$, t-BuCOO—, $C_{15}H_{31}COO-$, PhCOO—, COO(m-NaOOCPh)—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3-O-PhSO_3-$, $PhSO_3-$, and p-$CH_3PhSO_3-$ are exemplified.

The compound of the formula (I) includes the compounds of the following formulas (Ia) to (Ie).

[Chemical Formula 14]

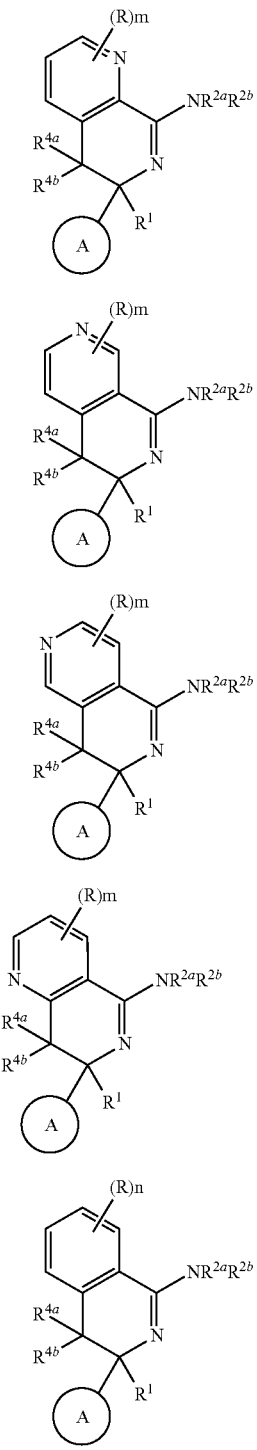

and wherein R is each independently
halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted carbocyclyl, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted carbocyclylsulfinyl, substituted or unsubstituted carbocyclylsulfonyl, substituted or unsubstituted heterocyclyl, substituted or unsubstituted heterocyclyloxy, substituted or unsubstituted heterocyclylthio, substituted or unsubstituted heterocyclylalkyl, substituted or unsubstituted heterocyclylalkoxy, substituted or unsubstituted heterocyclyloxycarbonyl, substituted or unsubstituted heterocyclylsulfinyl or substituted or unsubstituted heterocyclylsulfonyl, m is an integer of 0 to 3, n is an integer of 0 to 4, and other symbols are the same as defined above.

The present compounds of the formulas (I), (Ia) to (Ie) can be prepared, for example, by general synthesis procedures shown below. Extract, purification or the like can be performed by the usual procedure in the experiment of the organic chemistry.

Synthesis of the compound of the present invention can be carried out according to the known methods in the technical field.

In the case that a substituent which inhibits a reaction (e.g. hydroxy, mercapto, amino, formyl, carbonyl and carboxy) exists in any of the following steps, the substituent may be preliminarily protected by, for example, the method described in "Protective Groups in Organic Synthesis, Theodora W Green (John Wiley & Sons)" and the protecting group may be removed at an appropriate step.

During all the following steps, the order of the steps to be performed may be appropriately changed. In each step, an intermediate may be isolated and then used in the next step.

1) Synthesis of Compound (I)

[Chemical Formula 15]

wherein Hal is halogen and other symbols are the same as defined above.

Step 1

Compound 1 which is commercially available or can be prepared by known methods is reacted with an oxalyl chloride, thionyl chloride or the like in the absence or presence of a catalytic N,N,-dimethylformamide in a solvent such as toluene, dichloromethane, tetrahydrofuran or a mixed solvent thereof at a temperature between −40° C. and reflux temperature of the solvent, preferably −10° C. to 30° C. for 0.1 to 24 hours, preferably 0.1 to 6 hours. To the reaction solution is added an ammonia source such as 28% aqueous ammonia, an aqueous ammonia dioxane solution, an aqueous ammonia ether solution and reacted for 0.1 to 24 hours, preferably 0.1 to 6 hours to afford Compound 2.

Step 2

Compound 2 is reacted in the presence of a base such as triethylamine or diisopropylethylamine and a dehydrating agent such as trifluoroacetic anhydride in a solvent such as toluene, dichloromethane, or tetrahydrofuran at a temperature between −40° C. and reflux temperature of the solvent, preferably −10 to 30° C. for 0.1 to 24 hours, preferably 0.1 to 6 hours to afford Compound 3.

[Chemical Formula 16]

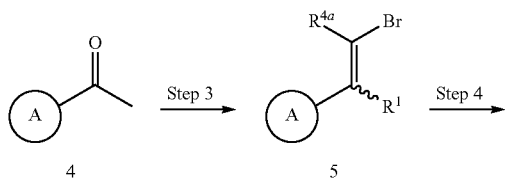

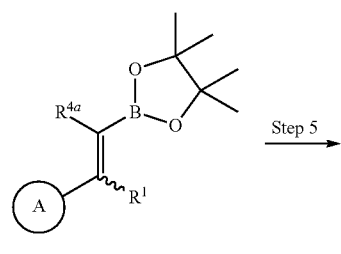

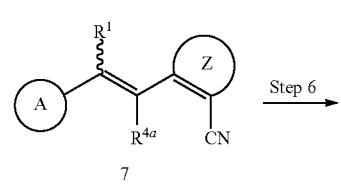

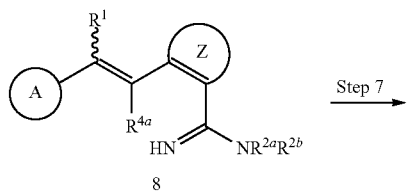

-continued

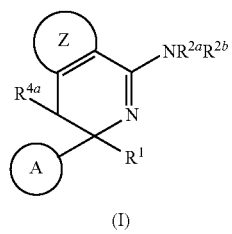

(I)

wherein wavy line includes a cis isomer and a trans isomer about the double bond and each symbol is the same as defined above.

Step 3

(Bromomethyl)triphenylphosphonium bromide and a base such as potassium-t-butoxide or sodium-t-butoxide are reacted in a solvent such as toluene, dichloromethane, or tetrahydrofuran at a temperature between −40° C. and reflux temperature of the solvent, preferably −10 to 40° C. for 0.1 to 24 hours, preferably 0.1 and 6 hours. To the reaction solution is added a solution of Compound 4 which is commercially available or can be prepared by known methods in toluene, dichloromethane, tetrahydrofuran or the like and reacted for 0.1 to 24 hours, preferably 0.1 to 6 hours to afford Compound 5.

Step 4

To a solution of Compound 5 in a solvent such as toluene, dioxane, or tetrahydrofuran are added subsequently a boron reagent such as bis(pinacolate)diboron, a base such as potassium acetate and a divalent palladium reagent such as [1,1'-bis(diphenylphosphino)ferrocene]palladium(In)dichloride dichloromethane complex (1:1) at a temperature between −40° C. to reflux temperature of the solvent, preferably −10 and 40° C. The mixture is reacted at a temperature between room temperature and reflux temperature of the solvent, preferably room temperature and 80° C. for 0.1 and 24 hours to afford Compound 6.

Step 5

To a solution of Compound 6 in a solvent such as toluene, dichloromethane, dioxane, or tetrahydrofuran, are added Compound 3 obtained in Step 2, a 2M aqueous potassium carbonate solution or a 2M aqueous sodium carbonate solution and a divalent palladium reagent such as [1,1'-bis(diphenylphosphino)ferrocene]palladium(II)dichloride dichloromethane complex (1:1) at a temperature between −40° C. and reflux temperature of the solvent, preferably −10 and 40° C. The mixture is reacted at a temperature between room temperature and reflux temperature of the solvent for 0.1 and 24 hours to afford Compound 7.

Step 6

To a solution of an ammonia source such as ammonium chloride, ammonium acetate, or ammonium formate in a solvent such as toluene, dichloromethane, dioxane, or tetrahydrofuran is added a metal reagent such as trimethylaluminium at a temperature between −40° C. and reflux temperature of the solvent, preferably −10 and 40° C. The mixture is reacted at a temperature between −40° C. and reflux temperature of the solvent, preferably −10 and 40° C. for 0.1 to 24 hours, preferably 0.1 to 6 hours. To the reaction solution is added a solution of Compound 7 in toluene, dichloromethane, dioxane, tetrahydrofuran or the like and reacted at a temperature between room temperature and reflux temperature of the solvent for 1 to 48 hours, preferably 1 to 30 hours to afford Compound 8.

Step 7

Compound 8 is dissolved in an acid such as sulfuric acid, hydrochloric acid, or technical grade sulfuric acid and reacted at a temperature between 0 and 60° C., preferably 0 and 40° C. for 1 to 48 hours, preferably 1 to 30 hours. To the reaction solution is added nitric acid at a temperature between −10 and 40° C. and the mixture is reacted for 0.1 to 24 hours, preferably 0.1 to 6 hours to afford Compound (I).

When $NR^{2a}R^{2b}$ of the obtained Compound (I) is an amino group protected by an amino protecting group such as t-butoxycarbonyl, the obtained compound is dissolved in a hydrochloric acid methanol solution, a trifluoroacetic acid dichloromethane solution, a hydrochloric acid dioxane solution, formate or the like and reacted at a temperature between −40° C. and reflux temperature of the solvent, preferably −10 and 40° C. for 0.1 to 48 hours, preferably 0.5 to 12 hours to afford the deprotected Compound (I).

Alternatively, an amino protecting group can be deprotected according to the methods in Protective Groups in Organic Synthesis, Theodora W Green (John Wiley & Sons) or the like.

2) Synthesis of Compound (Ig)

[Chemical Formula 17]

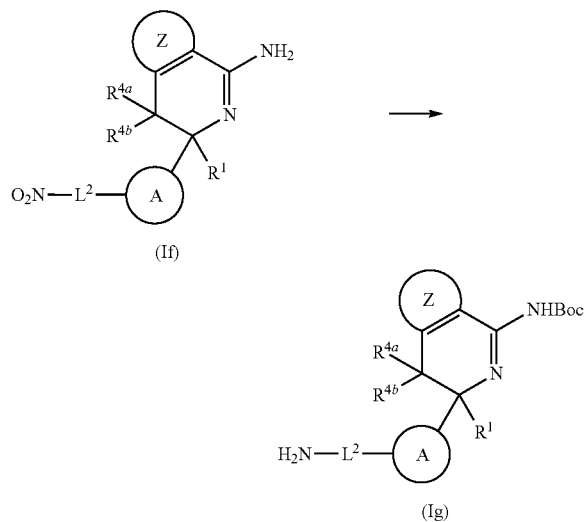

(If)

(Ig)

wherein Boc is t-butoxycarbonyl and other symbols are the same as defined above.

Compound (If) is suspended or dissolved in a solvent such as toluene, dichloromethane, dioxane, or tetrahydrofuran. To the mixture is added di-tert-butyl dicarbonate at a temperature between −40° C. and reflux temperature of the solvent, preferably −10 and 40° C. and reacted for 1 to 48 hours, preferably 1 to 30 hours. To the reaction solution are subsequently added methanol, distilled water, iron and ammonium chloride at a temperature between −40° C. and reflux temperature of the solvent, preferably −10 and 40° C. and reacted at a temperature between room temperature and reflux temperature of the solvent for 0.1 to 48 hours, preferably 0.5 to 6 hours to afford Compound (Ig).

An amino protecting group may be a substituent which can be protected and deprotected according to the methods in Protective Groups in Organic Synthesis, Theodora W Green (John Wiley & Sons) or the like and examples are lower alkoxycarbonyl, lower alkenyloxycarbonyl, trialkylsilyl, acyl, methanesulfonyl, trifluoroethanesulfonyl, and toluene sulfonyl.

Alternatively, a nitro group of amino-protected Compound (If) can be reduced by adding a catalytic reduction agent such as 10% palladium/carbon to amino-protected Compound (If) in tetrahydrofuran, ethyl acetate, methanol or the like and reacting in the range from atmospheric pressure to 5 atm, preferably atmospheric pressure and 2 atm under hydrogen atmosphere at a temperature between 30° C. to 120° C., preferably 50 to 80° C. for 0.5 to 48 hours, preferably 6 to 20 hours, or according to the methods in Comprehensive Organic Transformations, Richard C Larock (Mcgraw-Hill) or the like to afford Compound (Ig).

3) Synthesis of Compound (Ii)

[Chemical Formula 18]

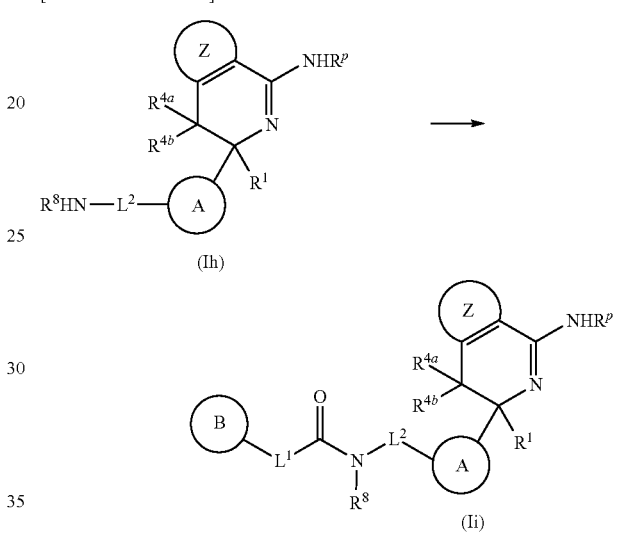

(Ih)

(Ii)

wherein Rp is an amino protecting group and other symbols are the same as defined above.

To a solution of Compound (Ih) in a solvent such as toluene, dichloromethane, dioxane, or tetrahydrofuran are added a carboxylic acid corresponding to the target compound, a base such as triethylamine or diisopropylethylamine, and a condensation agent such as O-(benzotriazol-1-yl)-N,N,N',N'-tetramethyluronium hexafluoro-phosphate, WSCD, or CDI at a temperature between −40° C. and reflux temperature of the solvent, preferably −10 and 40° C. The mixture is reacted at a temperature between −40° C. and reflux temperature of the solvent, preferably −10 and 40° C. for 0.1 and 48 hours, preferably 0.5 to 6 hours to afford Compound (Ii).

4) Synthesis of Compound (Ik)

[Chemical Formula 19]

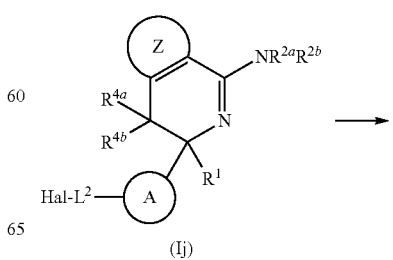

(Ij)

-continued

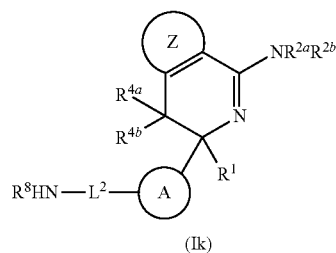

(Ik)

wherein Hal is halogen and each symbol is the same as defined above.

To a solution of Compound (Ij) with halogen on ring A in a solvent such as tetrahydrofuran, toluene or xylene are added trisdibenzylideneaceton dipalladium, palladium acetate, or palladium(0) prepared in the reaction system or the like and a phosphine ligand such as tri-tert-butylphosphine, or dicyclohexylbiphenyl phosphine. To the mixture is added a reagent such as lithium hexamethyldisilazide, or benzophenone imine which has a substituent corresponding to the target compound at a temperature between −10 and 30° C. and reacted at a temperature between 30° C. and reflux temperature of the solvent, preferably 50 and 100° C. for 0.5 to 48 hours, preferably 3 to 20 hours to afford Compound (Ik).

5) Synthesis of Compound (Im)

[Chemical Formula 20]

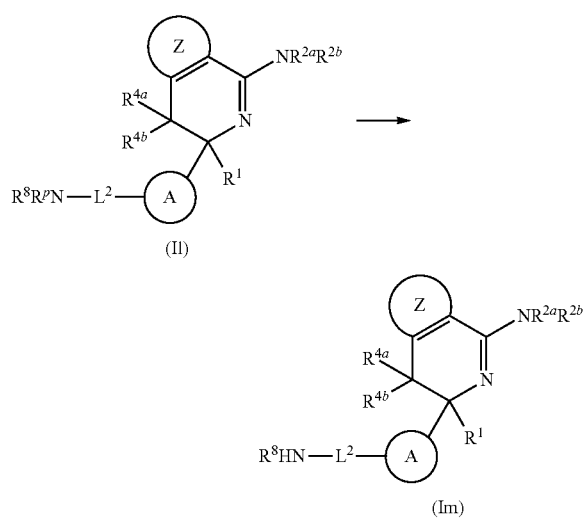

wherein $R^p$ is an amino protecting group, and each symbol is the same as defined above.

Compound (Im) can be obtained by deprotecting an amino protected Compound (Il) according to the method in Protective Groups in Organic Synthesis and Theodora W Greene (John Wiley & Sons) or the like.

Any substituent which can be deprotected by the method in Protective Groups in Organic Synthesis, Theodora W Green (John Wiley & Sons) or the like can be employed as an amino protecting group, for example, alkoxycarbonyl, alkenyloxycarbonyl, trialkylsilyl, acyl, methane sulfonyl, trifluoroethanesulfonyl, or toluenesulfonyl.

6) Synthesis of Compound (In)

Compound (In) can be prepared by Method A or Method B.

[Chemical Formula 21]

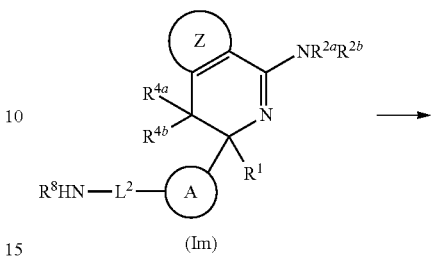

wherein and each symbol is the same as defined above.

Method A: Condensation Under Acidic Conditions

An aryl halide or a heteroaryl halide which is commercially available or can be prepared by known method (Tetrahedron, 2009, vol. 65, p. 757 to 764) or similar methods thereof is reacted with Compound (Im) in the presence of an acid such as hydrogen chloride, sulfuric acid, trifluoroacetic acid, methanesulfonic acid, trifluoromethanesulfonic acid, or perchloric acid in a solvent such as methanol, ethanol, isopropylalcohol, butanol, isobutanol, sec-butanol, acetic acid, water or a mixed solvent thereof at a temperature between 0° C. and reflux temperature of the solvent, preferably 20° C. and 140° C. for 0.1 to 120 hours, preferably 0.5 to 72 hours to afford Compound (In)

Method B: Condensation Under Basic Conditions

An aryl halide or a heteroaryl halide which is commercially available or can be prepared by known method (Tetrahedron, 2009, vol. 65, p. 757 to 764) or similar methods thereof is reacted with Compound (Im) in the presence of a base such as triethylamine, sodium carbonate, potassium carbonate, cesium carbonate, sodium methoxide, potassium tert-butoxide, n-butyllithium, lithium hexamethyldisilazide, sodium hexamethyldisilazide, or potassium hexamethyldisilazide in a solvent such as toluene, tetrahydrofuran, dimethylformamide, 1,2-dimethoxyethane, 1,4-dioxane, or methanol at a temperature between 0° C. and reflux temperature of the solvent, preferably 20° C. and 140° C. for 0.5 to 100 hours, preferably 0.5 to 72 hours to afford Compound (In).

Alternatively, the reaction can be subjected under the condition with trisdibenzylideneacetone dipalladium, palladium acetate or palladium (0) which is prepared in a reaction system and a phosphine ligand such as triphenylphosphine, tri-tert-butylphosphine, dicyclohexylbiphenylphosphine, 9,9-dimethyl-4,5-bis(diphenylphosphino)xanthene (Xantphos), 2-dicyclohexylphosphino-2',4',6'-triisopropylbiphenyl (X-Phos), 2-dicyclohexylphosphino-2',6'-diidopropoxy-1,1'-biphenyl (Ruphos). In this case, Compound (In) can be prepared by reacting under the microwave irradiation or unirradiated, at a temperature between 0° C. and 150° C., preferably 10° C. and 100° C. for 0.5 to 72 hours, preferably 1 to 24 hours.

7) Synthesis of Compound (Ip)

[Chemical Formula 22]

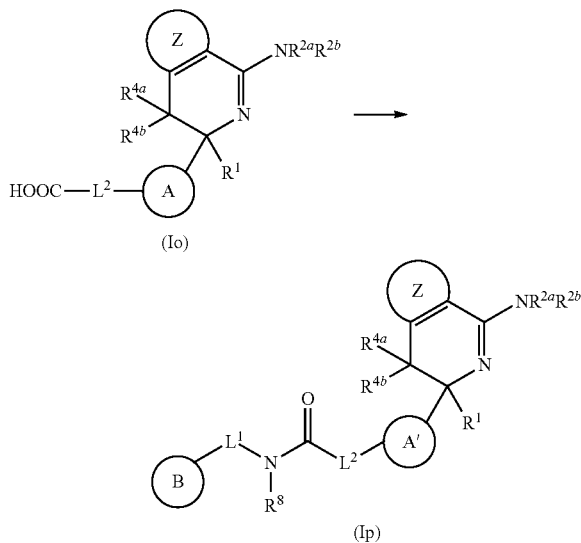

wherein each symbol is the same as defined above.

Compound (Io) with carboxy on ring A is reacted with a primary amine or secondary amine such as aniline, 2-aminopyridine, or dimethylamine with a substituent corresponding to the target compound in the presence of a dehydration-condensation agent such as dicyclohexylcarbodiimide, carbonyldiimidazole, or dicyclohexylcarbodiimide-N-hydroxybenzotriazole in a solvent such as dimethylformamide, tetrahydrofuran, or dichloromethane at a temperature between −80° C. and 100° C., preferably −20° C. and 40° C. for 0.1 to 24 hours, preferably 1 to 12 hours to afford Compound (Ip).

Optically active compounds of Compound (I) can be prepared from an optically active starting material, from an optically active intermediate obtained by asymmetry synthesis at a suitable stage, or by performing optical resolution of an intermediate or a target compound, each of which is a racemate, at a suitable stage. Examples of a method for optical resolution is separation of an optical isomer using an optically active column; kinetic optical resolution utilizing an enzymatic reaction; crystallization resolution of a diastereomer by salt formation using a chiral acid or a chiral base; and preferential crystallization method.

As specific embodiments of the compound (1) of the present invention, the following compounds are exemplified.

In the formula (I), for example, ring Z is substituted or unsubstituted pyridine or substituted or unsubstituted benzene.

Ring Z is, for example, pyridine optionally substituted with 0 to 3 substituents independently selected from halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted carbocyclyl, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted carbocyclylsulfinyl, substituted or unsubstituted carbocyclylsulfonyl, substituted or unsubstituted heterocyclyl, substituted or unsubstituted heterocyclyloxy, substituted or unsubstituted heterocyclylthio, substituted or unsubstituted heterocyclylalkyl, substituted or unsubstituted heterocyclylalkoxy, substituted or unsubstituted heterocyclyloxycarbonyl, substituted or unsubstituted heterocyclylsulfinyl or substituted or unsubstituted heterocyclylsulfonyl.

Ring Z is, for example, pyridine optionally substituted with 0 to 2 substituents independently selected from halogen, hydroxy, substituted or unsubstituted alkyl, substituted or unsubstituted alkenyl, substituted or unsubstituted alkoxy, substituted or unsubstituted alkenyloxy, substituted or unsubstituted alkylthio, substituted or unsubstituted alkenylthio, substituted or unsubstituted acyl, substituted or unsubstituted acyloxy, cyano, carboxy, substituted or unsubstituted alkoxycarbonyl, substituted or unsubstituted alkenyloxycarbonyl, substituted or unsubstituted amino, substituted or unsubstituted carbamoyl, substituted or unsubstituted carbocyclyl, substituted or unsubstituted carbocyclyloxy, substituted or unsubstituted carbocyclyloxycarbonyl, substituted or unsubstituted carbocyclylsulfinyl, substituted or unsubstituted heterocyclyl, substituted or unsubstituted heterocyclyloxy or substituted or unsubstituted heterocyclyloxycarbonyl.

Ring Z is, for example, pyridine optionally substituted with 0 to 2 substituents independently selected from halogen, hydroxy, substituted or unsubstituted alkyl, substituted or unsubstituted alkoxy, substituted or unsubstituted acyl, substituted or unsubstituted acyloxy, cyano, carboxy, substituted or unsubstituted alkoxycarbonyl or substituted or unsubstituted amino.

Ring Z is, for example, pyridine optionally substituted with 0 to 2 substituents independently selected from halogen, hydroxy, alkyl optionally substituted with one or more substituents selected from the substituent group α, alkoxy optionally substituted with one or more substituents selected from the substituent group α, acyl optionally substituted with one or more substituents selected from the substituent group α, acyloxy optionally substituted with one or more substituents selected from the substituent group α, cyano, carboxy, alkoxycarbonyl optionally substituted with one or more substituents selected from the substituent group α or amino optionally substituted with one or more substituents selected from the substituent group α.

As specific embodiments, the compounds of the following formulas (Ia) to (Ie):

[Chemical Formula 23]

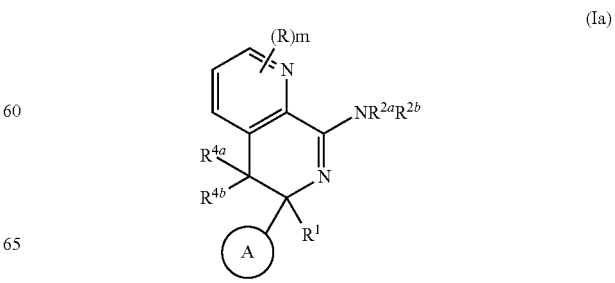

-continued
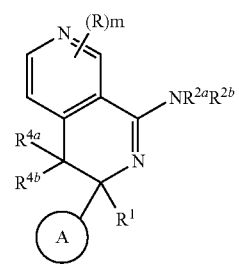 (Ib)
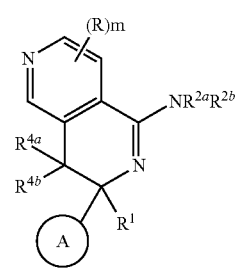 (Ic)
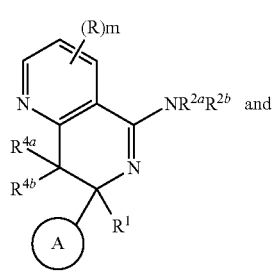 (Id) and
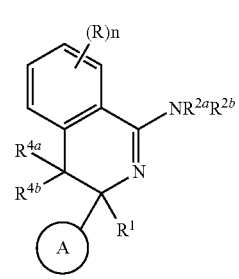 (Ie)
wherein each symbol is as follows are exemplified:
Ring A is, for example,
[Chemical Formula 24]
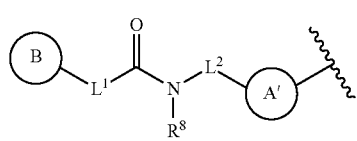
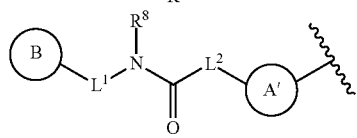
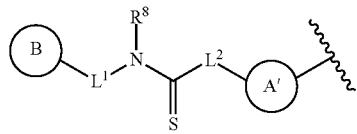
-continued
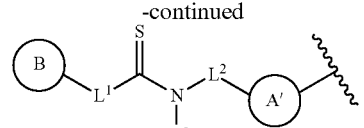
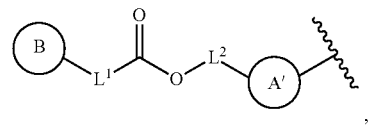
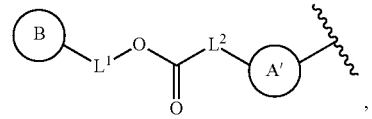
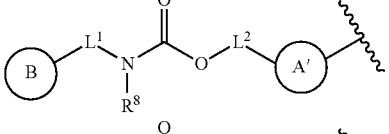
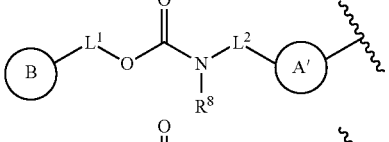
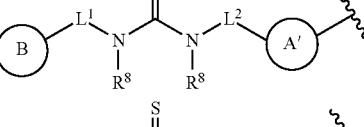
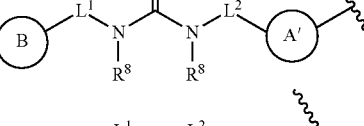
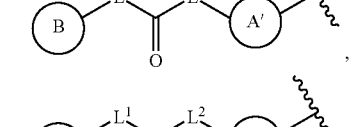
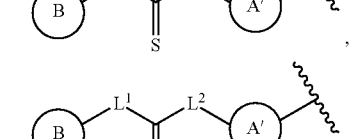
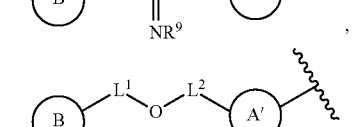
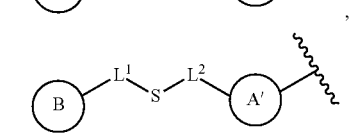
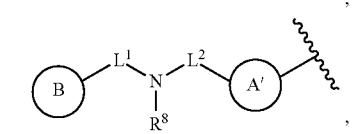
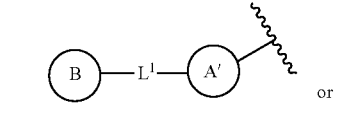 or

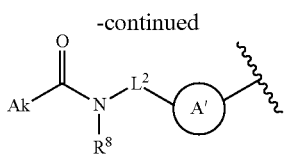

wherein each symbol is the same as defined above.

Ring A is, for example,

[Chemical Formula 25]

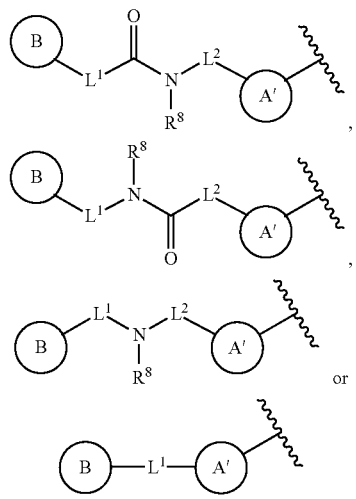

wherein each symbol is the same as defined above.

Ring A is, for example,

[Chemical Formula 26]

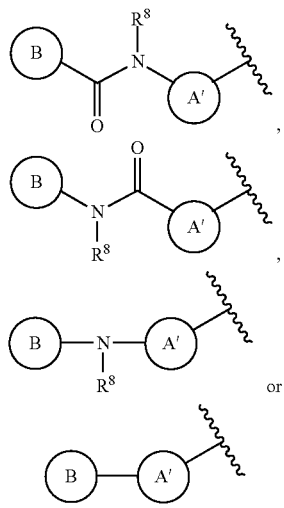

wherein each symbol is the same as defined above.

Ring A' is, for example, a substituted or unsubstituted carbocycle or a substituted or unsubstituted heterocycle.

Ring A' is, for example, substituted or unsubstituted benzene or substituted or unsubstituted pyridine. Examples of the substituent are one or more selected from halogen, cyano, alkyl and alkoxy.

Ring A' is, for example, substituted or unsubstituted benzene. Examples of the substituent are one or more selected from halogen, cyano, alkyl and alkoxy.

Ring B is, for example, a substituted or unsubstituted carbocycle or a substituted or unsubstituted heterocycle.

Ring B is, for example, substituted or unsubstituted pyridine, substituted or unsubstituted pyrimidine or substituted or unsubstituted pyrazine. Examples of the substituent are one or more substituents selected from halogen, cyano, alkyl, halogenoalkyl, alkoxy and alkynyloxy.

Ring B is, for example, substituted or unsubstituted pyridine or substituted or unsubstituted pyrazine. Examples of the substituent are one or more substituents selected from halogen, cyano, alkyl, halogenoalkyl, alkoxy and alkynyloxy.

$L^1$ and $L^2$ are, for example, each independently a bond, substituted or unsubstituted alkylene, substituted or unsubstituted alkenylene or substituted or unsubstituted alkynylene.

$L^1$ and $L^2$ are, for example, each independently a bond, substituted or unsubstituted alkylene.

Each of $L^1$ and $L^2$ is, for example, a bond.

R is, for example, each independently halogen, hydroxy, substituted or unsubstituted alkyl, substituted or unsubstituted alkenyl, substituted or unsubstituted alkoxy, substituted or unsubstituted alkenyloxy, substituted or unsubstituted alkylthio, substituted or unsubstituted alkenylthio, substituted or unsubstituted acyl, substituted or unsubstituted acyloxy, cyano, carboxy, substituted or unsubstituted alkoxycarbonyl, substituted or unsubstituted alkenyloxycarbonyl, substituted or unsubstituted amino, substituted or unsubstituted carbamoyl, substituted or unsubstituted carbocyclyl, substituted or unsubstituted carbocyclyloxy, substituted or unsubstituted carbocyclyloxycarbonyl, substituted or unsubstituted carbocyclylsulfinyl, substituted or unsubstituted heterocyclyl, substituted or unsubstituted heterocyclyloxy or substituted or unsubstituted heterocyclyloxycarbonyl, m is an integer of 0 to 3, and n is an integer of 0 to 4.

R is, for example, halogen, hydroxy, substituted or unsubstituted alkyl, substituted or unsubstituted alkoxy, substituted or unsubstituted acyl, substituted or unsubstituted acyloxy, cyano, carboxy, substituted or unsubstituted alkoxycarbonyl or substituted or unsubstituted amino, m or n is an integer of 0 to 2.

R is, for example, halogen, hydroxy, alkyl optionally substituted with one or more substituents selected from the substituent group α, alkoxy optionally substituted with one or more substituents selected from the substituent group α, acyl optionally substituted with one or more substituents selected from the substituent group α, acyloxy optionally substituted with one or more substituents selected from the substituent group α, cyano, carboxy, alkoxycarbonyl optionally substituted with one or more substituents selected from the substituent group α or amino optionally substituted with one or more substituents selected from the substituent group α, and m or n is an integer of 0 to 2.

R is, for example, halogen, hydroxy, alkyl, alkoxy, cyano, carboxy, alkoxycarbonyl or amino, and m or n is 1.

$R^1$ is, for example, substituted or unsubstituted alkyl, substituted or unsubstituted alkenyl, substituted or unsubstituted alkynyl, cyano, substituted or unsubstituted carbocyclyl or substituted or unsubstituted heterocyclyl.

$R^1$ is, for example, substituted or unsubstituted alkyl.

$R^1$ is, for example, unsubstituted having a carbon number of 1 to 3.

$R^{2a}$ and $R^{2b}$ are each independently hydrogen, substituted or unsubstituted alkyl or substituted or unsubstituted acyl.

$R^{2a}$ and $R^{2b}$ are, for example, both hydrogen.

$R^{4a}$ and $R^{4b}$ are each independently hydrogen, halogen, hydroxy, substituted or unsubstituted alkyl, substituted or unsubstituted alkenyl or substituted or unsubstituted alkynyl.

$R^{4a}$ and $R^{4b}$ are, for example, hydrogen.

Preferable combinations of the substituents of the compound (1) are, for example, the following 1) to 6):

1) The compound wherein ring Z is substituted or unsubstituted pyridine, ring A is

[Chemical Formula 27]

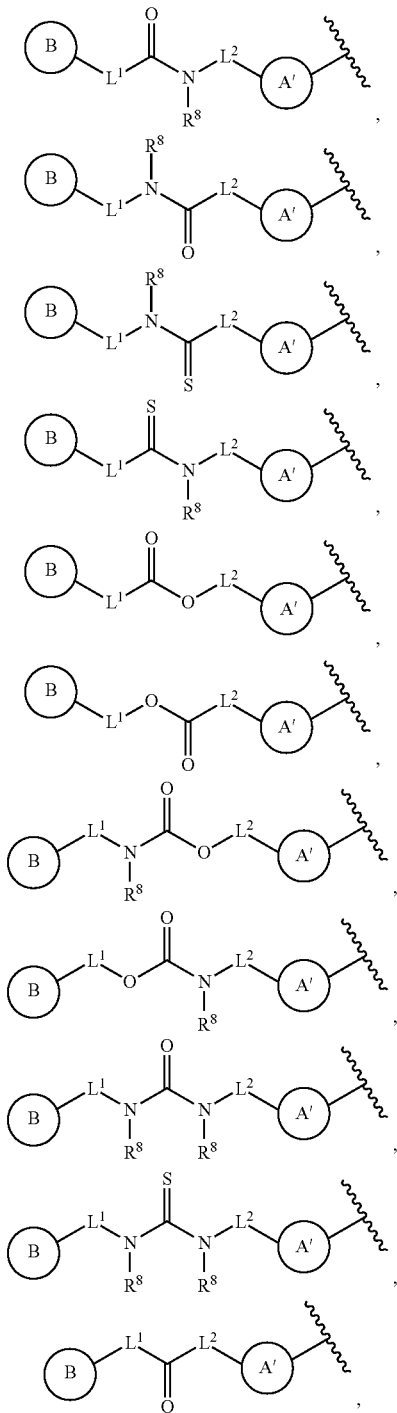

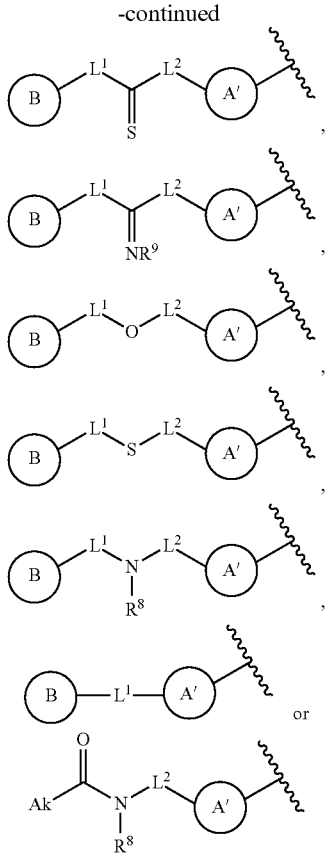

wherein ring A' and ring B are each independently a substituted or unsubstituted carbocycle or a substituted or unsubstituted heterocycle, $L^1$ and $L^2$ are each independently a bond, substituted or unsubstituted alkylene, substituted or unsubstituted alkenylene or substituted or unsubstituted alkynylene, $R^8$ is hydrogen, substituted or unsubstituted alkyl, substituted or unsubstituted alkenyl, substituted or unsubstituted alkynyl or substituted or unsubstituted acyl, $R^9$ is hydrogen, hydroxy, substituted or unsubstituted alkyl, substituted or unsubstituted alkenyl, substituted or unsubstituted alkynyl or substituted or unsubstituted acyl, and Ak is substituted or unsubstituted alkyl, substituted or unsubstituted alkenyl or substituted or unsubstituted alkynyl, $R^1$ is substituted or unsubstituted alkyl, and $R^{2a}$, $R^{2b}$, $R^{4a}$ and $R^{4b}$ are hydrogen.

2) The compound wherein ring Z is substituted or unsubstituted pyridine, ring A is

[Chemical Formula 28]

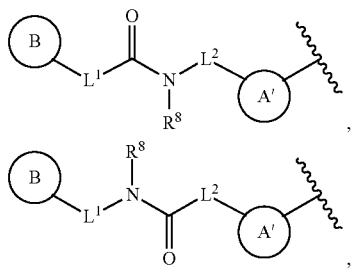

-continued

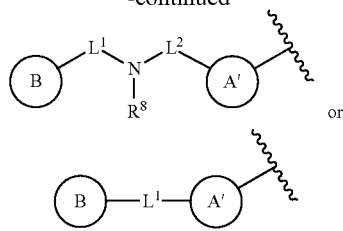

or

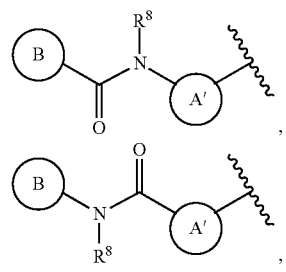

wherein ring A' and ring B are each independently a substituted or unsubstituted carbocycle or a substituted or unsubstituted heterocycle,
$L^1$ and $L^2$ are each independently a bond, substituted or unsubstituted alkylene or substituted or unsubstituted alkenylene, and $R^8$ is hydrogen,
$R^1$ is substituted or unsubstituted alkyl, and
$R^{2a}$, $R^{2b}$, $R^{4a}$ and $R^{4b}$ are hydrogen.

3) The compound wherein ring Z is substituted or unsubstituted pyridine, ring A is

[Chemical Formula 29]

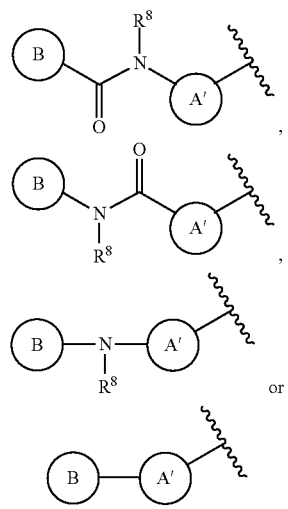

wherein ring A' and ring B are each independently a substituted or unsubstituted carbocycle or a substituted or unsubstituted heterocycle, and $R^8$ is hydrogen, $R^1$ is substituted or unsubstituted alkyl, and
$R^{2a}$, $R^{2b}$, $R^{4a}$ and $R^{4b}$ are hydrogen.

4) The compound wherein ring Z is substituted or unsubstituted pyridine, ring A is

[Chemical Formula 30]

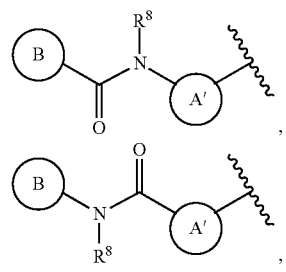

-continued

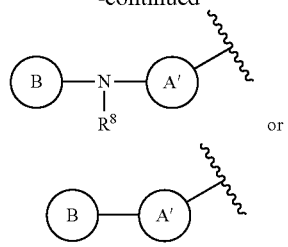

or wherein ring A' is substituted or unsubstituted benzene or substituted or unsubstituted pyridine, ring B is substituted or unsubstituted pyridine, substituted or unsubstituted pyrimidine or substituted or unsubstituted pyrazine, and $R^8$ is hydrogen,
$R^1$ is substituted or unsubstituted alkyl, and
$R^{2a}$, $R^{2b}$, $R^{4a}$ and $R^{4b}$ are hydrogen.

5) The compound wherein ring Z is pyridine optionally substituted with 0 to 2 substituents independently selected from halogen, hydroxy, alkyl optionally substituted with one or more substituents selected from the substituent group α, alkoxy optionally substituted with one or more substituents selected from the substituent group α, acyl optionally substituted with one or more substituents selected from the substituent group α, acyloxy optionally substituted with one or more substituents selected from the substituent group α, cyano, carboxy, alkoxycarbonyl optionally substituted with one or more substituents selected from the substituent group α or amino optionally substituted with one or more substituents selected from the substituent group α,
ring A is

[Chemical Formula 31]

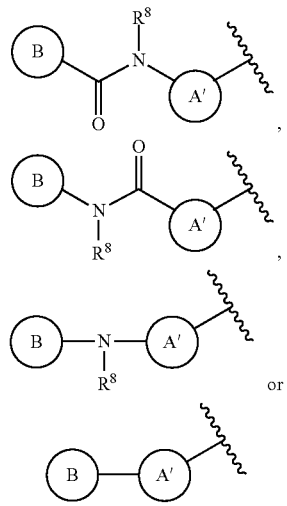

wherein ring A' is substituted or unsubstituted benzene or substituted or unsubstituted pyridine, wherein the substituent is one or more substituents selected from halogen, cyano, alkyl and alkoxy,
ring B is substituted or unsubstituted pyridine, substituted or unsubstituted pyrimidine or substituted or unsubstituted pyrazine, wherein the substituent is one or more substituents selected from halogen, cyano, alkyl, halogenoalkyl, alkoxy and alkynyloxy, and $R^8$ is hydrogen,
$R^1$ is substituted or unsubstituted alkyl, and
$R^{2a}$, $R^{2b}$, $R^{4a}$ and $R^{4b}$ are hydrogen.

6) The compound wherein ring Z is pyridine optionally substituted with halogen, ring A is

[Chemical Formula 32]

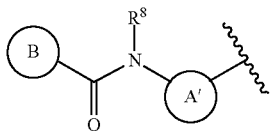

wherein ring A' is benzene optionally substituted with halogen,
ring B is substituted or unsubstituted pyridine or substituted or unsubstituted pyrazine, wherein the substituent is one or more substituents selected from halogen, cyano, alkyl, halogenoalkyl, alkoxy and alkynyloxy, and $R^8$ is hydrogen,
$R^1$ is unsubstituted alkyl, and
$R^{2a}$, $R^{2b}$, $R^{4a}$ and $R^{4b}$ are hydrogen.

The compounds of the present invention have BACE1 inhibitory activity, and therefore, are useful as a medicament for treatment, prevention, and/or symptom improvement of the diseases induced by the production, secretion or deposition of amyloid β protein such as dementia of the Alzheimer's type (Alzheimer's disease, senile dementia of Alzheimer type), Down's syndrome, memory impairment, prion disease (Creutzfeldt-Jakob disease), mild cognitive impairment (MCI), Dutch type of hereditary cerebral hemorrhage with amyloidosis, cerebral amyloid angiopathy, other type of degenerative dementia, mixed dementia such as coexist Alzheimer's disease with vascular type dementia, dementia with Parkinson's Disease, dementia with progressive supranuclear palsy, dementia with Cortico-basal degeneration, Alzheimer's disease with diffuse Lewy body disease, age-related macular degeneration, Parkinson's Disease and amyloid angiopathy.

The compound of the present invention has not only BACE1 inhibitory activity but the beneficialness as a medicament. The compound has any or all of the following superior properties.
a) Inhibitory activity for CYP enzymes such as CYP1A2, CYP2C9, CYP2C19, CYP2D6, or CYP3A4 of the compound is weak.
b) The compound show excellent pharmacokinetics such as high bioavailability or moderate clearance.
c) The compound has high metabolic stability.
d) The compound does not show irreversible inhibition to CYP enzyme such as CYP3A4 in the range of the concentration of the measurement conditions described in this description.
e) The compound does not show mutagenesis.
f) Risk of cardiovascular systems of the compound is low.
g) The compound show high solubility.
h) The compound show high brain distribution.
i) The compound has high oral absorption.
j) The compound has long half-life period.
k) The compound has high protein unbinding ratio.
l) The compound show negative in the Ames test.

Since the compound of the present invention has high inhibitory activity on BACE1 and/or high selectivity on other enzymes, it can be a medicament with reduced side effect. Further, since the compound has high effect of reducing amyloid β production in a cell system, particularly, has high effect of reducing amyloid β production in brain, it can be an excellent medicament. In addition, by converting the compound into an optically active compound having suitable stereochemistry, the compound can be a medicament having a wider safety margin on the side effect.

When a pharmaceutical composition of the present invention is administered, it can be administered orally or parenterally. The composition for oral administration can be administered in usual dosage forms such as tablets, granules, powders, capsules which can be prepared according to the conventional manners. The composition for parenteral administration can be administered suitably in usual parenteral dosage forms such as injections. Since the compounds of the present invention have high oral absorption, they can be preferably administered in an oral dosage form.

A pharmaceutical composition can be formulated by mixing various additive agents for medicaments, if needed, such as excipients, binders, disintegrating agents, and lubricants which are suitable for the formulations with an effective amount of the compound of the present invention.

Although the dosage of a pharmaceutical composition of the present invention should be determined in consideration of the patient's age and body weight, the type and degree of diseases, the administration route and the like, an usual oral dosage for an adult is 0.05 to 100 mg/kg/day and preferable is 0.1 to 10 mg/kg/day. For parenteral administration, although the dosage highly varies with administration routes, an usual dosage is 0.005 to 10 mg/kg/day and preferably 0.01 to 1 mg/kg/day. The dosage may be administered in one to several divisions per day.

The compound of the present invention can be used combining other medicaments for treating Alzheimer's disease such as an acetylcholinesterase inhibitor (hereinafter referred to as a concomitant medicament) for the purpose of enforcement of the activity of the compound or reduction of the amount of medication of the compound or the like. Under the present circumstances, timing of administration of the compound of the present invention and the concomitant medicament is not limited and these may be administered to the subject simultaneously or in a time proximity to each other. Furthermore, the compound of the present invention and concomitant medicament may be administered as two different compositions containing each active ingredient or as a single composition containing both active ingredient.

The dose of the concomitant medicament can be suitably selected on the basis of the dose used on clinical. Moreover, the mix ratio of the compound of the present invention and a concomitant medicament can be suitably selected in consideration of the subject of administration, administration route, target diseases, symptoms, combinations, etc. For example, when the subject of administration is human, the concomitant medicament can be used in the range of 0.01-100 parts by weight relative to 1 part by weight of the compound of the present invention.

Examples of a concomitant medicament are Donepezil hydrochloride, Tacrine, Galanthamine, Rivastigmine, Zanapezil, Memantine and Vinpocetine.

EXAMPLES

The present invention will be described in more detail with reference to, but not limited to, the following examples and test examples.

In this description, meanings of each abbreviation are as follows:
Me methyl
Et ethyl
Bz benzoyl
Boc t-butoxycarbonyl
THF tetrahydrofuran NMR analysis of each Example was performed by 300 MHz using DMSO-$d_6$ and $CDCl_3$.

$^1$H-NMR was measured using tetramethylsilane as an internal standard in deuterochloroform ($CDCl_3$) solvent. The δ values were shown by ppm and the coupling constant (J) were shown by Hz. In the data, s means singlet, d means doublet, t means triplet, m means multiplet, br means broad and brs means broad singlet.

"RT" in tables means retention time in LC/MS: liquid column chromatography/mass analysis, and these were measured under the conditions as mentioned below.

Compounds (I-1) to (I-10) and (I-27) to (I-34)
Column: XBridge C18 (5 μm, i.d.4.6×50 mm) (Waters)
Flow rate: 3 mL/min
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3 minutes was performed, and 100% solvent [B] was maintained for 1 minute.

Compounds (I-11) to (I-26)
Column: ACQUITY UPLC (registered trademark) BEH C18 (1.7 μm i.d.2.1×50 mm)
(Waters)
Flow rate: 0.8 mL/min
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3.5 minutes was performed, and 100% solvent [B] was maintained for 0.5 minute.

Example 1

Synthesis of Compound (I-5)

[Chemical Formula 33]

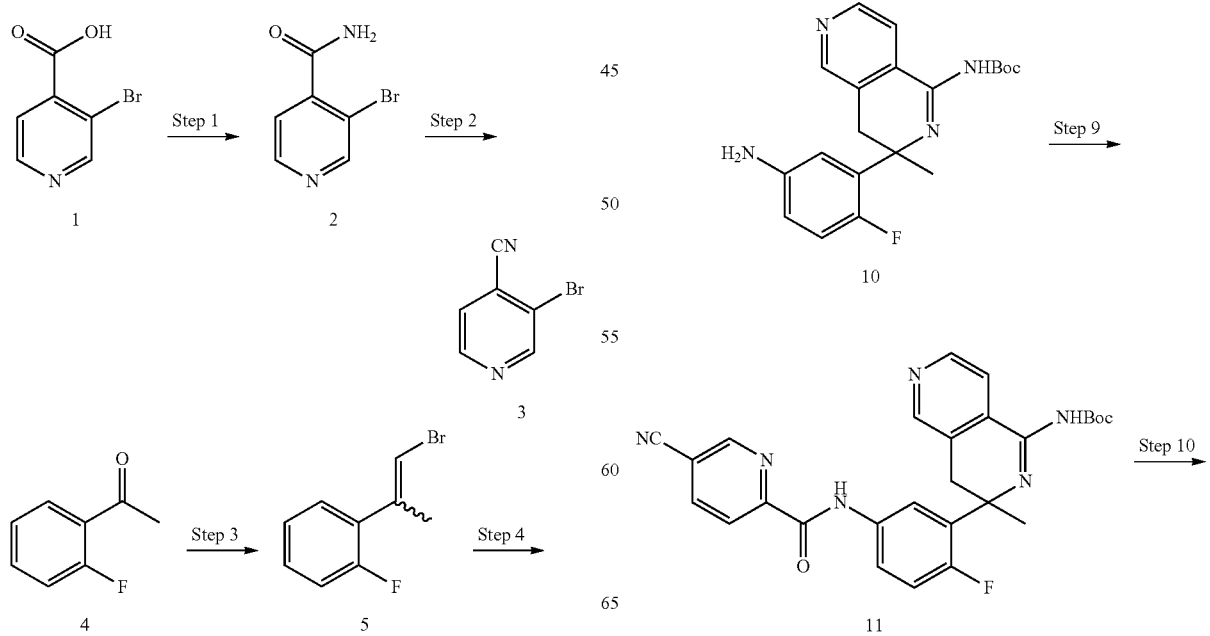

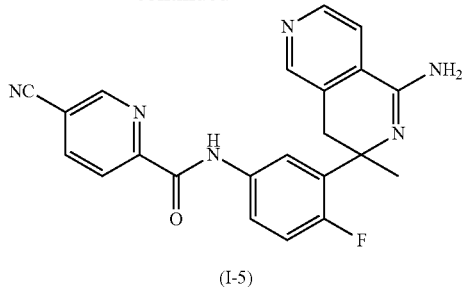

(I-5)

wherein a wavy line includes a cis isomer and a trans isomer about the double bond.

Step 1

To a suspension of 3-bromoisonicotinic acid (1) (4.0 g) in tetrahydrofuran (40 ml) were added oxalyl dichloride (1.82 ml) and dimethylformamide (one drop) at 0° C. and the mixture was stirred for 1 hour. To the reaction solution was added 28% aqueous ammonia (40 ml) and stirred for 40 minutes. After addition of ethyl acetate to the mixture, the organic layer was washed with brine and dried over magnesium sulfate. The solvent was evaporated under reduced pressure to afford Compound (2) (3.38 g).

$^1$H-NMR (DMSO-$d_6$) δ: 7.44 (1H, d, J=4.5 Hz), 7.83 (1H, s), 8.08 (1H, s), 8.60 (1H, d, J=4.5 Hz), 8.79 (1H, s).

Step 2

To a suspension of Compound (2) (3.05 g) in dichloromethane (60 ml), were added triethylamine (6.31 ml) and trifluoroacetic anhydride (2.57 ml) at 0° C. and the mixture was stirred for 1 hour. After addition of water and dichloromethane to the mixture, the organic layer was washed with brine and dried over magnesium sulfate. The solvent was evaporated under reduced pressure and the obtained residue was purified by chromatography to afford Compound (3) (2.61 g).

$^1$H-NMR (CDCl$_3$) δ: 7.55 (1H, d, J=4.5 Hz), 8.71 (1H, d, J=4.5 Hz), 8.94 (1H, s).

Step 3

To a suspension of (bromomethyl)triphenylphosphonium bromide (7.58 g) in tetrahydrofuran (20 ml) was added potassium-t-butoxide (17.4 ml, 1.0 M tetrahydrofuran solution) at 0° C. and stirred for 10 minutes. To the reaction solution was added a solution of 2-fluoroacetophenone (2)(1.79 ml) in tetrahydrofuran (20 ml) at 0° C. and stirred for 1.5 hours. After addition of an aqueous saturated ammonium chloride and ether to the reaction solution, the organic layer was washed with water and brine and dried over magnesium sulfate. The solvent was evaporated under reduced pressure and the obtained residue was purified by chromatography to afford Compound (5)(1.57 g).

$^1$H-NMR (CDCl$_3$) δ: 2.10 (d, J=1.5 Hz) and 2.19 (t, J=1.4 Hz) (3H), 6.32 (q, J=1.5 Hz) and 6.39 (q, J=1.4 Hz) (1H), 7.01-7.34 (4H, m).

Step 4

To a solution of Compound (5)(2.24 g) in dioxane (45 ml) were added bis(pinacolate)diboron (3.97 g), potassium acetate (3.07 g) and a [1,1'-bis(diphenylphosphino)ferrocene]palladium(II)dichloride dichloromethane complex (1:1) (425 mg) at room temperature. The mixture was stirred at 65° C. for 18 hours and filtered. The solvent was evaporated under reduced pressure and the obtained residue was purified by chromatography to afford Compound (6)(2.15 g).

$^1$H-NMR (CDCl$_3$) δ: 1.09 (s) and 1.31 (s) (12H), 2.18 (br s) and 2.37 (t, J=1.2 Hz) (3H), 5.53 (s) and 5.61 (q, J=1.2 Hz) (1H), 6.95-7.09 (2H, m), 7.14-7.30 (2H, m).

Step 5

To a solution of Compound (6)(267 mg) in tetrahydrofuran (8.0 ml) were added Compound (3)(205 mg), a 2M aqueous potassium carbonate solution (1.53 ml) and a [1,1'-bis(diphenyl phosphino)ferrocene]palladium(II)dichloride dichloromethane complex (1:1) (41.6 mg) at room temperature. The mixture was stirred at 70° C. for 14 hours and to the mixture were added subsequently water and ethyl acetate. The organic layer was washed with water and brine and dried over sodium sulfate. The solvent was evaporated under reduced pressure and the obtained residue was purified by chromatography to afford Compound (7)(203 mg).

$^1$H-NMR (CDCl$_3$) δ: 2.26 (t, J=1.2 Hz) and 2.32 (d, J=1.5 Hz) (3H), 6.75 (1H, br s), 6.97-7.56 (5H, m), 8.17 (s) and 8.88 (s) (1H), 8.42 (d, J=5.0 Hz) and 8.66 (d, J=5.0 Hz) (1H).

Step 6

To a suspension of ammonium chloride (1.44 g) in toluene (2.0 ml) was added trimethylaluminium (13.5 ml, 2.0 M toluene solution) at 0° C., and stirred at room temperature for 1 hour. To the reaction solution was added a solution of Compound (7)(184 mg) in toluene (4.0 ml) and stirred at 100° C. for 26 hours. To the reaction solution were added potassium sodium (+)-tartrate tetrahydrate (10.1 g) and a 2 M aqueous sodium hydroxide solution (15.4 ml) at 0° C., and stirred at room temperature for 1 hour. Chloroform was added, and the organic layer was washed with water and brine and dried over sodium sulfate. The solvent was evaporated under reduced pressure and the residue was purified by chromatography to afford Compound (8)(190 mg).

$^1$H-NMR (CDCl$_3$) δ: 2.22 (t, J=1.3 Hz) and 2.26 (d, J=1.5 Hz) (3H), 6.65-6.66 (1H, m), 6.87-7.40 (5H, m), 8.01 (s) and 8.71 (s) (1H), 8.35 (J=5.0 Hz) and 8.58 (d, J=4.9 Hz) (1H).

Step 7

Compound (8)(179 mg) was dissolved in sulfuric acid (1.0 ml) and stirred at room temperature for 14.5 hours. To the reaction solution was added nitric acid (62 μl) at 0° C. and the mixture was stirred for 1 hour. After the reaction solution was poured into ice, a 2M aqueous sodium hydroxide solution (18.0 ml) was added. To the reaction solution were subsequently added an aqueous saturated sodium hydrogen carbonate solution and ethyl acetate. The organic layer was washed with water and brine and dried over sodium sulfate. The solvent was evaporated under reduced pressure and the residue was purified by chromatography to afford Compound (9)(181 mg).

$^1$H-NMR (CDCl$_3$) δ: 1.53 (3H, s), 3.18 (1H, d, J=15.9 Hz), 3.30 (1H, d, J=15.9 Hz), 7.15 (1H, dd, J=10.9, 8.9 Hz), 7.31 (1H, d, J=5.0 Hz), 8.10 (1H, ddd, J=8.9, 4.0, 3.0 Hz), 8.55 (1H, s), 8.63 (1H, d, J=5.0 Hz), 8.68 (1H, dd, J=7.0, 3.0 Hz).

Step 8

To a suspension of Compound (9)(156 mg) in tetrahydrofuran (2.3 ml) was added di-tert-butyl dicarbonate (120 μl) at room temperature and stirred for 15 hours. To the reaction solution were added methanol (1.5 ml), distilled water (0.6 ml), iron (162 mg) and ammonium chloride (125 mg) at room temperature and stirred at 70° C. for 1.5 hours. After the reaction solution was filtered, were subsequently added water, an aqueous saturated sodium hydrogen carbonate solution, and ethyl acetate. The organic layer was washed with water and brine and dried over sodium sulfate. The solvent was evaporated under reduced pressure to afford Compound (10) (228 mg).

$^1$H-NMR (CDCl$_3$) δ: 1.60 (9H, s), 1.84 (3H, s), 3.19 (1H, d, J=16.0 Hz), 3.47 (2H, br s), 3.69 (1H, d, J=16.0 Hz), 6.32 (1H, dd, J=6.9, 2.7 Hz), 6.40-6.45 (1H, m), 6.78 (1H, dd, J=11.9, 8.5 Hz), 8.00 (1H, d, J=5.0 Hz), 8.42 (1H, s), 8.53 (1H, d, J=5.0 Hz), 10.55 (1H, br s).

Step 9

To a solution of Compound (10)(68.8 mg) in tetrahydrofuran (1.4 ml) were added 5-cyanopicolinic acid monohydrate (37.0 mg), triethylamine (67 μl), O-(benzotriazol-1-yl)-N,N,N',N'-tetramethyluronium hexafluorophosphate (92.0 mg) at 0° C. and stirred at room temperature for 1.5 hours. To the reaction solution were subsequently added an aqueous saturated sodium hydrogen carbonate solution and ethyl acetate. The organic layer was washed with water and brine and dried over sodium sulfate. The solvent was evaporated under reduced pressure and the obtained residue was purified by chromatography to afford Compound (11)(90.3 mg).

$^1$H-NMR (CDCl$_3$) δ: 1.63 (9H, s), 1.89 (3H, s), 3.27 (1H, d, J=15.9 Hz), 3.77 (1H, d, J=15.9 Hz), 7.07 (1H, dd, J=11.6, 8.9 Hz), 7.39 (1H, dd, J=7.2, 2.5 Hz), 7.73-7.79 (1H, m), 8.02 (1H, d, J=5.0 Hz), 8.19 (1H, dd, J=8.2, 2.0 Hz), 8.37 (1H, dd, J=8.2, 0.8 Hz), 8.50 (1H, s), 8.54 (1H, d, J=5.0 Hz), 8.88 (1H, dd, J=2.0, 0.8 Hz), 9.70 (1H, s), 10.72 (1H, s).

Step 10

Compound (11)(64.3 mg) was dissolved in formic acid (0.5 ml) and stirred at room temperature for 14 hours. To the reaction solution were subsequently added a 2M aqueous sodium hydroxide solution (6.49 ml), an aqueous saturated sodium hydrogen carbonate solution and ethyl acetate. The organic layer was washed with brine, dried over sodium sulfate and the solvent was evaporated under reduced pressure. The residue was purified by chromatography, solidified in methanol, ethyl acetate and n-hexane and filtered to afford Compound (12)(26.5 mg).

$^1$H-NMR (MeOD) δ: 1.75 (3H, s), 3.13 (1H, d, J=16.2 Hz), 3.62 (1H, d, J=16.2 Hz), 7.08 (1H, dd, J=11.9, 8.9 Hz), 7.64-7.70 (2H, m), 7.77 (1H, dd, J=7.4, 2.8 Hz), 8.34 (1H, dd, J=8.1, 1.0 Hz), 8.42 (1H, dd, J=8.1, 2.0 Hz), 8.46 (1H, s), 8.50 (1H, d, J=5.1 Hz), 9.04 (1H, d, J=1.5 Hz).

The following compounds are prepared in a similar manner to the above.

TABLE 1

| Compound No. | Structure | NMR (solvent: shift value ascending order) | MS [M + 1] | LC/MS RT |
|---|---|---|---|---|
| I-1 | 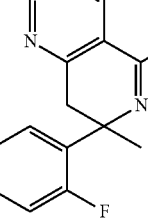 | 1H-NMR (DMSO-d6) δ: 1.47 (3H, s), 3.22 (1H, d, J = 15.2 Hz), 6.33 (2H, br s), 7.12 (1H, dd, J = 11.9, 8.9 Hz), 7.31 (1H, dd, J = 7.6, 5.1 Hz), 7.67-7.71 (1H, m), 7.97-8.05 (2H, br m), 8.26 (1H, d, J = 8.1 Hz), 8.45 (1H, dd, J = 4.6, 1.5 Hz), 8.57 (1H, dd, J = 8.1, 2.0 Hz), 9.18-9.19 (1H, m), 10.69 (1H, s). | 401 | 1.15 |
| I-2 | 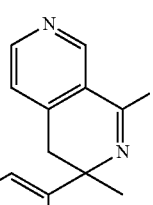 | 1H-NMR (MeOD) δ: 1.74 (3H, s), 3.17 (1H, d, J = 16.2 Hz), 3.61 (1H, d, J = 16.2 Hz), 7.05 (1H, dd, J = 12.2, 8.6 Hz), 7.33 (1H, d, J = 5.1 Hz), 7.61-7.65 (1H, m), 7.69 (1H, dd, J = 7.6, 2.5 Hz), 7.76-7.82 (1H, m), 8.48 (1H, d, J = 5.1 Hz), 8.51 (1H, d, J = 2.5 Hz), 8.87 (1H, s). | 412 | 1.14 |
| I-3 | 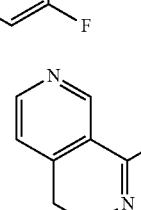 | 1H-NMR (MeOD) δ: 1.74 (3H, s), 3.17 (1H, d, J = 16.2 Hz), 3.61 (1H, d, J = 16.2 Hz), 7.06 (1H, dd, J = 12.2, 8.6 Hz), 7.33 (1H, d, J = 5.1 Hz), 7.62-7.66 (1H, m), 7.74 (1H, dd, J = 7.4, 2.8 Hz), 8.07 (1H, dd, J = 8.6, 2.5 Hz), 8.19 (1H, d, J = 9.1 Hz), 8.48 (1H, d, J = 5.1 Hz), 8.70 (1H, d, J = 2.0 Hz), 8.87 (1H, s). | 410 | 1.24 |
| I-4 | 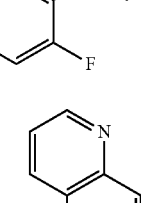 | 1H-NMR (MeOD) δ: 1.75 (3H, s), 3.27 (1H, d, J = 15.7 Hz), 3.63 (1H, d, J = 15.7 Hz), 7.08 (1H, dd, J = 12.2, 8.6 Hz), 7.39 (1H, dd, J = 7.6, 5.1 Hz), 7.67 (1H, d, J = 7.6 Hz), 7.72-7.78 (2H, m), 8.34 (1H, d, J = 8.1 Hz), 8.41-8.47 (2H, m), 9.04-9.05 (1H, m). | 401 | 1.2 |

TABLE 1-continued

| Compound No. | Structure | NMR (solvent: shift value ascending order) | MS [M + 1] | LC/MS RT |
|---|---|---|---|---|
| I-5 | 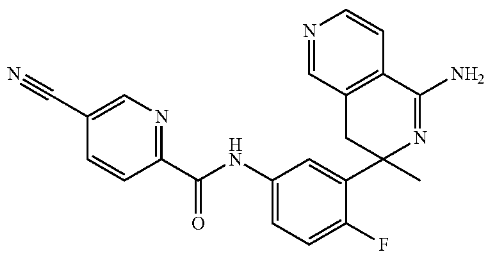 [SMILES: CC1(c2cc(NC(=O)c3ccc(C#N)cn3)ccc2F)Cc2cnccc2C(N)=N1] | 1H-NMR (MeOD) δ: 1.75 (3H, s), 3.13 (1H, d, J = 16.2 Hz), 3.62 (1H, d, J = 16.2 Hz), 7.08 (1H, dd, J = 11.9, 8.9 Hz), 7.64-7.70 (2H, m), 7.77 (1H, dd, J = 7.4, 2.8 Hz), 8.34 (1H, dd, J = 8.1, 1.0 Hz), 8.42 (1H, dd, J = 8.1, 2.0 Hz), 8.46 (1H, s), 8.50 (1H, d, J = 5.1 Hz), 9.04 (1H, d, J = 1.5 Hz). | 401 | 1.14 |
| I-6 | 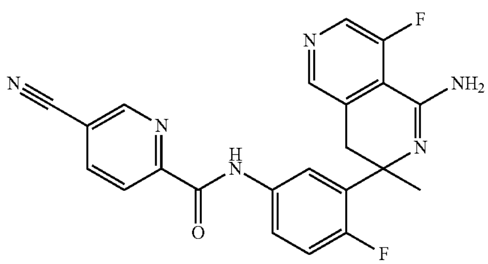 [SMILES: CC1(c2cc(NC(=O)c3ccc(C#N)cn3)ccc2F)Cc2cncc(F)c2C(N)=N1] | 1H-NMR (CD3OD) δ: 1.72 (3H, s). 3.10 (1H, d, J = 16.1 Hz), 3.60 (1H, d, J = 16.1 Hz), 7.08 (1H, dd, J = 11.8, 8.8 Hz), 7.66-7.71 (1H, m), 7.80 (1H, dd, J = 7.4, 2.7 Hz), 8.33-8.36 (2H, m), 8.41-8.44 (2H, m), 9.04-9.05 (1H, m). | 419 | 0.99 |

TABLE 2

| Compound No. | Structure | NMR (solvent: shift value ascending order) | MS [M + 1] | LC/MS RT |
|---|---|---|---|---|
| I-7 | 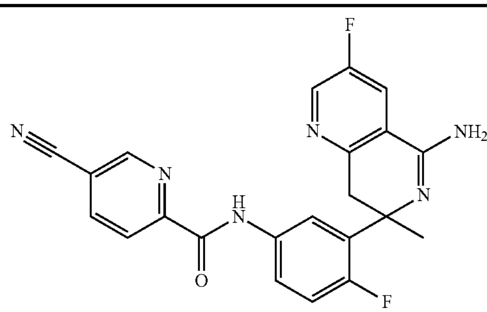 | 1H-NMR (MeOD) δ: 1.77 (3H, s), 3.26 (1H, d, J = 16.2 Hz), 3.74 (1H, d, J = 16.2 Hz), 7.08 (1H, dd, J = 11.9, 8.9 Hz), 7.63-7.67 (1H, m), 7.76 (1H, dd, J = 7.6, 2.5 Hz), 7.99 (1H, dd, J = 9.1, 2.5 Hz), 8.34 (1H, dd, J = 8.1, 1.0 Hz), 8.41-8.44 (2H, m), 9.04-9.05 (1H, m). | 419 | 1.09 |
| I-8 | 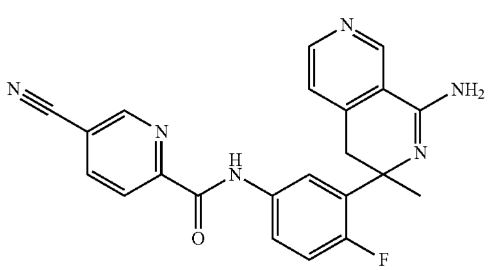 [SMILES: CC1(c2cc(NC(=O)c3ccc(C#N)cn3)ccc2F)Cc2ccncc2C(N)=N1] | 1H-NMR (DMSO-d6) δ: 1.44 (3H, s), 3.09 (1H, d, J = 15.2 Hz), 3.18 (1H, d, J = 15.2 Hz), 6.36 (2H, s), 7.11 (1H, dd, J = 11.9, 8.9 Hz), 7.29 (1H, d, J = 4.6 Hz), 7.68-7.71 (1H, m), 7.98-7.99 (1H, m), 8.26 (1H, d, J = 8.1 Hz), 8.47 (1H, d, J = 4.6 Hz), 8.57 (1H, dd, J = 8.1, 2.0 Hz), 8.82 (1H, s), 9.19 (1H, d, J = 2.0 Hz), 10.69 (1H, s). | 401 | 1.08 |
| I-9 | 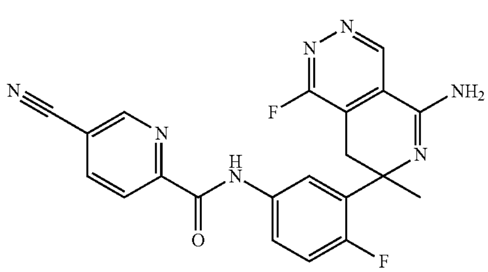 [SMILES: CC1(c2cc(NC(=O)c3ccc(C#N)cn3)ccc2F)Cc2c(cnnc2F)C(N)=N1] | 1H-NMR (MeOD) δ: 1.75 (3H, s), 3.02 (1H, d, J = 16.2 Hz), 3.78 (1H, d, J = 16.2 Hz), 7.08 (1H, dd, J = 11.7, 8.6 Hz), 7.64-7.68 (1H, m), 7.78 (1H, dd, J = 7.4, 2.8 Hz), 8.33 (1H, dd, J = 8.1, 1.0 Hz), 8.41 (1H, dd, J = 8.1, 2.0 Hz), 8.45 (1H, s), 8.74 (1H, s), 9.03-9.04 (1H, m). | 419 | 1.17 |

TABLE 2-continued

| Compound No. | Structure | NMR (solvent: shift value ascending order) | MS [M + 1] | LC/MS RT |
|---|---|---|---|---|
| I-10 | 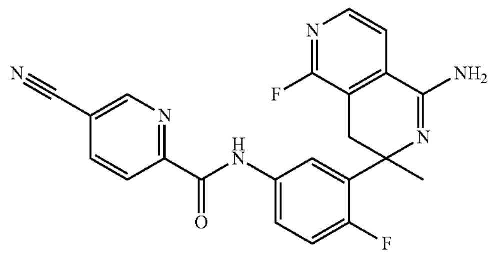 [SMILES: CC1(c2cc(NC(=O)c3ccc(C#N)cn3)ccc2F)Cc2c(ccnc2F)C(N)=N1] | 1H-NMR (MeOD) δ: 1.74 (3H, s), 3.01 (1H, d, J = 16.2 Hz), 3.66 (1H, d, J = 16.2 Hz), 7.09 (1H, dd, J = 11.9, 8.9 Hz), 7.60 (1H, d, J = 5.1 Hz), 7.64-7.67 (1H, m), 7.78 (1H, dd, J = 7.4, 2.8 Hz), 8.13 (1H, d, J = 5.1 Hz), 8.34 (1H, dd, J = 8.1, 1.0 Hz), 8.41 (1H, dd, J = 8.1, 2.0 Hz), 9.03-9.04 (1H, m). | 419 | 1.17 |
| I-11 | 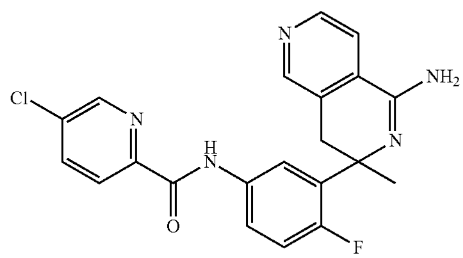 [SMILES: CC1(c2cc(NC(=O)c3ccc(Cl)cn3)ccc2F)Cc2cnccc2C(N)=N1] | | 410 | 1.23 |
| I-12 | 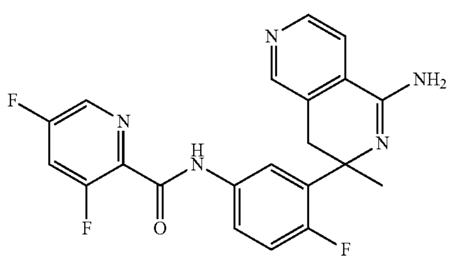 [SMILES: CC1(c2cc(NC(=O)c3ncc(F)cc3F)ccc2F)Cc2cnccc2C(N)=N1] | | 412 | 1.01 |

TABLE 3

| Compound No. | Structure | NMR (solvent: shift value ascending order) | MS [M + 1] | LC/MS RT |
|---|---|---|---|---|
| I-13 | 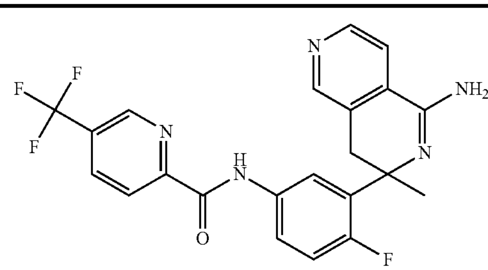 | | 444 | 1.36 |
| I-14 | 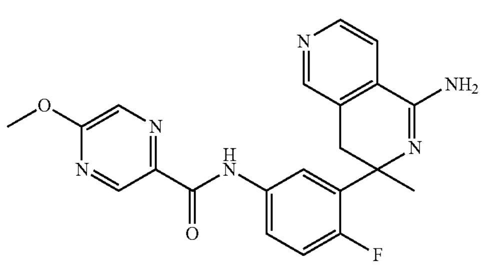 [SMILES: COc1cnc(C(=O)Nc2ccc(F)c(C3(C)Cc4cnccc4C(N)=N3)c2)cn1] | | 407 | 1.08 |

TABLE 3-continued

| Compound No. | Structure | NMR (solvent: shift value ascending order) | MS [M + 1] | LC/MS RT |
|---|---|---|---|---|
| I-15 | 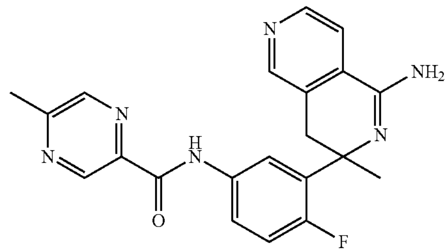 [SMILES: Cc1cnc(C(=O)Nc2ccc(F)c(C3(C)Cc4cnccc4C(N)=N3)c2)cn1] | | 391 | 0.97 |
| I-16 | 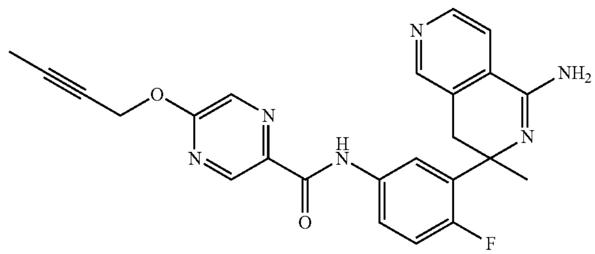 [SMILES: CC#CCOc1cnc(C(=O)Nc2ccc(F)c(C3(C)Cc4cnccc4C(N)=N3)c2)cn1] | | 445 | 1.34 |
| I-17 | 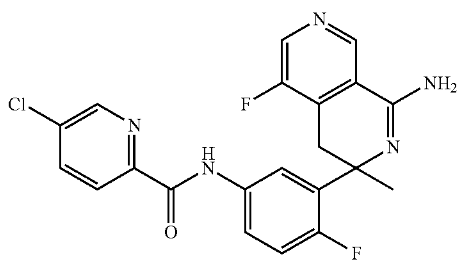 [SMILES: CC1(c2cc(NC(=O)c3ccc(Cl)cn3)ccc2F)Cc2c(F)cncc2C(N)=N1] | | 428 | 1.37 |
| I-18 | 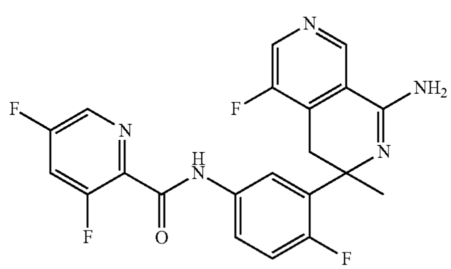 [SMILES: CC1(c2cc(NC(=O)c3ncc(F)cc3F)ccc2F)Cc2c(F)cncc2C(N)=N1] | | 430 | 1.18 |

TABLE 4

| Compound No. | Structure | NMR (solvent: shift value ascending order) | MS [M + 1] | LC/MS RT |
|---|---|---|---|---|
| I-19 | 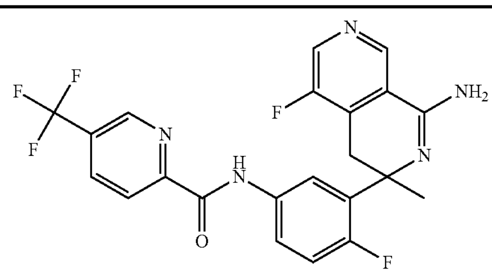 | | 462 | 1.47 |

TABLE 4-continued

| Compound No. | Structure | NMR (solvent: shift value ascending order) | MS [M + 1] | LC/MS RT |
|---|---|---|---|---|
| I-20 | 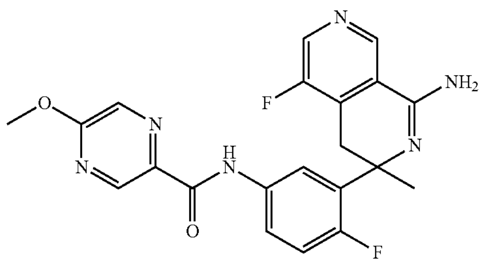 [SMILES: COc1cnc(C(=O)Nc2ccc(F)c(C3(C)Cc4c(F)cncc4C(N)=N3)c2)cn1] | | 425 | 1.23 |
| I-21 | 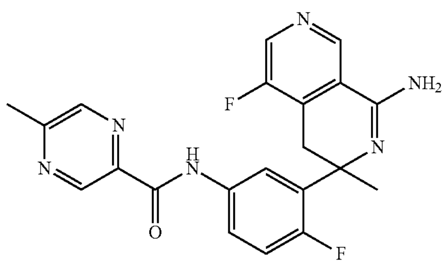 [SMILES: Cc1cnc(C(=O)Nc2ccc(F)c(C3(C)Cc4c(F)cncc4C(N)=N3)c2)cn1] | | 409 | 1.1 |
| I-22 | 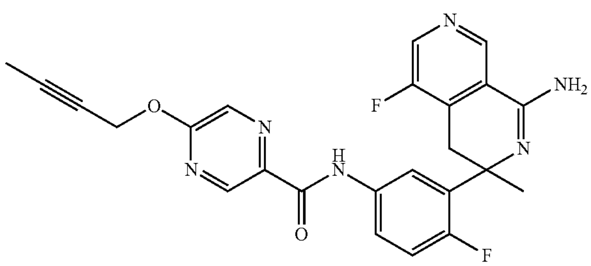 [SMILES: CC#CCOc1cnc(C(=O)Nc2ccc(F)c(C3(C)Cc4c(F)cncc4C(N)=N3)c2)cn1] | | 463 | 1.46 |
| I-23 | 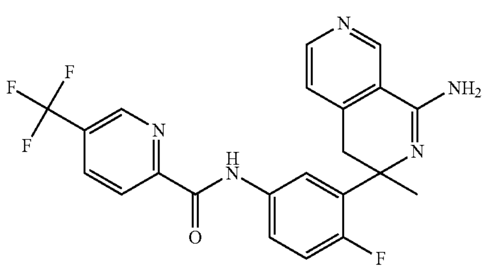 [SMILES: CC1(c2cc(NC(=O)c3ccc(C(F)(F)F)cn3)ccc2F)Cc2ccncc2C(N)=N1] | | 444 | 1.36 |

TABLE 5

| Compound No. | Structure | NMR (solvent: shift value ascending order) | MS [M + 1] | LC/MS RT |
|---|---|---|---|---|
| I-24 | 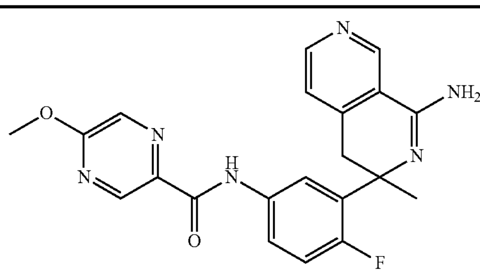 | | 407 | 1.11 |

TABLE 5-continued

| Compound No. | Structure | NMR (solvent: shift value ascending order) | MS [M + 1] | LC/MS RT |
|---|---|---|---|---|
| I-25 | 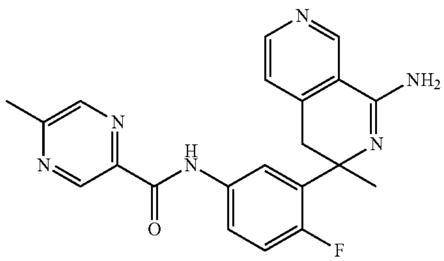 [SMILES: Cc1cnc(C(=O)Nc2ccc(F)c(C3(C)Cc4ccncc4C(N)=N3)c2)cn1] | | 391 | 0.98 |
| I-26 | 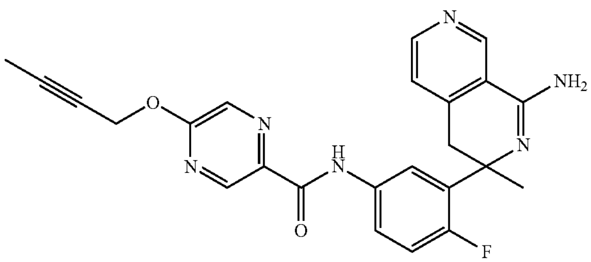 [SMILES: CC#CCOc1cnc(C(=O)Nc2ccc(F)c(C3(C)Cc4ccncc4C(N)=N3)c2)cn1] | | 445 | 1.36 |
| I-27 | 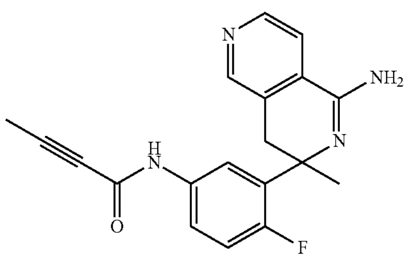 [SMILES: CC#CC(=O)Nc1ccc(F)c(C2(C)Cc3cnccc3C(N)=N2)c1] | ¹H-NMR (MeOD) δ: 1.70 (3H, s), 2.02 (3H, s), 3.08 (1H, d, J = 15.7 Hz), 3.56 (1H, d, J = 15.7 Hz), 6.97 (1H, dd, J = 11.9, 8.9 Hz), 7.38-7.40 (1H, m), 7.46 (1H, dd, J = 7.4, 2.8 Hz), 7.66 (1H, d, J = 5.1 Hz), 8.41 (1H, s), 8.49 (1H, d, J = 5.1 Hz). | 337 | 0.87 |
| I-28 | 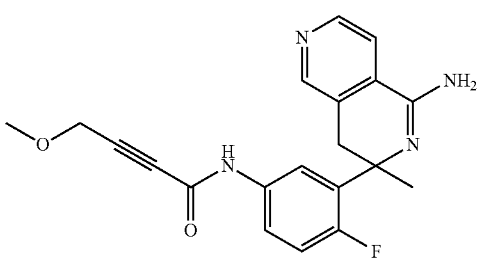 | ¹H-NMR (MeOD) δ: 1.72 (3H, s), 3.10 (1H, d, J = 15.7 Hz), 3.44 (3H, s), 3.58 (1H, d, J = 15.7 Hz), 4.30 (2H, s), 6.99 (1H, dd, J = 11.9, 8.9 Hz), 7.41-7.45 (1H, m), 7.50 (1H, dd, J = 7.1, 2.5 Hz), 7.67 (1H, d, J = 5.1 Hz), 8.43 (1H, s), 8.51 (1H, d, J = 5.1 Hz). | 367 | 0.82 |
| I-29 | 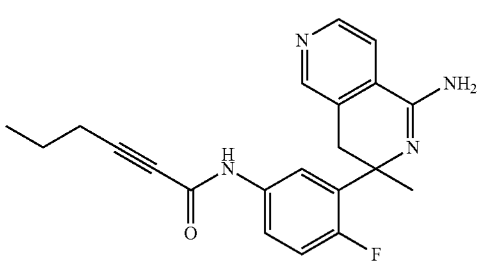 [SMILES: CCCC#CC(=O)Nc1ccc(F)c(C2(C)Cc3cnccc3C(N)=N2)c1] | ¹H-NMR (MeOD) δ: 1.07 (3H, t, J = 7.4 Hz), 1.60-1.69 (2H, m), 1.71 (3H, s), 2.38 (2H, t, J= 7.1 Hz), 3.08 (1H, d, J = 15.7 Hz), 3.56 (1H, d, J = 15.7 Hz), 6.97 (1H, dd, J = 11.9, 8.9 Hz), 7.39-7.43 (1H, m), 7.47 (1H, dd, J = 7.1, 2.5 Hz), 7.67 (1H, d, J = 5.1 Hz), 8.42 (1H, s), 8.50 (1H, d, J = 5.1 Hz). | 365 | 1.07 |

TABLE 6

| Compound No. | Structure | NMR (solvent: shift value ascending order) | MS [M + 1] | LC/MS RT |
|---|---|---|---|---|
| I-30 | 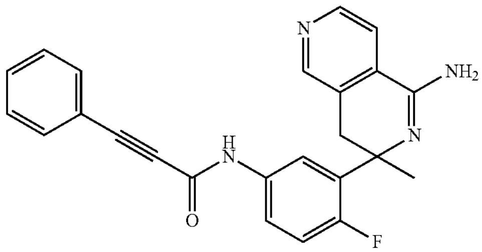 [SMILES: CC1(c2cc(NC(=O)C#Cc3ccccc3)ccc2F)Cc2cnccc2C(N)=N1] | ¹H-NMR (MeOD) δ: 1.74 (3H, s), 3.11 (1H, d, J = 15.7 Hz), 3.60 (1H, d, J = 15.7 Hz), 7.02 (1H, dd, J = 11.9, 8.9 Hz), 7.44-7.56 (5H, m), 7.63-7.65 (2H, m), 7.69 (1H, d, J = 5.1 Hz), 8.45 (1H, s), 8.52 (1H, d, J = 5.1 Hz). | 399 | 1.19 |
| I-31 | 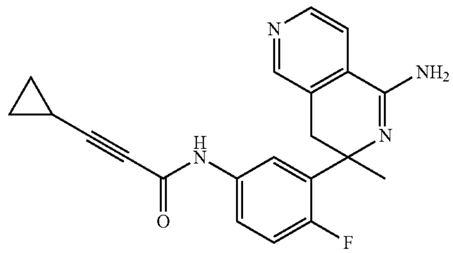 [SMILES: CC1(c2cc(NC(=O)C#CC3CC3)ccc2F)Cc2cnccc2C(N)=N1] | ¹H-NMR (MeOD) δ: 0.82-0.86 (2H, m), 0.94-0.99 (2H, m), 1.42-1.48 (1H, m), 1.68 (3H, s), 3.05 (1H, d, J = 15.7 Hz), 3.54 (1H, d, J = 15.7 Hz), 6.94 (H, dd, J = 11.7, 8.6 Hz), 7.35-7.39 (1H, m), 7.43 (1H, dd, J = 7.4, 2.8 Hz), 7.64 (1H, d, J = 5.1 Hz), 8.39 (1H, s), 8.47 (1H, d, J = 5.1 Hz). | 363 | 0.95 |
| I-32 | 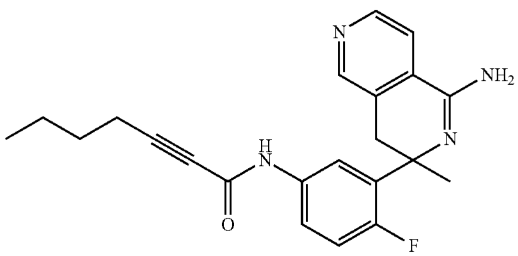 [SMILES: CCCCC#CC(=O)Nc1ccc(F)c(C2(C)Cc3cnccc3C(N)=N2)c1] | ¹H-NMR (MeOD) δ: 0.95 (3H, t, J = 7.1 Hz), 1.43-1.52 (2H, m), 1.55-1.62 (2H, m), 1.69 (3H, s), 2.39 (2H, t, J = 7.1 Hz), 3.06 (1H, d, J = 15.7 Hz), 3.54 (1H, d, J = 15.7 Hz), 6.95 (1H, dd, J = 12.2, 8.6 Hz), 7.37-7.40 (1H, m), 7.45 (1H, dd, J = 7.6, 2.5 Hz), 7.64 (1H, d, J = 5.1 Hz), 8.40 (1H, s), 8.47 (1H, d, J = 5.1 Hz). | 379 | 1.19 |
| I-33 | 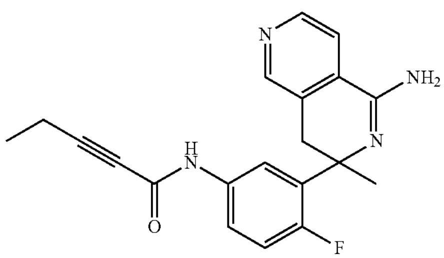 [SMILES: CCC#CC(=O)Nc1ccc(F)c(C2(C)Cc3cnccc3C(N)=N2)c1] | ¹H-NMR (MeOD) δ: 1.21 (3H, t, J = 7.6 Hz), 1.69 (3H, s), 2.39 (2H, q, J = 7.6 Hz), 3.06 (1H, d, J = 15.7 Hz), 3.54 (1H, d, J = 15.7 Hz), 6.95 (1H, dd, J = 11.9, 8.9 Hz), 7.37-7.41 (1H, m), 7.45 (1H, dd, J = 7.6, 2.5 Hz), 7.64 (1H, d, J = 5.1 Hz), 8.39 (1H, s), 8.47 (1H, d, J = 5.1 Hz). | 351 | 0.9 |
| I-34 | 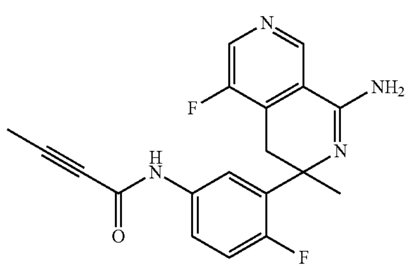 [SMILES: CC#CC(=O)Nc1ccc(F)c(C2(C)Cc3c(F)cncc3C(N)=N2)c1] | ¹H-NMR (MeOD) δ: 1.75 (3H, s), 2.01 (3H, s), 3.03 (1H, d, J = 16.7 Hz), 3.79 (1H, d, J = 16.7 Hz), 7.00 (1H, dd, J = 12.2, 8.6 Hz), 7.34-7.38 (1H, m), 7.52 (1H, dd, J = 7.6, 2.5 Hz), 8.49 (1H, s), 8.76 (1H, s). | 355 | 0.93 |

Test Examples of compounds of the present invention are described below.

Test Example 1

Assay of BACE1 Inhibitory Activity 48.5 μL of substrate peptide solution (Biotin-XSEVNLDAEFRHDSGC-Eu: X=ε-amino-n-capronic acid, Eu=Europium cryptate) was added to each well of 96-hole half-area plate (a black plate: Costar), and after addition of 0.5 μl of the compound of the present invention (N,N'-dimethylformamide solution) and 1 μl of Recombinant human BACE1 (R&D Systems), the reaction mixture was incubated at 30° C. for 3 hours. The substrate peptide was synthesized by reacting Cryptate TBPCOOH mono SMP (CIS bio international) with Biotin-XSEVNLDAEFRHDSGC (Peptide Institute, Inc.). The final concentrations of the substrate peptide and Recombinant human BACE1 were adjusted to 18 nmol/L and 7.4 nmol/L, respectively, and the reaction was performed in sodium acetate buffer (50 mmol/L sodium acetate, pH 5.0, 0.008% Triton X-100). After the incubation for reaction, 50 µl of 8.0 µg/ml Streptavidin-XL665 (CIS bio international) dissolved in phosphate buffer (150 mmol/L $K_2HPO_4$—KH2PO$_4$, pH 7.0, 0.008% Triton X-100, 0.8 mol/L KF) was added to each well and left stand at 30° C. for 1 hour. After then, fluorescence intensity was measured (excitation wavelength: 320 nm, measuring wavelength: 620 nm and 665 nm) using Wallac 1420 multilabel counter (Perkin Elmer life sciences). Enzymatic activity was determined from counting ratio of each wavelength (10,000×Count 665/Count 620) and 50% inhibitory concentration against the enzymatic activity ($IC_{50}$) was calculated.

Compound I-1: $IC_{50}$ 0.054 µmol/L
Compound I-27: $IC_{50}$ 0.308 µmol/L
Compound I-30: $IC_{50}$ 0.147 µmol/L Compounds I-2 to 26, 33 and 34 showed the $IC_{50}$ values of 1 µmol/L or less and Compounds I-28, 29, 31 and 32 showed 3 µmol/L or less.

Test Example 2

Measurement of β-Amyloid (Aβ) Production Inhibiting Effect in Cell

Neuroblastoma SH-SY5Y cells (SH/APPwt) with human wild-type 13-APP excessively expressed therein were prepared at 8×10$^5$ cells/mL, and 150 µl portions thereof were inoculated into each well of a 96-well culture plate (Falcon). The cells were cultured for 2 hours at 37° C. in a 5% gaseous carbon dioxide incubator. Then, a solution which have been preliminarily prepared by adding and suspending the compound of the present invention (DMSO (dimethyl sulfoxide) solution) so as to be 2 µl/50 µl medium was added to the cell sap. Namely, the final DMSO concentration was 1%, and the amount of the cell culture was 200 µl. After the incubation was performed for 24 hours from the addition of the test compound, 100 µl of the culture supernatant was collected from each fraction. The amount of the Aβ in each fraction was measured.

The Aβ amount was measured as follows. 10 µl of a homogeneous time resolved fluorescence (HTRF) measurement reagent (Amyloid β1-40 peptide; IBA Molecular Holding, S.A.) and 10 µl of the culture supernatant were put into a 384-well half area microplate (black microplate, Costar) and mixed with each other, and then left standing overnight at 4° C. while the light was shielded. Then, the fluorescence intensity (excitation wavelength: 337 nm, measurement wavelength: 620 nm and 665 nm) was measured with Wallac 1420 multilabel counter (Perkin Elmer life sciences). The Aβ amount was determined from the count rate at each measurement wavelength (10000×Count 665/Count 620), and the amount needed to inhibit A6 production by 50% ($IC_{50}$) was calculated from at least six different dosages.

Compound I-7: $IC_{50}$ 0.002 µmol/L
Compound I-30: $IC_{50}$ 0.046 µmol/L
Compound I-34: $IC_{50}$ 0.020 µmol/L Compounds I-1 to 6, 8 to 21, 23 to 27 and 29 to 34 showed the $IC_{50}$ value of 1 µmol/L or less and Compound I-28 showed 3 µmol/L or less.

Test Example 3

Lowering Effect on Brain β Amyloid in Rats

Compound of the present invention is suspended in 0.5% methylcellulose, the final concentration is adjusted to 2 mg/mL, and this is orally administered to male Crj:SD rat (7 to 9 weeks old) at 10 mg/kg. In a vehicle control group, only 0.5% methylcellulose is administered, and an administration test is performed at 3 to 8 animals per group. A brain is isolated 3 hours after administration, a cerebral hemisphere is isolated, a weight thereof is measured, the hemisphere is rapidly frozen in liquid nitrogen, and stored at –80° C. until extraction date. The frozen cerebral hemisphere is transferred to a homogenizer manufactured by Teflon (registered trade mark) under ice cooling, a 5-fold volume of a weight of an extraction buffer (containing 1% CHAPS ({3-[(3-chloroamidopropyl)dimethylammonio]-1-propanesulfonate}), 20 mmol/L Tris-HCl (pH 8.0), 150 mmol/L NaCl, Complete (Roche) protease inhibitor) is added, up and down movement is repeated, and this is homogenized to solubilize for 2 minutes. The suspension is transferred to a centrifugation tube, allowed to stand on an ice for 3 hours or more and, thereafter centrifuged at 100,000×g, 4° C. for 20 minutes. After centrifugation, the supernatant is transferred to an ELISA plate (product No. 294-62501, Wako Junyaku Kogyo) for measuring β amyloid 40. ELISA measurement is performed according to the attached instruction. The lowering effect is calculated as a ratio compared to the brain β amyloid 40 level of vehicle control group of each test.

Test Example 4

CYP3A4 Fluorescent MBI Test

The CYP3A4 fluorescent MBI test is a test of investigating enhancement of CYP3A4 inhibition of the compound of the present invention by a metabolism reaction. 7-benzyloxytrifluoromethylcoumarin (7-BFC) is debenzylated by the CYP3A4 enzyme (enzyme expressed in *Escherichia coli*) and a metabolite, 7-hydroxytrifluoromethylcoumarin (7-HFC) which emits fluorescent light is produced. The test is performed using 7-HFC production reaction as an index.

The reaction conditions are as follows: substrate, 5.6 µmol/L 7-BFC: pre-reaction time, 0 or 30 minutes; reaction time, 15 minutes; reaction temperature, 25° C. (room temperature); CYP3A4 content (expressed in *Escherichia coli*), at pre-reaction 62.5 µmol/mL, at reaction 6.25 µmol/mL (at 10-fold dilution); concentration of the compound of the present invention, 0.625, 1.25, 2.5, 5, 10, 20 µmol/L (six points).

An enzyme in a K-Pi buffer (pH 7.4) and the compound of the present invention solution as a pre-reaction solution were added to a 96-well plate at the composition of the pre-reaction, a part of it was transferred to another 96-well plate so that it was ¹⁄₁₀ diluted by a substrate in a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 was added to stop the reaction. NADPH was added to a remaining preincubation solution to initiate a preincubation (with preincubation) and, after a predetermined time of a preincubation, a part was transferred to another plate so that it was ¹⁄₁₀ diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving the compound of the present invention to a reaction system was adopted as a control (100%), remaining activity (%) was calculated at each concentration of the compound of the present invention added as the solution, and $IC_{50}$ was calculated by reverse-presumption by a logistic model using a concentration and an inhibition rate. When a difference between $IC_{50}$ values is 5 µM or more, this was defined as (+) and, when the difference is 3 µM or less, this was defined as (−).

Compound I-1: (−)

Test Example 5

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a compound of the present invention was assessed.

The reaction conditions were as follows: substrate, 0.5 µmol/L ethoxyresorufin (CYP1A2), 100 µmol/L tolbutamide (CYP2C9), 50 µmol/L S-mephenyloin (CYP2C19), 5 µmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; concentration of the compound of the present invention, 1, 5, 10, 20 µmol/L (four points).

Each five kinds of substrates, human hepatic microsome, and a compound of the present invention in 50 mmol/L Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a multi-label counter and hydroxytolbutamide (CYP2C9 metabolite), 4'-hydroxymephenyloin (CYP2C19 metabolite), dextrorphan (CYP2D6 metabolite), and terfenadine alcohol metabolite (CYP3A4 metabolite) were quantified by LC/MS/MS.

Addition of only DMSO being a solvent dissolving a compound to a reaction system was adopted as a control (100%), remaining activity (%) was calculated and $IC_{50}$ was calculated by reverse presumption by a logistic model using a concentration and an inhibition rate.

Compound I-2: five kinds >20 µM

Test Example 6

Fluctuation Ames Test

Each 20 µL of freeze-stored *Salmonella typhimurium* (TA98 and TA100 strain) is inoculated in 10 mL of liquid nutrient medium (2.5% Oxoid nutrient broth No. 2), and the cultures are incubated at 37° C. under shaking for 10 hours. 9 mL of TA98 culture is centrifuged (2000×g, 10 minutes) to remove medium, and the bacteria is suspended in 9 mL of Micro F buffer ($K_2HPO_4$: 3.5 g/L, $KH2PO_4$: 1 g/L, $(NH_4)_2SO_4$: 1 g/L, trisodium citrate dihydrate: 0.25 g/L, $MgSO_4.7H_2O$:0.1 g/L), and the suspension is added to 110 mL of Exposure medium (Micro F buffer containing Biotin: 8 µg/mL, histidine: 0.2 µg/mL, glucose: 8 mg/mL). 3.16 mL of TA100 culture is added to 120 mL of Exposure medium to prepare the test bacterial solution. 588 µL of the test bacterial solution (or mixed solution of 498 µl of the test bacterial solution and 90 µL of the S9 mix in the case with metabolic activation system) are mixed with each 12 µL of the following solution: DMSO solution of the compound of the present invention (several stage dilution from maximum dose 50 mg/mL at 2 to 3-fold ratio); DMSO as negative control; 50 µg/mL of 4-nitroquinoline-1-oxide DMSO solution as positive control for TA98 without metabolic activation system; 0.25 µg/mL of 2-(2-furyl)-3-(5-nitro-2-furyl)acrylamide DMSO solution as positive control for TA100 without metabolic activation system; 40 µg/mL of 2-aminoanthracene DMSO solution as positive control for TA98 with metabolic activation system; or 20 µg/mL of 2-aminoanthracene DMSO solution as positive control for TA100 with metabolic activation system. A mixed solution is incubated at 37° C. under shaking for 90 minutes. 460 µL of the bacterial solution exposed to the compound of the present invention is mixed with 2300 µL of Indicator medium (Micro F buffer containing biotin: 8 µg/mL, histidine: 0.2 µg/mL, glucose: 8 mg/mL, Bromo Cresol Purple: 37.5 µg/mL), each 50 µL is dispensed into 48 wells/dose in the microwell plates, and is subjected to stationary cultivation at 37° C. for 3 days. A well containing the bacteria, which has obtained the ability of proliferation by mutation in the gene coding amino acid (histidine) synthetase, turns the color from purple to yellow due to pH change. The number of the yellow wells among the 48 total wells per dose is counted, and evaluate the mutagenicity by comparing with the negative control group. (−) means that mutagenicity is negative and (+) means positive.

Test Example 7

Solubility Test

A 2-fold dilution series (12 points) of a 10 mM solution of a compound of the present invention in DMSO was added to a medium (JP-I, JP-II) (2%), and solubility was assessed by 3 stages (High; >40 µM, Medium; 3-40 µM, Low; <3 µM) from a turbidity after 4 hours.

Compound I-9: High (JP-I, JP-II)

Test Example 7-2

Solubility Test

The solubility of each compound is determined under 1% DMSO addition conditions. A 10 mmol/L solution of the compound is prepared with DMSO, and 6 µL of the compound of the present invention solution is added to 594 µL of an artificial intestinal juice (water and 118 mL of 0.2 mol/L NaOH reagent are added to 250 mL of 0.2 mol/L potassium dihydrogen phosphate reagent to reach 1000 mL) with a pH of 6.8. The mixture is left standing for 16 hours at 25° C., and the mixture is vacuum-filtered. The filtrate is two-fold diluted with methanol/water=1/1 (v/v), and the compound concentration in the filtrate is measured with HPLC or LC/MS/MS by the absolute calibration method.

Test Example 8

Metabolism Stability Test

Using a commercially available pooled human hepatic microsomes, a compound of the present invention is reacted for a constant time, a remaining rate is calculated by comparing a reacted sample and an unreacted sample, thereby, a degree of metabolism in liver of the compound of the present invention is assessed.

A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution is added to 100 µL of a methanol/acetonitrile=1/1 (v/v), mixed and centrifuged at 3000 rpm for 15 minutes. The compound of the present invention in the supernatant is quantified by LC/MS/MS, and a remaining amount of the compound of the present invention after the reaction is calculated, letting a compound amount at 0 minute reaction time to be 100%.

Compound I-5: 88%

Test Example 9 hERG Test

For the purpose of assessing risk of an electrocardiogram QT interval prolongation, effects on delayed rectifier $K^+$ current ($I_{Kr}$), which plays an important role in the ventricular repolarization process, of the compound of the present invention was studied using HEK293 cells expressing human ether-a-go-go related gene (hERG) channel.

A cell was retained at a membrane potential of −80 mV by whole cell patch clamp method using an automated patch clamp system (PatchXpress 7000A, Axon Instruments Inc.) and leakage potential at −50 mV was generated. $I_{Kr}$ induced by depolarization pulse stimulation at +40 mV for 2 seconds and, further, repolarization pulse stimulation at −50 mV for 2 seconds is recorded. After the generated current is stabilized, extracellular solution (NaCl: 135 mmol/L, KCl: 5.4 mmol/L, NaH2PO$_4$: 0.3 mmol/L, CaCl$_2$.2H$_2$O:1.8 mmol/L, MgCl$_2$.6H$_2$O: 1 mmol/L, glucose: 10 mmol/L, HEPES (4-(2-hydroxyethyl)-1-piperazine ethanesulfonic acid): 10 mmol/L, pH=7.4) in which the compound of the present invention have been dissolved at an objective concentration is applied to the cell under the room temperature condition for 10 minutes. From the recording $I_{Kr}$, an absolute value of the tail peak current is measured based on the current value at the resting membrane potential using an analysis software (DataXpress ver. 1, Molecular Devices Corporation). Further, the % inhibition relative to the tail peak current before application of the compound of the present invention is calculated, and compared with the vehicle-applied group (0.1% dimethyl sulfoxide solution) to assess influence of the compound of the present invention on $I_{Kr}$.

Test Example 10

Powder Solubility Test

Appropriate amounts of the compound of the present invention are put into appropriate containers. To the respective containers are added 200 µL of JP-1 fluid (sodium chloride 2.0 g, hydrochloric acid 7.0 mL and water to reach 1000 mL0), 200 µL of JP-2 fluid (500 mL of water is added to 50 mL of phosphate buffer (pH 6.8)), and 200 µL of 20 mmol/L sodium taurocholate (TCA)/JP-2 fluid (TCA 1.08 g and water to reach 100 mL). In the case that the compound of the present invention is dissolved after the addition of the test fluid, the compound of the present invention is added as appropriate. The containers are sealed, and shaken for 1 hour at 37° C. The mixtures are filtered, and 100 µL of methanol is added to each of the filtrate (100 µL) so that the filtrates are two-fold diluted. The dilution ratio may be changed if necessary. The dilutions are observed for bubbles and precipitates, and then the containers are sealed and shaken. Quantification is performed by HPLC with an absolute calibration method.

Test Example 11

BA Test

Materials and methods for studies on oral absorption
(1) Animal: mouse or SD rat
(2) Breeding conditions: mouse or SD rat is allowed to freely take solid feed and sterilized tap water.
(3) Dose and grouping: orally or intravenously administered at a predetermined dose; grouping is as follows (Dose depends on the compound)
Oral administration: 1 to 30 mg/kg (n=2 to 3)
Intravenous administration: 0.5 to 10 mg/kg (n=2 to 3)
(4) Preparation of dosing solution: for oral administration, in a solution or a suspension state; for intravenous administration, in a solubilized state
(5) Administration method: in oral administration, forcedly administer into ventriculus with oral probe; in intravenous administration, administer from caudal vein with a needle-equipped syringe
(6) Evaluation items: blood is collected over time, and the plasma concentration of the compound of the present invention is measured by LC/MS/MS
(7) Statistical analysis: regarding the transition of the plasma concentration of the compound of the present invention, the area under the plasma concentration-time curve (AUC) is calculated by non-linear least squares program WinNonlin (Registered trademark), and the bioavailability (BA) of the compound of the present invention is calculated from the AUCs of the oral administration group and intravenous administration group Test Example 12

Brain Distribution Studies

Compound of the present invention is intravenously administered to a rat at 0.5 mg/mL/kg dosage. 30 Minutes later, all blood is drawn from vena cava inferior under isoflurane anesthesia for death from exsanguination.

The brain is enucleated and 20-25% of homogenate thereof is prepared with distilled water.

The obtained blood is used as plasma after centrifuging. To the brain sample is added the control plasma at 1:1. To the plasma samples is added the control brains at 1:1. Each sample is measured using LC/MS/MS. The obtained area ratio (a brain/plasma) is used for the brain Kp value.

Test Example 13

Ames Test

Ames test is performed by using Salmonellas (*Salmonella typhimurium*) TA 98, TA100, TA1535 and TA1537 and *Escherichia coli* WP2uvrA as test strains with or without metabolic activation in the pre-incubation method to check the presence or absence of gene mutagenicity of compounds of the present invention.

Test Example 14

P-gp Substrate Test

Compound of the present invention is added in one side of the trans well wherein human MDR1 expressing cells or parent cells are monolayer cultivated, and reacted for a pre-determined period of times. Efflux Ratio (ER; ratio of membrane permeability coefficients of the direction from Basolateral side to Apical side (B to A) and the direction from Apical side to Basolateral side (A to B)) of MDR1 expressing cells and parent cells is calculated from the membrane permeability coefficients of A to B and of B to A. The compound of the present invention is investigated whether a P-gp substrate or not by comparing ER values of MDR1 expressing cells and parent cells.

FORMULATION EXAMPLES

The following Formulation Examples are only exemplified and not intended to limit the scope of the present invention.

Formulation Example 1

Tablets

| Compound of the present invention | 15 mg |
| Lactose | 15 mg |
| Calcium stearate | 3 mg |

All of the above ingredients except for calcium stearate are uniformly mixed. Then the mixture is crushed, granulated and dried to obtain a suitable size of granules. Then, calcium stearate is added to the granules. Finally, tableting is performed under a compression force.

Formulation Example 2

Capsules

| Compound of the present invention | 10 mg |
| Magnesium stearate | 10 mg |
| Lactose | 80 mg |

The above ingredients are mixed uniformly to obtain powders or fine granules, and then the obtained mixture is filled in capsules.

Formulation Example 3

Granules

| Compound of the present invention | 30 g |
| Lactose | 265 g |
| Magnesium stearate | 5 g |

After the above ingredients are mixed uniformly, the mixture is compressed.

The compressed matters are crushed, granulated and sieved to obtain suitable size of granules.

INDUSTRIAL APPLICABILITY

The compound of the present invention can be a useful medicament for diseases induced by production, secretion and/or deposition of amyloid β proteins.

The invention claimed is:

1. A compound of the formula (I):

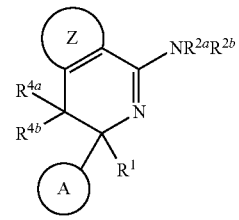

wherein

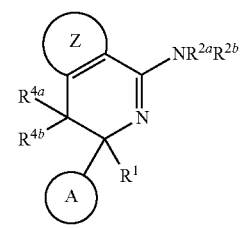 is

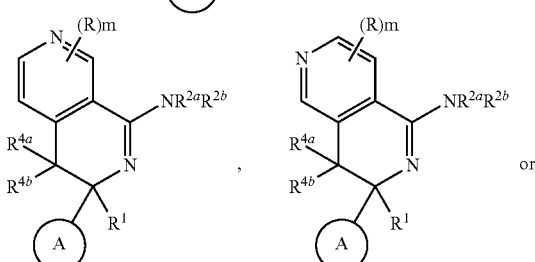

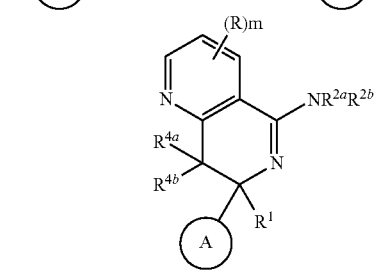

where R is each independently halogen, hydroxy, substituted or unsubstituted alkyl, substituted or unsubstituted alkenyl, substituted or unsubstituted alkoxy, substituted or unsubstituted alkenyloxy, substituted or unsubstituted alkylthio, substituted or unsubstituted alkenylthio, substituted or unsubstituted acyl, substituted or unsubstituted acyloxy, cyano, carboxy, substituted or unsubstituted alkoxycarbonyl, substituted or unsubstituted alkenyloxycarbonyl, substituted or unsubstituted amino, substituted or unsubstituted carbamoyl, substituted or unsubstituted carbocyclyl, substituted or unsubstituted carbocyclyloxy, substituted or unsubstituted carbocyclyloxycarbonyl, substituted or unsubstituted carbocyclylsulfinyl, substituted or unsubstituted heterocyclyl, substituted or unsubstituted heterocyclyloxy or substituted or unsubstituted heterocyclyloxycarbonyl, m is an integer of 0 to 3, ring A is (1) any one of the following groups:

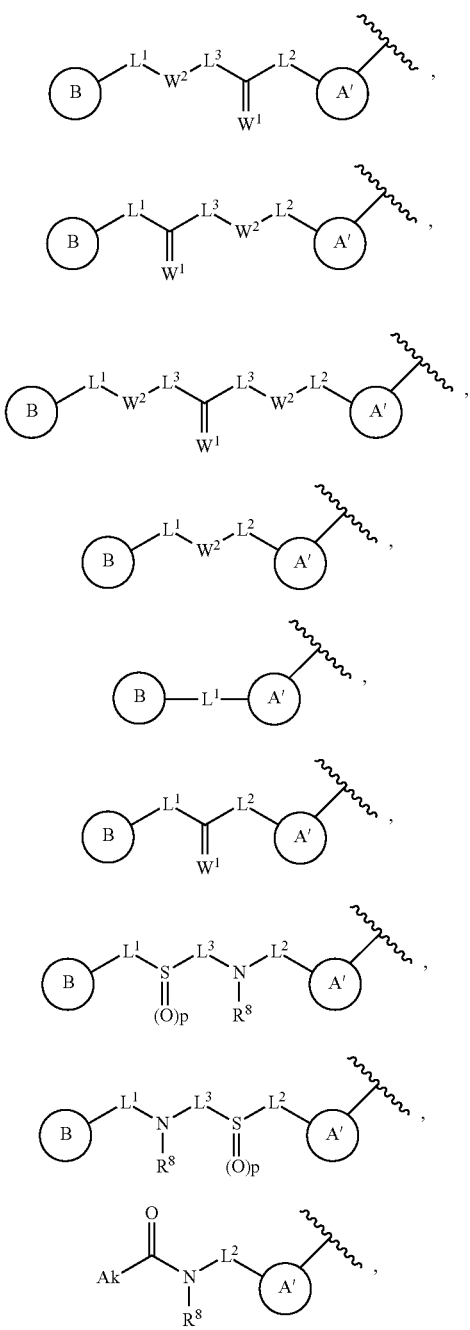

or (2) a substituted or unsubstituted carbocycle or a substituted or unsubstituted heterocycle, wherein ring A' and ring B are each independently a substituted or unsubstituted carbocycle or a substituted or unsubstituted heterocycle, the substituent of "substituted or unsubstituted carbocycle" and "substituted or unsubstituted heterocycle" as ring A and ring B are one or more substituents selected from:

(a) a group selected from the substituent group α;
(b) alkyl substituted with one or more substituents selected from the substituent group α, hydroxyimino and alkoxyimino; or unsubstituted alkyl
(c) aminoalkyl substituted with one or more substituents selected from the substituent group α;
(d) alkenyl substituted with one or more substituents selected from the substituent group α; or unsubstituted alkenyl
(e) alkynyl substituted with one or more substituents selected from the substituent group α; or unsubstituted alkynyl;
(f) alkoxy substituted with one or more substituents selected from the substituent group α;
(g) alkoxyalkoxy substituted with one or more substituents selected from the substituent group α;
(h) alkenyloxy substituted with one or more substituents selected from the substituent group α; or unsubstituted alkenyloxy;
(i) alkoxyalkenyloxy substituted with one or more substituents selected from the substituent group α;
(j) alkynyloxy substituted with one or more substituents selected from the substituent group α; or unsubstituted alkynyloxy;
(k) alkoxyalkynyloxy substituted with one or more substituents selected from the substituent group α;
(l) alkylthio substituted with one or more substituents selected from the substituent group α; or unsubstituted alkylthio;
(m) alkenylthio substituted with one or more substituents selected from the substituent group α; or unsubstituted alkenylthio;
(n) alkynylthio substituted with one or more substituents selected from the substituent group α; or unsubstituted alkynylthio;
(o) alkylamino substituted with one or more substituents selected from the substituent group α;
(p) alkenylamino substituted with one or more substituents selected from the substituent group α;
(q) alkynylamino substituted with one or more substituents selected from the substituent group α;
(r) aminooxy substituted with one or more substituents selected from the substituent group α and alkylidene; or unsubstituted aminooxy;
(s) acyl substituted with one or more substituents selected from the substituent group α;
(t) alkylsulfonyl substituted with one or more substituents selected from the substituent group α; or unsubstituted alkylsulfonyl;
(u) alkylsulfinyl substituted with one or more substituents selected from the substituent group α; or unsubstituted alkylsulfinyl;
(v) alkylsulfamoyl substituted with one or more substituents selected from the substituent groupc α;
(w) carbocyclyl substituted with one or more substituents selected from the substituent group α, azide, alkyl and halogenoalkyl;
(x) heterocyclyl substituted with one or more substituents selected from the substituent group α, azide, alkyl and halogenoalkyl;
(y) carbocyclylalkyl substituted with one or more substituents selected from the substituent group α, azide, alkyl and halogenoalkyl; or unsubstituted carbocyclylalkyl, (z) heterocyclylalkyl substituted with one or more substituents selected from the substituent group α, azide, alkyl and halogenoalkyl; or unsubstituted heterocyclylalkyl;

(aa) carbocyclyloxy substituted with one or more substituents selected from the substituent group α, azide, alkyl and halogenoalkyl; or unsubstituted carbocyclyloxy;

(ab) heterocyclyloxy substituted with one or more substituents selected from the substituent group α, azide, alkyl and halogenoalkyl; or unsubstituted heterocyclyloxy;

(ac) carbocyclylalkoxy substituted with one or more substituents selected from the substituent group α, azide, alkyl and halogenoalkyl; or unsubstituted carbocyclylalkoxy;

(ad) heterocyclylalkoxy substituted with one or more substituents selected from the substituent group α, azide, alkyl and halogenoalkyl; or unsubstituted heterocyclylalkoxy;

(ae) carbocyclylalkoxycarbonyl substituted with one or more substituents selected from the substituent group α, azide, alkyl and halogenoalkyl; or unsubstituted carbocyclylalkoxycarbonyl;

(af) heterocyclylalkoxycarbonyl substituted with one or more substituents selected from the substituent group α, azide, alkyl and halogenoalkyl; or unsubstituted heterocyclylalkoxycarbonyl;

(ag) carbocyclylthio substituted with one or more substituents selected from the substituent group α, azide, alkyl and halogenoalkyl; or unsubstituted carbocyclylthio;

(ah) heterocyclylthio substituted with one or more substituents selected from the substituent group α, azide, alkyl and halogenoalkyl; or unsubstituted heterocyclylthio;

(ai) carbocyclylamino substituted with one or more substituents selected from the substituent group α, azide, alkyl and halogenoalkyl; or unsubstituted carbocyclylamino;

(aj) heterocyclylamino substituted with one or more substituents selected from the substituent group α, azide, alkyl and halogenoalkyl; or unsubstituted heterocyclylamino;

(ak) carbocyclylalkylamino substituted with one or more substituents selected from the substituent group α, azide, alkyl and halogenoalkyl; or unsubstituted carbocyclylalkylamino;

(al) heterocyclylalkylamino substituted with one or more substituents selected from the substituent group α, azide, alkyl and halogenoalkyl; or unsubstituted heterocyclylalkylamino;

(am) carbocyclylsulfamoyl substituted with one or more substituents selected from the substituent group α, azide, alkyl and halogenoalkyl; or unsubstituted carbocyclylsulfamoyl;

(an) heterocyclylsulfamoyl substituted with one or more substituents selected from the substituent group α, azide, alkyl and halogenoalkyl; or unsubstituted heterocyclylsulfamoyl;

(ao) carbocyclylsulfonyl substituted with one or more substituents selected from the substituent group α, azide, alkyl and halogenoalkyl; or unsubstituted carbocyclylsulfonyl;

(ap) heterocyclylsulfonyl substituted with one or more substituents selected from the substituent group α, azide, alkyl and halogenoalkyl; or unsubstituted heterocyclylsulfonyl;

(aq) carbocyclylcarbamoyl substituted with one or more substituents selected from the substituent group α, azide, alkyl and halogenoalkyl; or unsubstituted carbocyclylcarbamoyl;

(ar) heterocyclylcarbamoyl substituted with one or more substituents selected from the substituent group α, azide alkyl and halogenoalkyl; or unsubstituted heterocyclylcarbamoyl;

(as) carbocyclylalkylcarbamoyl substituted with one or more substituents selected from the substituent group α, azide, alkyl and halogenoalkyl; or unsubstituted carbocyclylalkylcarbamoyl;

(at) heterocyclylalkylcarbamoyl substituted with one or more substituents selected from the substituent group α, azide, alkyl and halogenoalkyl; or unsubstituted heterocyclylalkylcarbamoyl;

(au) carbocyclyloxycarbonyl substituted with one or more substituents selected from the substituent group α, azide, alkyl and halogenoalkyl; or unsubstituted carbocyclyloxycarbonyl;

(av) heterocyclyloxycarbonyl substituted with one or more substituents selected from the substituent group α, azide, alkyl and halogenoalkyl; or unsubstituted heterocyclyloxycarbonyl;

(aw) alkylenedioxy substituted with halogen; or unsubstituted alkylenedioxy;

(ax) oxo; and (ay) azido;

the substituent of "a substituted or unsubstituted carbocycle", and "a substituted or unsubstituted heterocycle" as ring A' are one or more selected from halogen, cyano, hydroxy, nitro, carboxy, alkyl substituted with one or more substituents selected from the substituent group α, unsubstituted alkyl, alkoxy substituted with one or more substituents selected from the substituent group α, unsubstituted alkoxy, amino substituted with one or more substituents selected from the substituent group α, unsubstituted amino, carbamoyl substituted with one or more substituents selected from the substituent group α, unsubstituted carbamoyl, alkoxycarbonyl substituted with one or more substituents selected from the substituent group α, and unsubstituted alkoxycarbonyl;

$L^1$, $L^2$ and $L^3$ are each independently a bond, substituted or unsubstituted alkylene, substituted or unsubstituted alkenylene or substituted or unsubstituted alkynylene, =$W^1$ is =O, =S or =$NR^9$, $W^2$ is O, S or $NR^8$, $R^8$ is hydrogen, substituted or unsubstituted alkyl, substituted or unsubstituted alkenyl, substituted or unsubstituted alkynyl or substituted or unsubstituted acyl, $R^9$ is hydrogen, hydroxy, substituted or unsubstituted alkyl, substituted or unsubstituted alkenyl, substituted or unsubstituted alkynyl or substituted or unsubstituted acyl, Ak is substituted or unsubstituted alkyl, substituted or unsubstituted alkenyl or substituted or unsubstituted alkynyl, when ring A is (i), the constituent carbon atom of $L^1$ and the constituent carbon atom of $L^2$, or the nitrogen atom of $W^2$ and the constituent carbon atom of $L^2$ may be connected with substituted or unsubstituted alkylene to form a ring, when ring A is (ii), the constituent carbon atom of $L^1$ and the constituent carbon atom of $L^2$, or the constituent carbon atom of $L^1$ and the nitrogen atom of $W^2$ may be connected with substituted or unsubstituted alkylene to form a ring, when ring A is (iii), two nitrogen atoms of W² may be connected with substituted or unsubstituted alkylene to form a ring, when ring A is (vi), the constituent carbon atom of L¹ and the constituent carbon atom of L² may be connected by substituted or unsubstituted alkylene to form a ring, p is 1 or 2, and when multiple L³, multiple W², multiple R⁹ or multiple R¹¹ are present, each of them may be independently different;

R¹ is unsubstituted alkyl or halogenoalkyl,

R²ᵃ and R²ᵇ are each independently hydrogen, substituted or unsubstituted alkyl, substituted or unsubstituted acyl, substituted or unsubstituted alkoxycarbonyl or substituted or unsubstituted carbamoyl, R⁴ᵃ and R⁴ᵇ are each independently hydrogen, halogen, or unsubstituted alkyl, wherein "substituted or unsubstituted alkyl" may be substituted with one or more substituents selected from a substituent group α;

the substituent group α is a group consisting of halogen, hydroxy, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkylcarbamoyl, sulfamoyl, alkylsulfamoyl, alkylsulfinyl, alkylsulfonylamino, alkylsulfonylalkylamino, alkylsulfonylimino, alkylsulfinylamino, alkylsulfinylalkylamino, alkylsulfinylimino, cyano, nitro, carbocyclyl and heterocyclyl wherein each of the carbocycle and heterocycle may be substituted with one or more substituents selected from halogen, alkyl, hydroxy and alkoxy;

the substituent of "substituted or unsubstituted alkoxy", "substituted or unsubstituted alkoxycarbonyl", "substituted or unsubstituted alkylthio", "substituted or unsubstituted alkylsulfinyl" and "substituted or unsubstituted alkylsulfonyl" are one or more substituents selected from the substituent group α;

the substituent of "substituted or unsubstituted alkenyl", "substituted or unsubstituted alkenyloxy", "substituted or unsubstituted alkenylthio", "substituted or unsubstituted alkenyloxycarbonyl", "substituted or unsubstituted alkenylsulfinyl", "substituted or unsubstituted alkenylsulfonyl", "substituted or unsubstituted alkynyl", "substituted or unsubstituted alkynyloxy", "substituted or unsubstituted alkynyloxycarbonyl", "substituted or unsubstituted alkynylthio", "substituted or unsubstituted alkynylsulfinyl" and "substituted or unsubstituted alkynylsulfonyl" are one or more substituents selected form the substituent group α;

the substituents of "substituted or unsubstituted amino", "substituted or unsubstituted carbamoyl", "substituted or unsubstituted thiocarbamoyl" and "substituted or unsubstituted sulfamoyl" are 1 or 2 substituents selected from alkyl, acyl, hydroxy, alkoxy, alkoxycarbonyl, carbocyclyl and heterocyclyl;

the substituents of "substituted or unsubstituted acyl" and "substituted or unsubstituted acyloxy" are one or more substituents selected from the substituent group α;

the substituent of "substituted or unsubstituted carbocyclyl", "substituted or unsubstituted heterocyclyl", "substituted or unsubstituted carbocyclylalkyl", "substituted or unsubstituted carbocyclylalkoxy", "substituted or unsubstituted carbocyclyloxy", "substituted or unsubstituted carbocyclylthio", "substituted or unsubstituted carbocyclyloxycarbonyl", "substituted or unsubstituted carbocyclylsulfinyl", "substituted or unsubstituted carbocyclylsulfonyl", "substituted or unsubstituted heterocyclyloxy", "substituted or unsubstituted heterocyclylthio", "substituted or unsubstituted heterocyclyloxycarbonyl", "substituted or unsubstituted heterocyclylsulfinyl", "substituted or unsubstituted heterocyclylsulfonyl", "a substituted or unsubstituted carbocycle" and "a substituted or unsubstituted heterocycle" as other than the above ring A, ring A', ring B and ring Z are one or more substituents selected from alkyl substituted with one or more substituents selected from the substituent group α, unsubstituted alkyl and the substituent group α the substituents of "substituted or unsubstituted alkylene", "substituted or unsubstituted alkenylene" and "substituted or unsubstituted alkynylene" are one or more substituents selected from the substituent group α or its pharmaceutically acceptable salt.

2. The compound according to claim 1, wherein ring A is

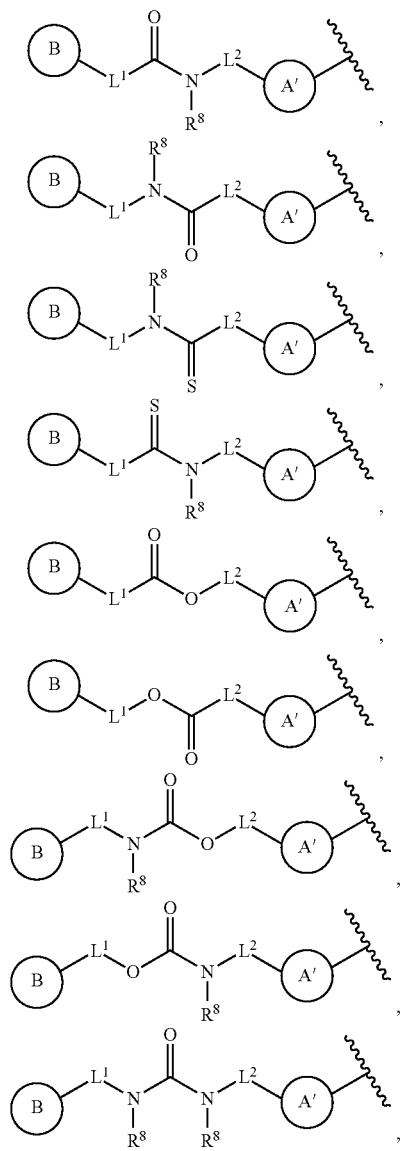

-continued

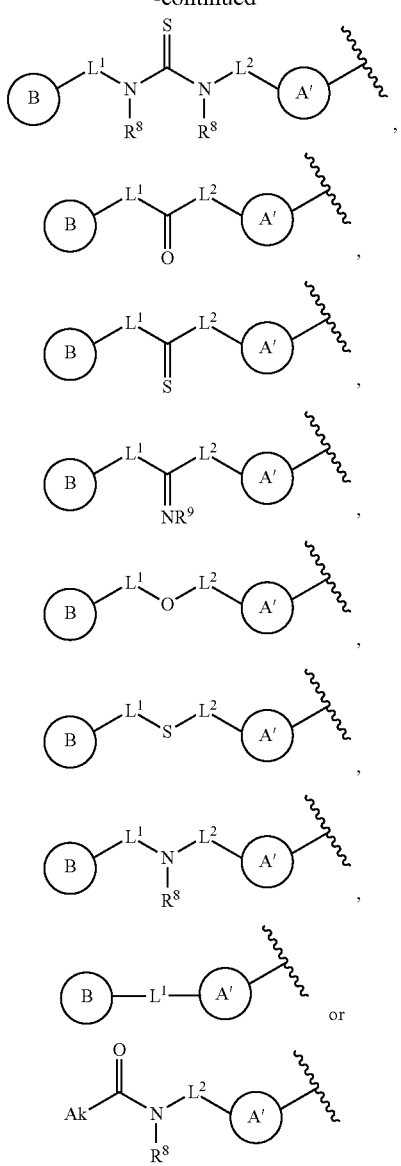

wherein ring A' and ring B are each independently a substituted or unsubstituted carbocycle or a substituted or unsubstituted heterocycle, L¹ and L² are each independently a bond, substituted or unsubstituted alkylene, substituted or unsubstituted alkenylene or substituted or unsubstituted alkynylene, R⁸ is hydrogen, substituted or unsubstituted alkyl, substituted or unsubstituted alkenyl, substituted or unsubstituted alkynyl or substituted or unsubstituted acyl, R⁹ is hydrogen, hydroxy, substituted or unsubstituted alkyl, substituted or unsubstituted alkenyl, substituted or unsubstituted alkynyl or substituted or unsubstituted acyl, and Ak is substituted or unsubstituted alkyl, substituted or unsubstituted alkenyl or substituted or unsubstituted alkynyl, or its pharmaceutically acceptable salt.

3. The compound according to claim 2 wherein ring A is

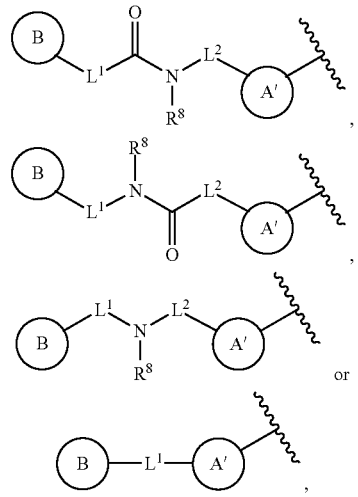

or its pharmaceutically acceptable salt.

4. The compound according to claim 2, wherein each of L¹ and L² is a bond, or its pharmaceutically acceptable salt.

5. The compound according to claim 2, wherein ring A' is substituted or unsubstituted benzene or substituted or unsubstituted pyridine, and ring B is substituted or unsubstituted pyridine, substituted or unsubstituted pyrimidine or substituted or unsubstituted pyrazine, wherein the substituents of the "substituted or unsubstituted benzene", and "substituted or unsubstituted pyridine" in ring A' are one or more selected from halogen, cyano, hydroxy, nitro, carboxy, alkyl substituted with one or more substituents selected from the substituent group α, unsubstituted alkyl, alkoxy substituted with one or more substituents selected from the substituent group α, unsubstituted alkoxy, amino substituted with one or more substituents selected from the substituent group α, unsubstituted amino, carbamoyl substituted with one or more substituents selected from the substituent group α, unsubstituted carbamoyl, alkoxycarbonyl substituted with one or more substituents selected from the substituent group α, and unsubstituted alkoxycarbonyl;

the substituents of the "substituted or unsubstituted pyridine", "substituted or unsubstituted pyrimidine" and "substituted or unsubstituted pyrazine" in ring B are one or more substituents selected from the above (a) to (ay);

or its pharmaceutically acceptable salt.

6. The compound according to claim 1, wherein R¹ is unsubstituted alkyl having a carbon number of 1 to 3, or its pharmaceutically acceptable salt.

7. The compound according to claim 1, wherein R²ᵃ and R²ᵇ are both hydrogen, or its pharmaceutically acceptable salt.

8. A pharmaceutical composition comprising the compound according to claim 1, or its pharmaceutically acceptable salt.

9. A pharmaceutical composition having BACE1 inhibitory activity comprising the compound according to claim 1, or its pharmaceutically acceptable salt.

10. A method for inhibiting BACE1 activity comprising administering the compound according to claim 1, or its pharmaceutically acceptable salt.

11. A compound according to claim 1, or its pharmaceutically acceptable salt for use in a method for inhibiting BACE1 activity.

12. The compound according to claim 1, wherein $R^1$ is unsubstituted alkyl or fluoroalkyl, or its pharmaceutically acceptable salt.

13. The compound according to claim 1, wherein $R^{4a}$ and $R^{4b}$ are each independently hydrogen, fluorine, or unsubstituted alkyl, or its pharmaceutically acceptable salt.

14. The compound according to claim 1, wherein $R^{4a}$ and $R^{4b}$ are each independently hydrogen or unsubstituted alkyl, or its pharmaceutically acceptable salt.

15. The compound according to claim 1, wherein $R^{4a}$ is hydrogen, or its pharmaceutically acceptable salt.

16. The compound according to claim 1, wherein $R^{4a}$ and $R^{4b}$ are both hydrogen, or its pharmaceutically acceptable salt.

* * * * *